US009434698B2

(12) United States Patent
Shekhar et al.

(10) Patent No.: US 9,434,698 B2
(45) Date of Patent: *Sep. 6, 2016

(54) PROCESS FOR PREPARING ANTIVIRAL COMPOUNDS

(71) Applicant: AbbVie Inc., North Chicago, IL (US)

(72) Inventors: Shashank Shekhar, Vernon Hills, IL (US); Thaddeus S. Franczyk, Lake Villa, IL (US); David M. Barnes, Bristol, WI (US); Travis B. Dunn, Gurnee, IL (US); Anthony R. Haight, Wadsworth, IL (US); Vincent S. Chan, Evanston, IL (US)

(73) Assignee: ABBVIE INC., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/536,192

(22) Filed: Nov. 7, 2014

(65) Prior Publication Data

US 2015/0191437 A1    Jul. 9, 2015

Related U.S. Application Data

(60) Division of application No. 13/591,090, filed on Aug. 21, 2012, which is a continuation-in-part of application No. 13/184,440, filed on Jul. 15, 2011, now Pat. No. 8,895,737.

(60) Provisional application No. 61/444,475, filed on Feb. 18, 2011, provisional application No. 61/365,293, filed on Jul. 16, 2010.

(51) Int. Cl.
| | |
|---|---|
| *C07D 239/54* | (2006.01) |
| *A61K 31/505* | (2006.01) |
| *B01J 31/24* | (2006.01) |
| *C07D 239/10* | (2006.01) |
| *A61K 31/513* | (2006.01) |
| *A61K 45/06* | (2006.01) |
| *A61K 38/21* | (2006.01) |
| *A61K 31/7056* | (2006.01) |

(52) U.S. Cl.
CPC ........... *C07D 239/54* (2013.01); *A61K 31/513* (2013.01); *A61K 31/7056* (2013.01); *A61K 38/21* (2013.01); *A61K 45/06* (2013.01); *B01J 31/2423* (2013.01); *C07D 239/10* (2013.01); *B01J 2231/4211* (2013.01); *B01J 2231/4227* (2013.01); *B01J 2231/4283* (2013.01); *B01J 2231/4288* (2013.01); *B01J 2231/4294* (2013.01); *B01J 2231/49* (2013.01); *B01J 2531/824* (2013.01)

(58) Field of Classification Search
CPC   C07D 239/54; A61K 31/505; B01J 31/2423
USPC ........................................ 544/309; 514/269
See application file for complete search history.

(56) References Cited

U.S. PATENT DOCUMENTS

| | | | |
|---|---|---|---|
| 4,239,888 | A | 12/1980 | Miller |
| 4,588,729 | A | 5/1986 | Teranishi et al. |
| 4,731,472 | A | 3/1988 | Pietruszkiewicz et al. |
| 4,873,238 | A | 10/1989 | Kinney et al. |
| 4,958,023 | A | 9/1990 | Kinney et al. |
| 5,084,084 | A | 1/1992 | Satow et al. |
| 5,127,935 | A | 7/1992 | Satow et al. |
| 5,154,755 | A | 10/1992 | Satow et al. |
| 5,162,326 | A | 11/1992 | Naka et al. |
| 5,164,396 | A | 11/1992 | Grosscurt et al. |
| 5,455,377 | A | 10/1995 | Ronchi et al. |
| 5,508,438 | A | 4/1996 | Broger et al. |
| 6,031,105 | A | 2/2000 | Wright |
| 6,307,087 | B1 | 10/2001 | Buchwald et al. |
| 6,380,387 | B1 | 4/2002 | Sidduri et al. |
| 6,395,916 | B1 | 5/2002 | Buchwald et al. |
| 6,537,948 | B1 | 3/2003 | Tohyama et al. |
| 6,867,310 | B1 | 3/2005 | Buchwald et al. |
| 6,946,560 | B2 | 9/2005 | Buchwald et al. |
| 7,026,498 | B2 | 4/2006 | Buchwald et al. |
| 7,223,879 | B2 | 5/2007 | Buchwald et al. |
| 7,247,731 | B2 | 7/2007 | Buchwald et al. |
| 7,560,582 | B2 | 7/2009 | Buchwald et al. |
| 7,560,596 | B2 | 7/2009 | Buchwald et al. |
| 7,858,784 | B2 | 12/2010 | Buchwald et al. |
| 8,158,631 | B2 | 4/2012 | Chin et al. |
| 8,415,351 | B2 | 4/2013 | Wagner et al. |

(Continued)

FOREIGN PATENT DOCUMENTS

| | | |
|---|---|---|
| DE | 19920847 A1 | 11/2000 |
| EP | 0647648 A1 | 4/1995 |

(Continued)

OTHER PUBLICATIONS

Alcaraz L., et al., "Novel N-aryl and N-heteroaryl Sulfamide Synthesis via Palladium Cross Coupling," Organic Letters, 2004, vol. 6 (16), pp. 2705-2708.
Anderson S., et al., "Benzofuran Trimers for Organic Electroluminescence," Chemistry—A European Journal, 2004, vol. 10 (2), pp. 518-527.
Ansel H.C., et al., Ansel's Pharmaceutical Dosage forms and Drug Delivery Systems, 8th Edition, Lippincott Williams & Wilkins, 2005, Table of Contents.
Audisio D., et al., "A Convenient and Expeditious Synthesis of 3-(n-substituted) Aminocoumarins via Palladium-catalyzed Buchwald-hartwig Coupling Reaction," Tetrahedron Letters, 2007, vol. 48 (39), pp. 6928-6932.
Aulton M.E., ed., The Design of Dosage Forms : in Pharmaceutics: The Science of Dosage Form Design, 2nd Edition, Churchill Livingstone, 2004, Table of Contents.

(Continued)

*Primary Examiner* — Venkataraman Balasubramanian
(74) *Attorney, Agent, or Firm* — Neal, Gerber & Eisenberg LLP

(57) ABSTRACT

This disclosure is directed to: (a) processes for preparing compounds and salts thereof that, inter alia, are useful for inhibiting hepatitis C virus (HCV); (b) intermediates useful for the preparation of the compounds and salts; (c) pharmaceutical compositions comprising the compounds or salts; and (d) methods of use of such compositions.

30 Claims, 1 Drawing Sheet

(56) References Cited

U.S. PATENT DOCUMENTS

| | | | |
|---|---|---|---|
| 8,501,238 | B2 | 8/2013 | Flentge et al. |
| 8,841,487 | B2 | 9/2014 | Shekhar et al. |
| 8,895,737 | B2 * | 11/2014 | Shekhar et al. ............. 544/309 |
| 2004/0106512 | A1 | 6/2004 | Mackewitz et al. |
| 2005/0143349 | A1 | 6/2005 | Bridges |
| 2005/0143422 | A1 | 6/2005 | Levin et al. |
| 2006/0142269 | A1 | 6/2006 | Dykes |
| 2009/0287016 | A1 | 11/2009 | Buchwald et al. |
| 2010/0204218 | A1 | 8/2010 | Takahashi et al. |
| 2011/0005533 | A1 | 1/2011 | Evans |
| 2011/0015401 | A1 | 1/2011 | Buchwald et al. |
| 2011/0213176 | A1 | 9/2011 | Ishii et al. |
| 2012/0014913 | A1 | 1/2012 | Shekhar et al. |
| 2012/0022252 | A1 | 1/2012 | Shekhar et al. |
| 2013/0165673 | A1 | 6/2013 | Bailly et al. |

FOREIGN PATENT DOCUMENTS

| | | |
|---|---|---|
| JP | 5213755 A | 8/1993 |
| JP | H0736069 A | 2/1995 |
| WO | WO-9209545 A2 | 6/1992 |
| WO | WO-9502567 A1 | 1/1995 |
| WO | WO-9705117 A1 | 2/1997 |
| WO | WO-9718179 A1 | 5/1997 |
| WO | WO-9815515 A1 | 4/1998 |
| WO | WO-9824429 A1 | 6/1998 |
| WO | WO-9918057 A1 | 4/1999 |
| WO | WO-9928290 A1 | 6/1999 |
| WO | WO-9943643 A2 | 9/1999 |
| WO | WO-0004865 A2 | 2/2000 |
| WO | WO-0005199 A1 | 2/2000 |
| WO | WO-0002887 B1 | 8/2000 |
| WO | WO-0119761 A2 | 3/2001 |
| WO | WO-0138337 A2 | 5/2001 |
| WO | WO-0142179 A1 | 6/2001 |
| WO | WO-0142225 A2 | 6/2001 |
| WO | WO-0190121 A2 | 11/2001 |
| WO | WO-0204445 A1 | 1/2002 |
| WO | WO-0142225 A3 | 2/2002 |
| WO | WO-0246150 A2 | 6/2002 |
| WO | WO-02085838 A1 | 10/2002 |
| WO | WO-03013502 A1 | 2/2003 |
| WO | WO-03053971 A1 | 7/2003 |
| WO | WO-03066570 A1 | 8/2003 |
| WO | WO-03074169 A2 | 9/2003 |
| WO | WO-2004013094 A2 | 2/2004 |
| WO | WO-2004018414 A2 | 3/2004 |
| WO | WO-2004018428 A1 | 3/2004 |
| WO | WO-2004018461 A2 | 3/2004 |
| WO | WO-2004031195 A1 | 4/2004 |
| WO | WO-2004052939 A2 | 6/2004 |
| WO | WO-2005021500 A1 | 3/2005 |
| WO | WO-2005065683 A1 | 7/2005 |
| WO | WO-2005079378 A2 | 9/2005 |
| WO | WO-2006051378 A1 | 5/2006 |
| WO | WO-2006064218 A1 | 6/2006 |
| WO | WO-2006066174 A1 | 6/2006 |
| WO | WO-2006074315 A2 | 7/2006 |
| WO | WO-2006095263 A1 | 9/2006 |
| WO | WO-2006097817 A1 | 9/2006 |
| WO | WO-2007133637 A2 | 11/2007 |
| WO | WO-2009010454 A2 | 1/2009 |
| WO | WO-2009039127 A1 | 3/2009 |
| WO | WO-2009039134 A1 | 3/2009 |
| WO | WO-2009039135 A1 | 3/2009 |
| WO | WO-2009076622 A2 | 6/2009 |
| WO | WO-2010010017 A1 | 1/2010 |
| WO | WO-2010051926 A2 | 5/2010 |
| WO | WO-2010111348 A1 | 9/2010 |
| WO | WO-2011008618 A1 | 1/2011 |
| WO | WO-2011008725 A2 | 1/2011 |
| WO | WO-2011071840 A1 | 6/2011 |
| WO | WO-2011072275 A2 | 6/2011 |
| WO | WO-2011082400 A2 | 7/2011 |
| WO | WO-2011133795 A2 | 10/2011 |
| WO | WO-2011146358 A1 | 11/2011 |

OTHER PUBLICATIONS

Austin W.B., et al., "Facile Synthesis of Ethynylated Benzoic Acid Derivatives and Aromatic Compounds via Ethynyltrimethylsilane," Journal of Organic Chemistry, 1981, vol. 46 (11), pp. 2280-2286.

Baltrushis R.S., et al., "Bromo Derivatives of 1-(4-hydroxyphenyl)dihydrouracil and -(4-hydroxyphenyl)-5- or -6-Methyldihydrouracils," Chemistry of Heterocyclic Compounds, 1982, vol. 18 (9), pp. 1251-1254.

Bates R.W., et al., "Synthesis of Phenolic Natural Products Using Palladium Catalyzed Coupling Reactions," Tetrahedron, 1995, vol. 51 (30), pp. 8199-8212.

Bhuyan R., et al., "Efficient Copper-Catalyzed Benzylic Amidation With Anhydrous Chloramine-T," Organic Letters, 2007, vol. 9 (20), pp. 3957-3959.

Blight K.J., et al., "Efficient Initiation of HCV RNA Replication in Cell Culture," 2000, vol. 290 (5498), pp. 1972-1974.

Blight K.J., et al., "Efficient Replication of Hepatitis C Virus Genotype 1 a RNAs in Cell Culture," 2003, vol. 77 (5), pp. 3181-3190.

Bonnaventure I., et al., "Probing the Importance of the Hemilabile Site of Bis(phosphine) Monoxide Ligands in the Copper-Catalyzed Addition of Diethylzinc to N-Phosphinoylimines: Discovery of New Effective Chiral Ligands," The Journal of Organic Chemistry, 2008, vol. 73 (16), pp. 6330-6340.

Burk M.J., et al., "C2-symmetric bis(phospholanes) and their use in highly enantioselective hydrogenation reactions," Journal of the American Chemical Society, 1991, vol. 113 (22), pp. 8518-8519.

Burk M.J., et al., "Modular Phospholane Ligands in Asymmetric Catalysis," Accounts of Chemical Research, 2000, vol. 33 (6), pp. 363-372.

Burk M.J., et al., "Preparation and Use of C2-Symmetric Bis(phospholanes): Production of a-amino Acid Derivatives via Highly Enantioselective Hydrogenation Reactions," Journal of the American Chemical Society, 1993, vol. 115, pp. 10125-10138.

Burton G., et al., "Palladium-catalyzed Intermolecular Coupling of Aryl Chlorides and Sulfonamides Under Microwave Irradiation," Organic Letters, 2003, vol. 5 (23), pp. 4373-4376.

Chan J., et al., "Rh(Ii)-Catalyzed Intermolecular Oxidative Sulfamidation of Aldehydes: A Mild Efficient Synthesis of N-Sulfonylcarboxamides," Journal of the American Chemical Society, 2007, vol. 129 (46), pp. 14106-14107.

De Francesco R., et al., "Approaching a new era for Hepatitis C virus Therapy: Inhibitors of the NS3-4A Serine Protease and the NS5B RNA-Dependent RNA Polymerase," Antiviral Research, 2003, vol. 58 (1), pp. 1-16.

De Francesco R., et al., "Challenges and Successes in Developing New Therapies for Hepatitis C," Nature, 2005, vol. 436 (7053), pp. 953-960.

Diaz A.A., et al., "Facile Synthesis of Unsymmetrical 9-phospha- and 9-arsafluorenes," Inorganic Chemistry, 2006, vol. 45 (14), pp. 5568-5575.

Driver M.S., et al., "Carbon—Nitrogen-Bond-Forming Reductive Elimination of Arylamines from Palladium(II) Phosphine Complexes," Journal of the American Chemical Society, 1997, vol. 119 (35), pp. 8232-8245.

Erre G., et al., "Novel Rhodium Catalyst for Asymmetric Hydrofomylation of Styrene: Study of Electronic and Steric Effects of Phosphorus Seven-Membered Ring Ligands," Journal of Molecular Catalysis A: Chemical, 2008, vol. 280, pp. 148-155.

Fleury-Bregeot N., et al., "Stereospecific Synthesis, Structural Characterisation and Resolution of 2-Phospha[3]ferrocenophane Derivatives—a New Chiral Scaffold," European Journal of Inorganic Chemistry, 2007, pp. 3853-3862.

Fors B.P., et al., "An Efficient System for the Pd-Catalyzed Cross-Coupling of Amides and Aryl Chlorides," Tetrahedron, 2009, vol. 65 (33), pp. 6576-6583.

(56) References Cited

OTHER PUBLICATIONS

Fors B.P., et al., "Water-Mediated Catalyst Preactivation: An Efficient Protocol for C—N Cross-Coupling Reactions," Organic Letters, 2008, vol. 10 (16), pp. 3505-3508.
Giner X., et al., "(Triphenyl Phosphite)Gold(I)-Catalyzed Intermolecular Hydroamination of Alkenes and 1,3-Dienes," Organic Letters, 2008, vol. 10 (14), pp. 2919-2922.
Gravel M., et al., "Practical Procedure for the Preparation of Functionalized (E)-1-Alkenylboronic Acids Including the Unprecedented 1-Alkoxycarbonyl Derivatives," 2004, vol. 36 (6), pp. 573-579.
Hartwig J.F., "Electronic Effects on Reductive Elimination to Form Carbon-carbon and Carbon-heteroatom Bonds from Palladium(ii) Complexes," Inorganic Chemistry, 2007, vol. 46 (6), pp. 1936-1947.
Hellwinkel D., "Bis(2,2'-biphenylylene)phosphorane and the Bis(2,2'-biphenylylene)phosphoranyl Radical," Angewandte Chemie International Edition, 1966, vol. 5 (11), pp. 968.
Hicks J.D., et al., "Pd-catalyzed N-arylation of Secondary Acyclic Amides: Catalyst Development, Scope, and Computational Study," Journal of the American Chemical Society, 2009, vol. 131 (46), pp. 16720-16734.
Hilfiker R., et al., "Relevance of Solid-state Properties for Pharmaceutical Products," Polymorphism, 2006, pp. 1-19.
Hocher T., et al., "Novel [2]ferrocenophanes: Syntheses, redox properties and molecular structures of [Fe{(n5-C5H4)CMe2}2PR] (R=Ph, Cy)," Polyhedron, 2005, vol. 24 (11), pp. 1340-1346.
Hogermeier J., et al., "Nine Times Fluoride can be Good for your Syntheses. Not just Cheaper: Nonafluorobutanesulfonates as Intermediates for Transition Metal-catalyzed Reactions," Advanced Synthesis & Catalysis, 2009, vol. 351 (17), pp. 2747-2763.
Huang X., et al., "Expanding Pd-Catalyzed C—N Bond-Forming Processes: the First Amidation of Aryl Sulfonates, Aqueous Amination, and Complementarity with Cu-Catalyzed Reactions," Journal of the American Chemical Society, 2003, vol. 125 (22), pp. 6653-6655.
Ikawa T., et al., "Pd-catalyzed Amidation of Aryl Chlorides Using Monodentate Biaryl Phosphine Ligands: a Kinetic, Computational, and Synthetic Investigation," Journal of the American Chemical Society, 2007, vol. 129 (43), pp. 13001-13007.
International Preliminary Report on Patentability and Written Opinion for Application No. PCT/US2008/076576, mailed on Feb. 12, 2010, 38 pages.
International Preliminary Report on Patentability and Written Opinion for Application No. PCT/US2008/076592, mailed on Mar. 24, 2010, 7 pages.
International Preliminary Report on Patentability and Written Opinion for Application No. PCT/US2008/076594, mailed on Mar. 24, 2010, 7 pages.
International Search Report and Written Opinion for Application No. PCT/US2011/044282, mailed on Dec. 5, 2011, 11 pages.
International Search Report and Written Opinion for Application No. PCT/US2013/056061, mailed on Feb. 3, 2014, 18 pages.
International Search Report for Application No. PCT/US2008/076576, mailed on Dec. 22, 2008, 4 pages.
International Search Report for Application No. PCT/US2008/076592, mailed on Feb. 16, 2009, 2 pages.
Internaitonal Search Report for Application No. PCT/US2008/076594, mailed on Dec. 30, 2008, 2 pages.
Internaitonal Search Report for Application No. PCT/US2011/044283, mailed on Jan. 30, 2012.
Jacobson M.F., et al., "Efficient N-Arylation and N-Alkenylation of the Five DNA/RNA Nucleobases," Journal of Organic Chemistry, 2006, vol. 71 (24), pp. 9183-9190.
Jiang H., et al., "Organocatalytic Preparation of Simple B-Hydroxy and B-Amino Esters: Low Catalyst Loadings and Gram-Scale Synthesis," Organic Letters, 2010, vol. 12 (21), pp. 5052-5055.
Kadyrov R., et al., "Efficient Enantioselective Synthesis of Optically Active Diols by Asymmetric Hydrogenation with Modular Chiral Metal Catalysts," Angewandte Chemie International Edition, 2009, vol. 48 (41), pp. 7556-7559.
King J.F., et al., "Tert-Butyl Cation Formation in the Hydrolysis of 2-Methyl-2-propanesulfonyl Chloride, the Simplest Tertiary Alkanesulfonyl Chloride," The Journal of Organic Chemistry, 1995, vol. 60 (9), pp. 2831-2834.
Knopfel T.F., et al., "The First Conjugate Addition Reaction of Terminal Alkynes Catalytic in Copper: Conjugate Addition of Alkynes in Water," Journal of the American Chemical Society, 2003, vol. 125 (20), pp. 6054-6055.
Koch U., et al., "2-(2-Thienyl)-5,6-dihydroxy-4-carboxypyrimidines as Inhibitors of the Hepatitis C Virus NS5B Polymerase: Discovery, SAR, Modeling, and Mutagenesis," Journal of Medicinal Chemistry, 2006, vol. 49 (5), pp. 1693-1705.
Kolesinska B., et al., "The Umpolung of Substituent Effect in Nucleophilic Aromatic Substitution. A New Approach to the Synthesis of N, N-Disubstituted Melamines (Triazine Triskelions) Under Mild Reaction Conditions," Tetrahedron, 2009, vol. 65 (18), pp. 3573-3576.
Kurz L., et al., "Stereospecific Functionalization of (R)-(−)-1,1'-BI-2.Naphthol Triflate," Tetrahedron Letters, 1990, vol. 31 (44), pp. 6321-6324.
Kuwabe S.I., et al., "Palladium-Catalyzed Intramolecular C—O Bond Formation," Journal of the American Chemical Society, 2001, vol. 123 (49), pp. 12202-12206.
Lal G.S. et al., "A Convenient Synthesis of 5-Fluoropyrimidines Using 1-(Chloromethyl)-4-fluoro-1,4-diazabicyclo[2.2.2]octane Bis(tetrafluoroborate)-SELECTFLUOR Reagent," J. Org. Chem, vol. 60 (22), pp. 7340-7342, 1995.
Li Z., et al., "Brønsted Acid Catalyzed Addition of Phenols, Carboxylic Acids, and Tosylamides to Simple Olefins," Organic Letters, 2006, vol. 8 (19), pp. 4175-4178.
Liu Z., et al., "Facile N-Arylation of Amines and Sulfonamides and O-Arylation of Phenols and Arenecarboxylic Acids," The Journal of Organic Chemistry, 2006, vol. 71 (8), pp. 3198-3209.
Lohmann V., et al., "Replication of Subgenomic Hepatitis C Virus RNAs in a Hepatoma Cell Line," Science, 1999, vol. 285 (5424), pp. 110-113.
Mann G., et al., "Carbon-Sulfur Bond-Forming Reductive Elimination Involving sp-, sp2-, and sp3-Hybridized Carbon. Mechanism, Steric Effects, and Electronic Effects on Sulfide Formation," Journal of the American Chemical Society, 1998, vol. 120 (36), pp. 9205-9219.
Marcotullio M.C., et al., "A New, Simple Synthesis of N-Tosyl Pyrrolidines and Piperidines," Synthesis, 2006, vol. 16 (16), pp. 2760-2766.
Maruyama T., et al., "A New Method for the Synthesis of N-phenyl-uracil and -pyrimidine Nucleosides," Journal of the Chemical Society, Perkin Transactions 1, 1995, pp. 733-734.
Mathe C., et al., "L-nucleoside Enantiomers as Antivirals Drugs: A Mini-review," Antiviral Research, 2006, vol. 71, pp. 276-281.
Mathew J.S., et al., "Investigations of Pd-catalyzed Arx Coupling Reactions Informed by Reaction Progress Kinetic Analysis," The Journal of Organic Chemistry, 2006, vol. 71 (13), pp. 4711-4722.
Messaoudi S., et al., "Rapid Access to 3-(N-substituted)-aminoquinolin-2(1H)-ones using Palladium-catalyzed C—N Bond Coupling Reaction," Tetrahedron, 2007, vol. 63 (41), pp. 10202-10210.
Miller M.W., et al., "Anticoccidial Activity of 1-Phenyluracils," Journal of Medicinal Chemistry, 1983, vol. 26 (7), pp. 1075-1076.
Morrison J.F., et al., "Approaches to the Study and Analysis of the Inhibition of Enzymes by Slow- and Tight-Binding Inhibitors," Comments Molecular Cellular Biophysics, 1985, vol. 2(6), pp. 347-368.
Ohira S., "Methanolysis of Dimethyl (1-Diazo-2-Oxopropyl)Phosphonate: Generation of Dimethyl(DiazoMethyl)Phosphonate and Reaction with Carbonyl Compounds," Synthetic Communications, 1989, vol. 19 (3-4), pp. 561-564.
Ohta T., et al., "Asymmetric Hydrogenation of Olefins With Aprotic Oxygen Functionalities Catalyzed by BINAP-Ru(I1) Complexes," The Journal of Organic Chemistry, 1995, vol. 60, pp. 357-363.
Onitsuka K., et al., "Living Polymerization of Bulky Aryl Isocyanide with Arylrhodium Complexes," Organometallics, 2006, vol. 25 (5), pp. 1270-1278.

(56) References Cited

OTHER PUBLICATIONS

Opposition filed by "Asociacion de Laboratorios Farmaceuticos, Alafar" received from Ecuadorian Patent Office, through Providence notified on Apr. 1, 2009, 3 pages.
Pelletier G., et al., "Copper-Catalyzed Amidation of Allylic and Benzylic C—H Bonds," Organic Letters , 2006, vol. 8 (26), pp. 6031-6034.
Pineschi M., et al., "Facile Regio- and Stereoselective Carbon-carbon Coupling of Phenol Derivatives with Aryl Aziridines," Organic Letters, 2006, vol. 8 (12), pp. 2627-2630.
Remington J.P., ed., Pharmaceutical Sciences, 15th Edition, Mack Publishing Company, 1975, pp. 411-415.
Saget T., et al., "Chiral Monodentate Phosphines and Bulky Carboxylic Acids: Cooperative Effects in Palladium-Catalyzed Enantioselective C(sp(3) )-H Functionalization," Angewandte Chemie International Edition, 2012, vol. 51 (9), pp. 2238-2242.
Saha B., et al., "Syntheses and Applications of 2-phosphino-2'-alkoxy-1,1'-binaphthyl Ligands. Development of a Working Model for Asymmetric Induction in Hydrovinylation Reactions," Journal of Organic Chemistry, 2007, vol. 72 (7), pp. 2357-2363.
Saito T., et al., "Possible Association of Beta2- and Beta3-Adrenergic Receptor Gene Polymorphisms With Susceptibility to Breast Cancer," Breast Cancer Research, 2001, vol. 3 (4), pp. 264-269.
Santana L., et al., "A Slightly Shorter Route to Carbocyclic Nucleosides. Synthesis of (±)-trans-I [2-(Hydroxymethyl)cyclopentylmethyl]uracil," Journal of Heterocyclic Chemistry, 1999, vol. 36, pp. 293-295.
Sasaki S., et al., "Synthesis, Structure, and Redox Properties of the Extremely Crowded Triarylpnictogens: Tris(2,4,6-triisopropylphenyl)phosphine, Arsine, Stibine, and Bismuthine," Tetrahedron Letters, 2004, vol. 45 (50), pp. 9193-9196.
Scozzafava A., et al., "Anticancer and Antiviral Sulfonamides," Current Medicinal Chemistry, 2003, vol. 10 (11), pp. 925-953.
Shah S., et al., "Three Different Fates for Phosphinidenes Generated by Photocleavage of Phospha-Wittig Reagents Arp=PMe3," Journal of the American Chemical Society, 2001, vol. 123 (28), pp. 6925-6926.
Shekhar S., et al., "A General Method for Palladium-catalyzed Reactions of Primary Sulfonamides with Aryl Nonaflates," Journal of Organic Chemistry, 2011, vol. 76 (11), pp. 4552-4563.
Shekhar S., et al., A General Method for Pd-Catalyzed Reactions of Primary Sulfonamides with Aryl Nonaflates, Supporting Information, Table of Contents.
Shen Q., et al., "Lewis Acid Acceleration of C—n Bond-forming Reductive Elimination from Heteroarylpalladium Complexes and Catalytic Amidation of Heteroaryl Bromides," Journal of the American Chemical Society, 2007, vol. 129 (25), pp. 7734-7735.
Shirakawa E., et al., "Reduction of Alkynes into 1,2-dideuterioalkenes with Hexamethyldisilane and Deuterium Oxide in the Presence of a Palladium Catalyst," Chemical Communications, 2005, pp. 5885-5886.
Supplementary International Search Report for Application No. PCT/US2008/076576, mailed on Jan. 14, 2010, 2 pages.
Suzuki A., "Recent Advances in the Cross-Coupling Reactions of Organoboron Derivates with Organic Electrophiles, 1995-1998," Journal of Organometallic Chemistry, 1999, vol. 576, pp. 147-168.
Taylor W.P., et al., "Quiescent Affinity Inactivators of Protein Tyrosine Phosphatases," Bioorganic & Medicinal Chemistry, 1996, vol. 4 (9), pp. 1515-1520.
Tschan M.J., et al., "Efficient Bulky Phosphines for the Selective Telomerization of 1,3-Butadiene with Methanol," Journal of the American Chemical Society, 2010, vol. 132 (18), pp. 6463-6473.

Ueki H., et al., "Efficient Large-Scale Synthesis of Picolinic Acid-Derived Nickel(II) Complexes of Glycine," European Journal of Organic Chemistry, 2003, vol. 2003 (10), pp. 1954-1957.
Ueno Y., et al., "Synthesis and Properties of Nucleic Acid Analogues Consisting of a Benzene-Phosphate Backbone," Journal of Organic Chemistry, 2005, vol. 70 (20), pp. 7925-7935.
Van Aller R.T., et al., "A Study of Aliphatic Sulfonyl Compounds. VIII. The Thermal Decomposition of Trimethylmethanesulfonyl Chloride," The Journal of Organic Chemistry, 1966, vol. 31 (7), pp. 2357-2365.
Voituriez A., et al., "2-Phospha[3]ferrocenophanes with Planar Chirality: Synthesis and Use in Enantioselective Organocatalytic [3+2] Cyclizations," Journal of the American Chemical Society, 2008, vol. 130 (43), pp. 14030-14031.
Wallace D.J., et al., "Palladium-catalyzed Amidation of Enol Triflates: a New Synthesis of Enamides," Organic Letters, 2003, vol. 5 (24), pp. 4749-4752.
Wang Z., et al., "FeCl2-Catalyzed Aminobromination of Alkenes Using Amides or Sulfonamides and NBS as the Nitrogen and Bromine Sources," Synlett, 2008, vol. 17, pp. 2667-2668.
Widenhoefer R.A., et al., "Electronic Dependence of C—O Reductive Elimination from Palladium (Aryl)neopentoxide Complexes," Journal of the American Chemical Society , 1998, vol. 120 (26), pp. 6504-6511.
Widhalm M., et al., "Rigid P-Chiral Mono and Diphosphines. Configurative Stability and P-Inversion Barrier," Tetrahedron: Asymmetry, 2006, vol. 17 (9), pp. 1355-1369.
Willis M.C., et al., "Palladium-Catalyzed Tandem Alkenyl and Aryl C—N Bond Formation: A Cascade N-Annulation Route to 1-Functionalized Indoles," Angewandte Chemie International Edition, 2005, vol. 44 (3), pp. 403-406.
Written Opinion for Application No. PCT/US2011/044283, mailed on Jan. 16, 2013, 7 pages.
Yamashita M., et al., "Trans Influence on the Rate of Reductive Elimination. Reductive Elimination of Amines from Isomeric Arylpalladium Amides with Unsymmetrical Coordination Spheres," Journal of the American Chemical Society, 2003 , vol. 125 (52), pp. 16347-16360.
Yang., et al., Synlett, 2009, pp. 1167-1171.
Yin J., et al., "Palladium-catalyzed Intermolecular Coupling of Aryl Halides and Amides," Organic Letters, 2000, vol. 2 (8), pp. 1101-1104.
Yin J., et al., "Pd-Catalyzed Intermolecular Amidation of Aryl Halides. The Discovery that Xantphos Can be Trans-Chelating in a Palladium Complex," Journal of the American Chemical Society, vol. 124, pp. 6043-6048.
Zhang J., et al., "Gold(I)-Catalyzed Intra- and Intermolecular Hydroamination of Unactivated Olefins," Journal of the American Chemical Society , 2006, vol. 128 (6), pp. 1798-1799.
Zhou T., et al., "Hypervalent Iodine in Synthesis: Part 86. Selective Copper-catalyzed N-monoarylation and N1, N3 Diarylation of Uracil and its Derivatives with Diaryliodonium Salts," Helvetica Chimica Acta, 2005, vol. 88 (2), pp. 290-296.
Herrbach A. et al., "Asymmetric Synthesis of an Axially Chiral Antimitotic Biaryl via an Atropo-Enantioselective Suzuki Cross-Coupling," Journal of Organic Chem., 2003, 68(12), pp. 4897-4905.
Li W. et al., "3,4-Disubstituted benzofuran P1' MMP-13 inhibitors: Optimization of selectivity and reduction of protein binding," Bioorg. Med. Chem. Lett., 2009, 19, pp. 4546-4550.
Suwandi L.S. et al., "Synthesis and antitumor activities of 3-modified 2-methoxyestradiol analogs," Bioorg. Med. Chem. Lett., 2009, 19, pp. 6459-6462.
Rosen et al., "Mild Pd-Catalyzed N-Arylation of Methanesulfonamide and Related Nucleophiles: Avoiding Potentially Genotoxic Reagents and Byproducts," Org. Lett. 13(10):2564-2567 (2011).

* cited by examiner

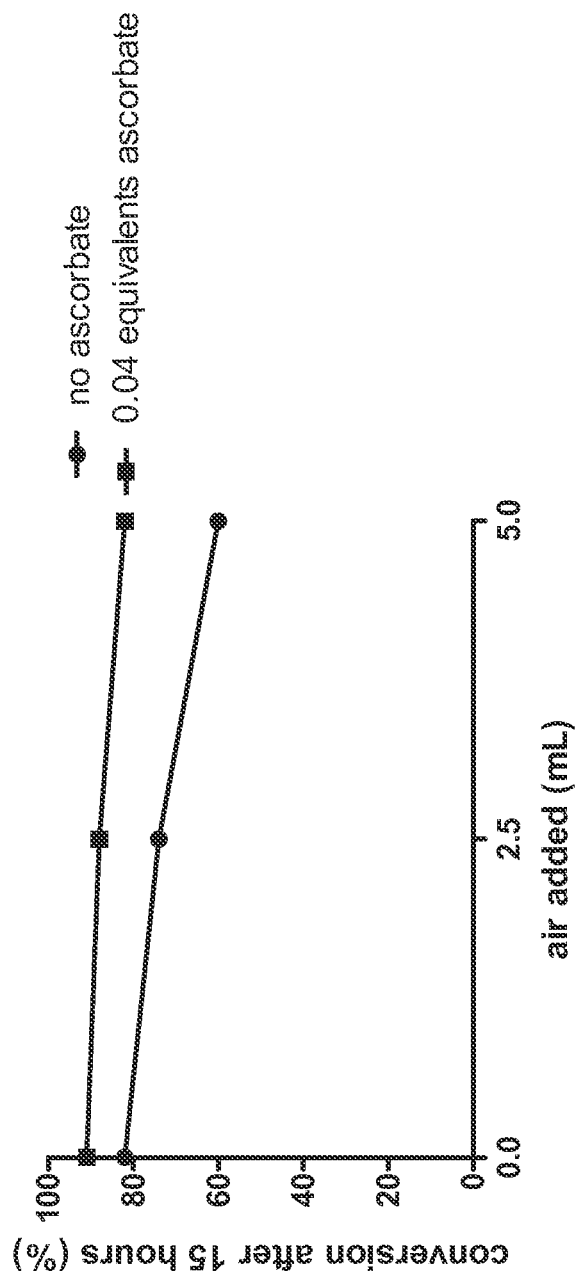

PROCESS FOR PREPARING ANTIVIRAL COMPOUNDS

CROSS-REFERENCE TO RELATED APPLICATIONS

This application is a divisional of U.S. patent application Ser. No. 13/591,090, filed Aug. 21, 2012, which is a continuation-in-part of U.S. application Ser. No. 13/184,440, filed Jul. 15, 2011, which claims priority to U.S. Provisional Application No. 61/444,475 filed Feb. 18, 2011 and U.S. Provisional Application No. 61/365,293 filed Jul. 16, 2010, the entire contents of which are incorporated herein by reference.

TECHNICAL FIELD

This disclosure is directed to: (a) processes for preparing a compound and salts thereof that, inter alia, are useful for inhibiting hepatitis C virus (HCV); (b) intermediates useful for the preparation of the compound and salts; (c) pharmaceutical compositions comprising the compound or salts; and (d) methods of use of such compositions.

BACKGROUND

Hepatitis C is a blood-borne, infectious, viral disease that is caused by a hepatotropic virus called HCV. At least six different HCV genotypes (with several subtypes within each genotype) are known to date. In North America, HCV genotype 1a predominates, followed by HCV genotypes 1b, 2a, 2b, and 3a. In the United States, HCV genotypes 1, 2, and 3 are the most common, with about 80% of the hepatitis C patients having HCV genotype 1. In Europe, HCV genotype 1b is predominant, followed by HCV genotypes 2a, 2b, 2c, and 3a. HCV genotypes 4 and 5 are found almost exclusively in Africa. As discussed below, the patient's HCV genotype is clinically important in determining the patient's potential response to therapy and the required duration of such therapy.

An HCV infection can cause liver inflammation (hepatitis) that is often asymptomatic, but ensuing chronic hepatitis can result in cirrhosis of the liver (fibrotic scarring of the liver), liver cancer, and/or liver failure. The World Health Organization estimates that about 170 million persons worldwide are chronically infected with HCV, and from about three to about four million persons are newly infected globally each year. According to the Centers for Disease Control and Prevention, about four million people in the United States are infected with HCV. Co-infection with the human immunodeficiency virus (HIV) is common, and rates of HCV infection among HIV positive populations are higher.

There is a small chance of clearing the virus spontaneously, but the majority of patients with chronic hepatitis C will not clear it without treatment. Indications for treatment typically include proven HCV infection and persistent abnormal liver function tests. There are two treatment regimens that are primarily used to treat hepatitis C: monotherapy (using an interferon agent—either a "conventional" or longer-acting pegylated interferon) and combination therapy (using an interferon agent and ribavirin). Interferon, which is injected into the bloodstream, works by bolstering the immune response to HCV; and ribavirin, which is taken orally, is believed to work by preventing HCV replication. Taken alone, ribavirin does not effectively suppress HCV levels, but an interferon/ribavirin combination is more effective than interferon alone. Typically, hepatitis C is treated with a combination of pegylated interferon alpha and ribavirin for a period of 24 or 48 weeks, depending on the HCV genotype.

The goal of treatment is sustained viral response—meaning that HCV is not measurable in the blood after therapy is completed.

Treatment may be physically demanding, particularly for those with prior history of drug or alcohol abuse, because both interferon and ribavirin have numerous side effects. Common interferon-associated side effects include flu-like symptoms, extreme fatigue, nausea, loss of appetite, thyroid problems, high blood sugar, hair loss, and skin reactions at the injection site. Possible serious interferon-associated side effects include psychoses (e.g., suicidal behavior), heart problems (e.g., heart attack, low blood pressure), other internal organ damage, blood problems (e.g., blood counts falling dangerously low), and new or worsening autoimmune disease (e.g., rheumatoid arthritis). Ribavirin-associated side effects include anemia, fatigue, irritability, skin rash, nasal stuffiness, sinusitis, and cough. Ribavirin can also cause birth defects, so pregnancy in female patients and female partners of male patients must be avoided during treatment and for six months afterward.

Some patients do not complete treatment because of the serious side effects discussed above; other patients (non-responders) continue to have measurable HCV levels despite treatment; and yet other patients (relapsers) appear to clear the virus during therapy, but the virus returns sometime after completion of the treatment regimen. Thus, there continues to be a need for alternative compositions and methods of treatment (used either in combination with, or in lieu of, an interferon agent and/or ribavirin) to prevent the progression of liver damage from hepatitis C.

SUMMARY

This disclosure is directed to processes for preparing compounds of formula (A)

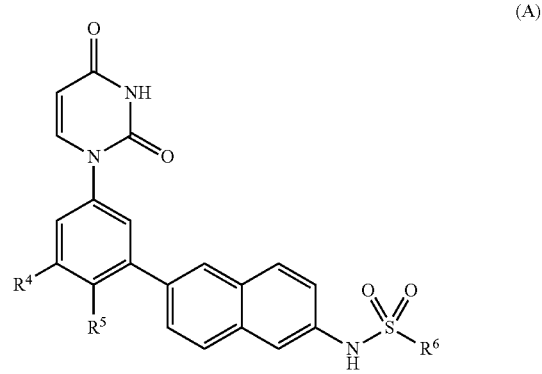

(A)

This disclosure is also directed to processes for preparing compounds such as N-(6-(3-tert-butyl-5-(2,4-dioxo-3,4-dihydropyrimidin-1(2H)-yl)-2-methoxyphenyl)naphthalen-2-yl)methanesulfonamide (compound (A-1)) or a salt thereof, wherein the process comprises sulfonamidation of a sulfonate (compound (5)).

This disclosure also is directed to compound (A) and salts thereof prepared by the processes described herein.

This disclosure also is directed to compound (A) and potassium or sodium salts thereof prepared by the processes described herein.

This disclosure also is directed to a process for preparing compound (5).

This disclosure also is directed to compound (4).

This disclosure also is directed to various intermediates useful for preparing compound (4) as well as to processes for preparing those intermediates.

This disclosure also is directed to intermediate compounds (1) and (3) useful for preparing compound (4) as well as to processes for preparing those intermediates.

This disclosure also is directed to compositions (including pharmaceutical compositions) that comprise compound (A) or salt thereof that are prepared by the above processes. Optionally, the compositions can comprise one or more additional therapeutic agents.

This disclosure also is directed to methods of use of the above compounds and compositions to, for example, inhibit replication of a ribonucleic acid (RNA) virus (including HCV) or treat a disease treatable by inhibiting HCV RNA polymerase (including hepatitis C).

Further benefits of this disclosure will be apparent to one skilled in the art.

BRIEF DESCRIPTION OF FIGURE

FIG. 1 is a graph illustrating the effect of air and sodium ascorbate on the coupling of 1-tert-butyl-3,5-diiodo-2-methoxybenzene and N-(2-cyanophenyl)benzamide to form 1-(3-tert-butyl-5-iodo-4-methoxyphenyl)pyrimidine-2,4(1H,3H)-dione-compound (1c).

DETAILED DESCRIPTION

This detailed description is intended only to acquaint others skilled in the art with this disclosure, its principles, and its practical application so that others skilled in the art may adapt and apply the disclosure in its numerous forms, as they may be best suited to the requirements of a particular use. This description and its specific examples are intended for purposes of illustration only. This disclosure, therefore, is not limited to the embodiments described in this patent application, and may be variously modified.

This disclosure is directed, in part, to processes for preparing compounds of formula (A) such as N-(6-(3-tert-butyl-5-(2,4-dioxo-3,4-dihydropyrimidin-1(2H)-yl)-2-methoxyphenyl)naphthalen-2-yl)methanesulfonamide (compound (A-1)) or a salt thereof. The salt of compound (A) may be the potassium salt, the sodium salt or any other suitable salt. In embodiments, the salt of compound (A) is the potassium salt. In embodiments, the salt of compound (A) is the sodium salt.

The process comprises sulfonamidation of compound (5), wherein $LG^1$ is a leaving group; $R^4$ is selected from the group consisting of $C_1$-$C_6$-alkyl, $C_1$-$C_6$-fluoroalkyl, $C_1$-$C_6$-hydroxyalkyl, phenyl, 2-thienyl, 3-thienyl, 2-furanyl, and 3-furanyl; $R^5$ is selected from the group consisting of hydrogen, fluoro, chloro, $C_1$-$C_6$-alkyl, and $C_1$-$C_6$-alkyloxy; and $R^6$ is selected from the group consisting of $C_1$-$C_6$-alkyl and $C_1$-$C_6$-fluoroalkyl.

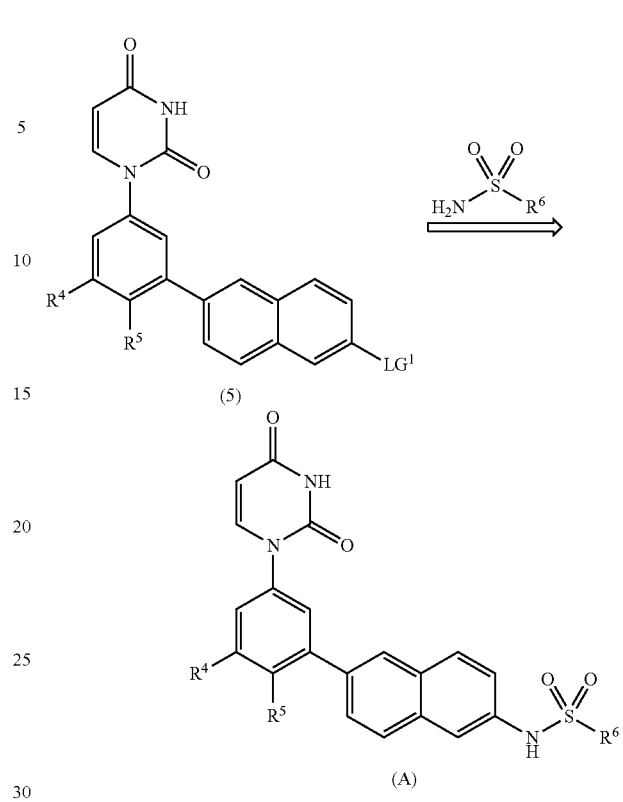

In embodiments, $LG^1$ is selected from the group consisting of chloro, bromo, iodo and —$OSO_2R^{1a}$, wherein $R^{1a}$ is selected from the group consisting of aryl, alkyl, fluoroalkyl, -fluoroalkyl-O-fluoroalkyl, —N(alkyl)$_2$, —O(alkyl), —O(aryl), fluoro, imidazolyl, and isomers and homologs thereof.

In embodiments, $LG^1$ is —$OSO_2R^{1a}$, wherein $R^{1a}$ is aryl, such asp-tolyl or phenyl; alkyl such as methyl or ethyl; fluoroalkyl such as trifluoromethyl, perfluorobutyl ($C_4F_9$), or isomers of perfluorobutyl and other higher and lower homologs such as, but not limited to, perfluoropentyl, perfluorohexyl, and perfluorooctyl. In embodiments, $R^{1a}$ is -fluoroalkyl-O-fluoroalkyl such as perfluoroethoxyethyl; —N(alkyl)$_2$; fluoro; or imidazolyl.

Process for Preparing compounds of formula (A) such as N-(6-(3-tert-butyl-5-(2,4-dioxo-3,4-dihydro-pyrimidin-1(2H)-yl)-2-methoxyphenyl)naphthalen-2-yl)methanesulfonamide (compound (A-1)) and the corresponding salt

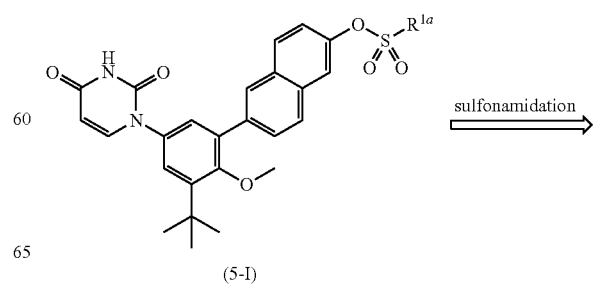

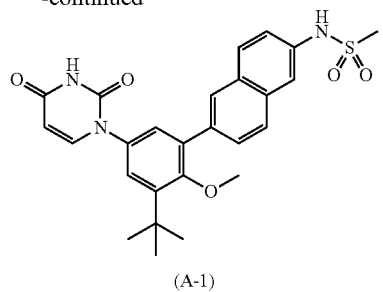

(A-1)

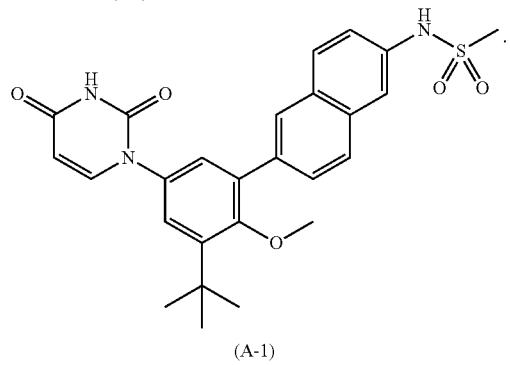

(5-1) sulfonamidation

In an embodiment, the process comprises sulfonamidation of 6-(3-tert-butyl-5-(2,4-dioxo-3,4-dihydropyrimidin-1 (2H)-yl)-2-methoxyphenyl)naphthalen-2-yl nonafluorobutane-1-sulfonate (compound (5-1)) selected from the group consisting of 6-(3-tert-butyl-5-(2,4-dioxo-3,4-dihydropyrimidin-1(2H)-yl)-2-methoxyphenyl)naphthalen-2-yl 1,1,2,2,3,3,4,4,4-nonafluorobutane-1-sulfonate, 6-(3-tert-butyl-5-(2,4-dioxo-3,4-dihydropyrimidin-1(2H)-yl)-2-methoxyphenyl)naphthalen-2-yl 1,1,1,2,3,3,4,4,4-nonafluorobutane-2-sulfonate, 6-(3-tert-butyl-5-(2,4-dioxo-3,4-dihydropyrimidin-1(2H)-yl)-2-methoxyphenyl) naphthalen-2-yl 1,1,2,3,3,3-hexafluoro-2-(trifluoromethyl)propane-1-sulfonate, and 6-(3-tert-butyl-5-(2,4-dioxo-3,4-dihydropyrimidin-1(2H)-yl)-2-methoxyphenyl)naphthalen-2-yl 1,1,1,3,3,3-hexafluoro-2-(trifluoromethyl)propane-2-sulfonate.

(A-1)

In an embodiment, the process comprises sulfonamidation of 6-(3-tert-butyl-5-(2,4-dioxo-3,4-dihydropyrimidin-1 (2H)-yl)-2-methoxyphenyl)naphthalen-2-yl 1,1,2,2,3,3,4,4,4-nonafluorobutane-1-sulfonate (compound (5a)).

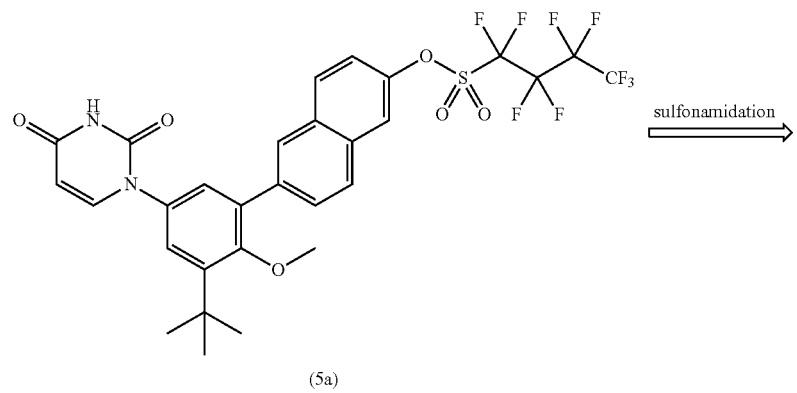

(5a) sulfonamidation

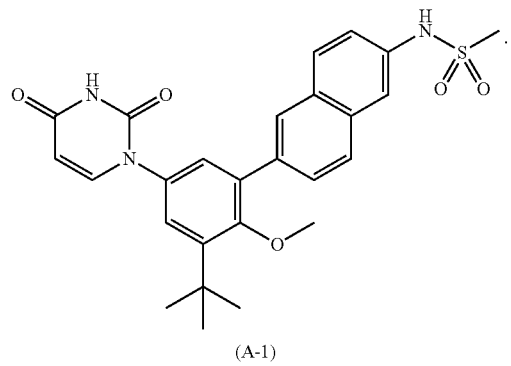

(A-1)

Compound (5) may be sulfonamidated using a transition metal catalyst or a transition metal catalyst precursor and ligand.

In embodiments, the ligand has a structure corresponding to the structure of formula (I),

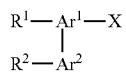
(I)

wherein X is a cyclic or acyclic phosphine.

Ar¹ and Ar² are each independently aryl or heteroaryl. Examples of the Ar¹-Ar² group are given in formulae (I-1)-(I-42)

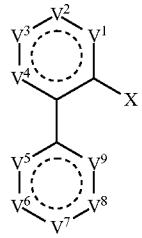
(I-1)

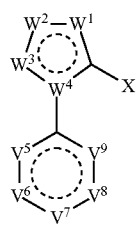
(I-2)

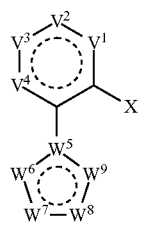
(I-3)

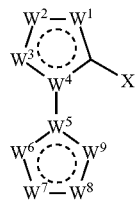
(I-4)

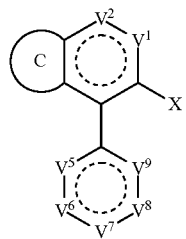
(I-5)

-continued

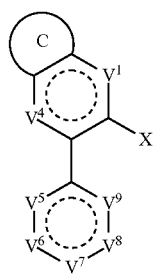
(I-6)

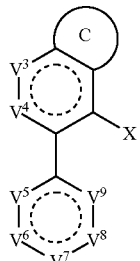
(I-7)

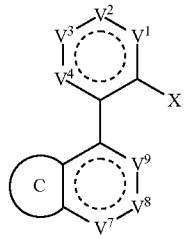
(I-8)

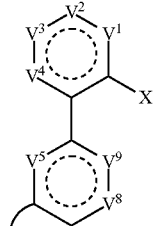
(I-9)

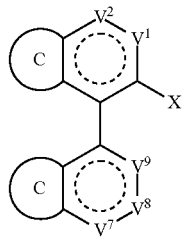
(I-10)

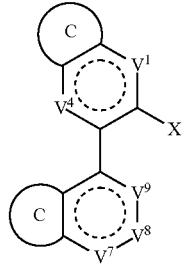
(I-11)

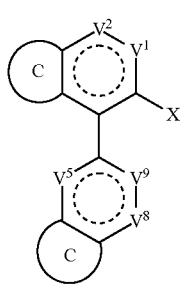 (I-12)
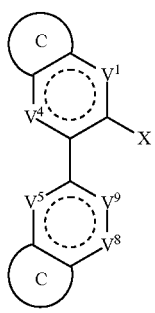 (I-13)
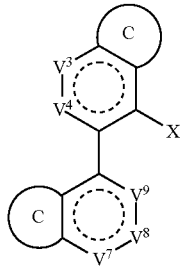 (I-14)
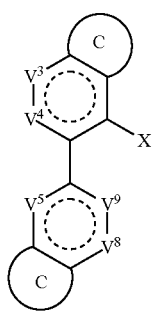 (I-15)
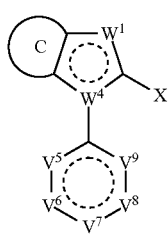 (I-16)
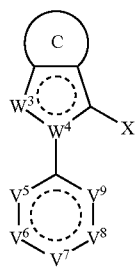 (I-17)
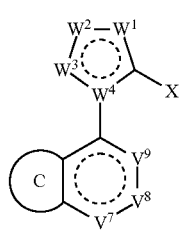 (I-18)
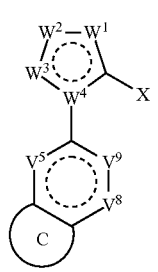 (I-19)
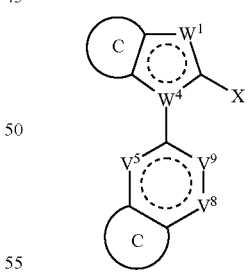 (I-20)
(I-21)
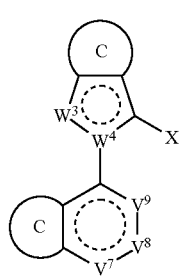 (I-22)

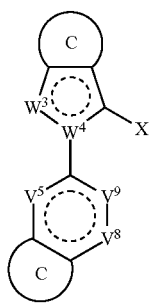 (I-23)
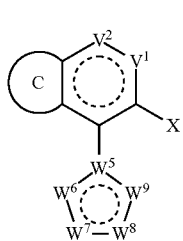 (I-24)
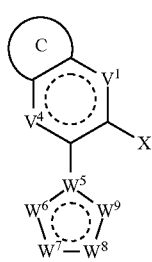 (I-25)
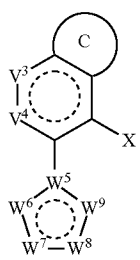 (I-26)
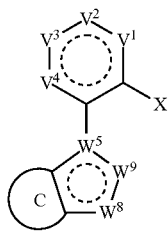 (I-27)
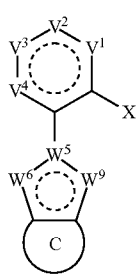 (I-28)
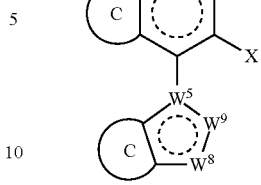 (I-29)
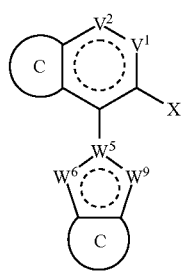 (I-30)
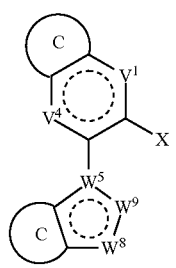 (I-31)
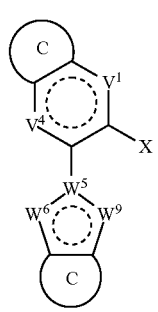 (I-32)
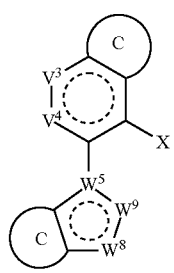 (I-33)

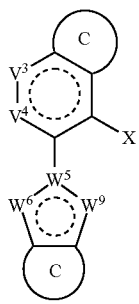
(I-34)

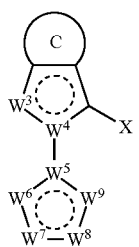
(I-35)

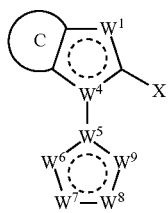
(I-36)

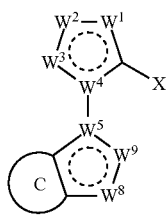
(I-37)

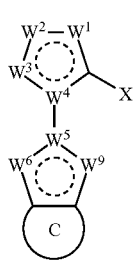
(I-38)

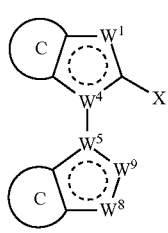
(I-39)

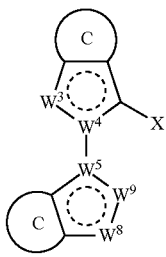
(I-40)

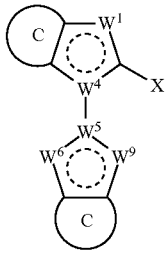
(I-41)

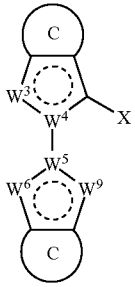
(I-42)

wherein X is a phosphine;
$V^1$, $V^2$, $V^3$, and $V^4$ are independently selected from $CR^1$ or N;
$V^5$, $V^6$, $V^7$, $V^8$ and $V^9$ are independently selected from $CR^2$ or N;
$W^1$, $W^2$, an $W^3$ are independently selected from $CR^1$, $NR^1$, N or O;
$W^4$ is C or N;
$W^5$ is C or N;
$W^6$, $W^7$, $W^8$ and $W^9$ are independently selected from $CR^2$, $NR^2$, N or O; and
ring C, at each occurrence, is independently a fused-aryl or fused-heteroaryl unsubstituted or substituted with $R^1$ and $R^2$, respectively, any number of times depending on, for example, stability and rules of valence.

indicates that the 5- or 6-membered ring is aromatic.
$Ar^1$ and $Ar^2$ are each independently optionally substituted with groups such as one or more $R^1$ and $R^2$, respectively. $Ar^1$ and $Ar^2$ independently may be substituted with $R^1$ and $R^2$, respectively, any number of times depending on, for example, stability and rules of valence. The absence of an R group in any of the formulae (I-1)-(I-42) indicates in the conventional way that the position is occupied by a hydrogen atom.

In embodiments, $R^1$ and $R^2$ are independently selected at each occurrence from the group consisting of hydrogen;

amino; hydroxyl; cyano; halo; alkyl; alkenyl; alkynyl; haloalkyl; haloalkoxy; oxoalkyl; alkoxy; alkylamino; dialkylamino; cycloalkyl optionally substituted with groups such as alkyl, alkenyl, alkynyl, alkoxy, cyano, halo, haloalkyl or haloalkoxy; cycloalkyloxy optionally substituted with groups such as alkyl, alkenyl, alkynyl, alkoxy, cyano, halo, haloalkyl or haloalkoxy; 5- or 6-membered heteroaryl optionally substituted with groups such as alkyl, alkenyl, alkynyl, alkoxy, cyano, halo, haloalkyl or haloalkoxy; phenyl optionally substituted with groups such as alkyl, alkenyl, alkynyl, alkoxy, cyano, halo, haloalkyl or haloalkoxy; hydroxyalkyl; hydroxyalkoxy; alkoxyalkyl; aminoalkyl; N-alkylaminoalkyl; N,N-dialkylaminoalkyl; N,N,N-trialkylammoniumalkyl; $L^1$-C(O)—$OR^1$, $L^1$-P(O)—$(OR^{1'})_2$, or $L^1$-S(O)$_2$—$OR^{1'}$, wherein $L^1$ is a bond or alkylene, and $R^{1'}$ is selected from the group consisting of hydrogen, alkyl and hydroxyalkyl; $L^2$-O—C(O)—$R^{2'}$, wherein $L^2$ is a bond or alkylene, and $R^{2'}$ is alkyl or hydroxyalkyl; $L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; $L^4$-$NR^{5'}$—C(O)—$R^{6'}$, wherein $L^4$ is a bond or alkylene, $R^{5'}$ is hydrogen or alkyl, and $R^{6'}$ is alkyl or hydroxyalkyl; sulfamoyl; N-(alkyl)sulfamoyl; N,N-(dialkyl) sulfamoyl; sulfonamide; sulfate; alkylthio; and thioalkyl; or an $R^1$ and an $R^2$ join together to form an alkylene or —O—(CH$_2$)$_m$—O—, wherein m is 1, 2, 3 or 4.

In embodiments, each of $R^1$ and $R^2$ substituted as shown in each of formulae (I-1)-(I-42) are independently alkyl, alkoxy, dialkylamino, haloalkyl, fluoroalkyl, or phenyl. In embodiments, the alkyl groups are $C_1$-$C_3$ alkyl, the alkoxy groups are $C_1$-$C_3$ alkoxy, and the alkyl groups of haloalkyl and fluoroalkyl are $C_1$-$C_3$ alkyl. Examples of alkyls include methyl, ethyl, and isopropyl. Examples of alkoxys include methoxy and isopropoxy. An example of a haloalkyl includes trifluoromethyl. An example of a dialkylamino includes dimethylamino.

In embodiments, X is a phosphorous containing heterocyclic ring of Formula (Ia).

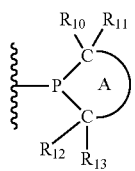

(Ia)

In these ligands, a phosphorus heterocycle labeled above as ring A (a "phosphacycle") is bonded through a phosphorus atom to a substituted aromatic ring that is, in turn, substituted with another aromatic ring at an adjacent or ortho carbon atom to the phosphacycle. The phosphacycle contains three or more ring atoms including a phosphorus atom and two ring carbons bonded directly to the phosphorus atom. Ring A may be a phosphorus monocyclic heterocyclic ring, a bicyclic heterocyclic ring, or a tricyclic heterocyclic ring. Ring A includes 0 to 9 ring atoms in addition to the phosphorus and 2 carbon ring atoms of formula (Ia). Each of the ring atoms may be independently selected from the group consisting of carbon, oxygen, nitrogen and sulfur. The two ring carbons bonded to the phosphorus atom may be bonded to substituents $R^{10}$, $R^{11}$, $R^{12}$, and $R^{13}$ through a carbon atom, i.e., substituents $R^{10}$, $R^{11}$, $R^{12}$, and $R^{13}$ may be bonded to the phosphacycle through a carbon atom of the respective substituents. The phosphacycle may optionally contain one or more ring substituents selected from the group consisting of alkenyl; alkoxy; alkoxyalkyl; alkyl; alkylamino; alkylthio; alkynyl; aminoalkyl; N-alkylaminoalkyl; N,N-dialkylaminoalkyl; N,N,N-trialkylammoniumalkyl; arylalkyl optionally substituted with groups such as alkyl, alkenyl, alkynyl, alkoxy, cyano, halo, haloalkyl or haloalkoxy; cycloalkyl optionally substituted with groups such as alkyl, alkenyl, alkynyl, alkoxy, cyano, halo, haloalkyl or haloalkoxy; dialkylamino; halo; haloalkyl; fluoroalkyl; $M_5$-$M_6$heteroaryl optionally substituted with groups such as alkyl, alkenyl, alkynyl, alkoxy, cyano, halo, haloalkyl or haloalkoxy; heterocycloalkyl optionally substituted with groups such as alkyl, alkenyl, alkynyl, alkoxy, cyano, halo, haloalkyl or haloalkoxy; hydroxy; hydroxyalkyl; oxo; an exocyclic double bond optionally substituted with groups such as alkyl, alkenyl, alkynyl, aryl, cycloalkyl, heterocyclyl, or heteroaryl; a 3- to 7-membered spiro ring containing zero, one, or two heteroatoms; phenyl optionally substituted with groups such as alkyl, alkenyl, alkynyl, alkoxy, cyano, halo, haloalkyl or haloalkoxy; $L^1$-C(O)—$OR^{1'}$, $L^1$-P(O)—$(OR^{1'})_2$, or $L^1$-S(O)$_2$—$OR^{1'}$, wherein $L^1$ is a bond or alkylene, and $R^{1'}$ is selected from the group consisting of hydrogen, alkyl and hydroxyalkyl; $L^2$-O—C(O)—$R^{2'}$, wherein $L^2$ is a bond or alkylene, and $R^{2'}$ is alkyl or hydroxyalkyl; $L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; $L^4$-$NR^{5'}$C(O)—$R^{6'}$, wherein $L^4$ is a bond or alkylene, $R^{5'}$ is hydrogen or alkyl, and $R^{6'}$ is alkyl or hydroxyalkyl; and $L^7$-$NR^{8'}$—S(O)$_2$—$R^{9'}$, wherein $L^7$ is a bond or alkylene, $R^{8'}$ is hydrogen or alkyl, and $R^{9'}$ is alkyl or hydroxyalkyl.

In various embodiments, ring A is a 4-, 5-, 6-, 7-, or 8-membered ring containing no hetero ring atoms except the P-atom shown in Formula (Ia). Ring A may be a single ring containing no bridging atoms, or ring A may be a polycyclic ring such as a bicyclic or tricyclic ring containing bridging atoms.

In embodiments, $R^{10}$, $R^{11}$, $R^{12}$, and $R^{13}$ may each be independently selected from the group consisting of hydrogen; alkyl; alkenyl; haloalkyl; alkynyl; oxoalkyl; cycloalkyl optionally substituted with alkyl, alkenyl, alkynyl, alkoxy, cyano, halo, haloalkyl or haloalkoxy; heterocyclyl optionally substituted with groups such as alkyl, alkenyl, alkynyl, alkoxy, cyano, halo, haloalkyl or haloalkoxy; $M_5$-$M_6$heteroaryl optionally substituted with groups such as alkyl, alkenyl, alkynyl, alkoxy, cyano, halo, haloalkyl or haloalkoxy; phenyl optionally substituted with groups such as alkyl, alkenyl, alkynyl, alkoxy, cyano, halo, haloalkyl or haloalkoxy; hydroxyalkyl; alkoxyalkyl; aminoalkyl; N-alkylaminoalkyl; N,N-dialkylaminoalkyl; N,N,N-trialkylammoniumalkyl; thioalkyl; $L^{13}$-C(O)—$OR^{14'}$, $L^{13}$-P(O)—$(OR^{14'})_2$, or $L^{13}$-S(O)$_2$—$OR^{14'}$, wherein $L^{13}$ is a bond or alkylene, and $R^{14'}$ is selected from the group consisting of hydrogen, alkyl and hydroxyalkyl; $L^{15}$-O—C(O)—$R^{16'}$, wherein $L^{15}$ is alkylene and $R^{16'}$ is alkyl or hydroxyalkyl; $L^{17}$-C(O)—$NR^{18'}R^{19'}$, wherein $L^{17}$ is a bond or alkylene, and $R^{18'}$ and $R^{19'}$ are each independently selected from the group consisting of hydrogen, alkyl, and hydroxyalkyl; and $L^{20}$-$NR^{21'}$—C(O)$R^{22'}$, wherein $L^{20}$ is alkylene, $R^{21'}$ is hydrogen or alkyl, and $R^{22'}$ is alkyl or hydroxyalkyl.

In addition to the substituents defined above for $R^{10}$, $R^{11}$, $R^{12}$, and $R^{13}$, or alternatively, each of $R^{10}$, $R^{11}$, $R^{12}$, and $R^{13}$ may independently be involved in forming a ring. For example, $R^{10}$ or $R^{11}$ together with $R^{12}$ or $R^{13}$ may form a ring. $R^{10}$ and $R^{11}$ together with the carbon atom to which they are attached may form a spirocyclic ring and/or $R^{12}$ and $R^{13}$ together with the carbon atom to which they are attached may form a spirocyclic ring. One or more of $R^{10}$, $R^{11}$, $R^{12}$ and $R^{13}$ may form a ring together with a ring substituent of ring A.

In embodiments, X is a phosphorous containing heterocyclic ring of Formula (Ib).

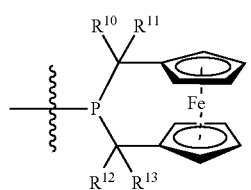

(Ib)

Phosphacycles of formula Ib are bonded through a phosphorus atom to an optionally substituted aromatic ring that is, in turn, substituted with another aromatic ring at an adjacent or ortho carbon atom to the phosphorus atom. The phosphacycle contains a ferrocenyl moiety in addition to a phosphorus atom and two ring carbons bonded directly to the phosphorus atom. The two ring carbons bonded to the phosphorus atom are in turn bonded to substituents $R^{10}$, $R^{11}$, $R^{12}$, and $R^{13}$, through a carbon atom, i.e., substituents $R^{10}$, $R^{11}$, $R^{12}$, and $R^{13}$ are bonded to the phosphacycle through a carbon atom of the respective substituents. $R^{10}$, $R^{11}$, $R^{12}$, and $R^{13}$ are as described above.

In embodiments, X is fused to $Ar^1$ to give a compound of formula (Ic):

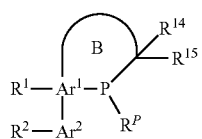

(Ic)

Ring B is a phosphorus heterocyclic ring (phosphacycle) with 0 to 5 ring atoms in addition to the phosphorus and carbon ring atom of formula (Ic). Each of the ring atoms may be independently selected from the group consisting of carbon, oxygen, nitrogen and sulfur. The phosphacycle may also optionally contain one or more ring substituents selected from the group consisting of alkenyl; alkoxy; alkoxyalkyl; alkyl; alkylamino; alkylthio; alkynyl; aminoalkyl; N-alkylaminoalkyl; N,N-dialkylaminoalkyl; N,N,N-trialkylammoniumalkyl; arylalkyl optionally substituted with groups such as alkyl, alkenyl, alkynyl, alkoxy, cyano, halo, haloalkyl or haloalkoxy; cycloalkyl optionally substituted with groups such as alkyl, alkenyl, alkynyl, alkoxy, cyano, halo, haloalkyl or haloalkoxy; dialkylamino; halo; haloalkyl; fluoroalkyl; $M_5$-$M_6$heteroaryl optionally substituted with groups such as alkyl, alkenyl, alkynyl, alkoxy, cyano, halo, haloalkyl or haloalkoxy; heterocycloalkyl optionally substituted with groups such as alkyl, alkenyl, alkynyl, alkoxy, cyano, halo, haloalkyl or haloalkoxy; hydroxy; hydroxyalkyl; oxo; an exocyclic double bond optionally substituted with groups such as alkyl, alkenyl, alkynyl, aryl, cycloalkyl, heterocyclyl, or heteroaryl; a 3- to 7-membered spiro ring containing zero, one, or two heteroatoms; phenyl optionally substituted with groups such as alkyl, alkenyl, alkynyl, alkoxy, cyano, halo, haloalkyl or haloalkoxy; $L^1$-C(O)—$OR^{1'}$, $L^1$-P(O)—$(OR^{1'})_2$, or $L^1$-S(O)$_2$—$OR^{1'}$, wherein $L^1$ is a bond or alkylene, and $R^{1'}$ is selected from the group consisting of hydrogen, alkyl or hydroxyalkyl; $L^2$-O—C(O)—$R^{2'}$, wherein $L^2$ is a bond or alkylene, and $R^{2'}$ is alkyl or hydroxyalkyl; $L^3$-C(O)—$NR^{3'}R^{4'}$, wherein $L^3$ is a bond or alkylene, and $R^{3'}$ and $R^{4'}$ are each independently selected from the group consisting of hydrogen, alkyl, and hydroxyalkyl; $L^4$-$NR^{5'}$C(O)—$R^{6'}$, wherein $L^4$ is a bond or alkylene, $R^{5'}$ is hydrogen or alkyl, and $R^{6'}$ is alkyl or hydroxyalkyl; and $L^7$-$NR^{8'}$—S(O)$_2$—$R^{9'}$, wherein $L^7$ is a bond or alkylene, $R^{8'}$ is hydrogen or alkyl, and $R^{9'}$ is alkyl or hydroxyalkyl.

$R^{14}$ and $R^{15}$, together with the carbon atom to which they are attached, may form a spirocyclic ring. One or more of $R^{14}$ and $R^{15}$ may form a ring together with a ring substituent of ring B. Each of $R^{14}$ and $R^{15}$ may be independently selected from the group consisting of hydrogen; alkyl; alkenyl; haloalkyl; alkynyl; oxoalkyl; cycloalkyl optionally substituted with groups such as alkyl, alkenyl, alkynyl, aryl, cycloalkyl, heterocyclyl, or heteroaryl; heterocyclyl optionally substituted with groups such as alkyl, alkenyl, alkynyl, alkoxy, cyano, halo, haloalkyl or haloalkoxy; $M_5$-$M_6$heteroaryl optionally substituted with groups such as alkyl, alkenyl, alkynyl, alkoxy, cyano, halo, haloalkyl or haloalkoxy; phenyl optionally substituted with groups such as alkyl, alkenyl, alkynyl, alkoxy, cyano, halo, haloalkyl or haloalkoxy; hydroxyalkyl; alkoxyalkyl; aminoalkyl; N-alkylaminoalkyl; N,N-dialkylaminoalkyl; N,N,N-trialkylammoniumalkyl; thioalkyl; $L^{13}$-C(O)—$OR^{14'}$, $L^{13}$-P(O)—$(OR^{14'})_2$, or $L^{13}$-S(O)$_2$—$OR^{14'}$ wherein $L^{13}$ is a bond or alkylene, and $R^{14'}$ is selected from the group consisting of hydrogen, alkyl and hydroxyalkyl; $L^{15}$-O—C(O)—$R^{16'}$ wherein $L^{15}$ is alkylene, and $R^{16'}$ is alkyl or hydroxyalkyl; $L^{17}$-C(O)—$NR^{18'}R^{19'}$, wherein $L^{17}$ is a bond or alkylene and $R^{18'}$ and $R^{19'}$ are each independently selected from the group consisting of hydrogen, alkyl, and hydroxyalkyl; and $L^{20}$-$NR^{21'}$—C(O)—$R^{22'}$, wherein $L^{20}$ is alkylene, $R^{21'}$ is hydrogen or alkyl, and $R^{22'}$ is alkyl or hydroxyalkyl.

$R^P$ may be selected from the group consisting of alkyl, alkenyl, alkynyl, cycloalkyl, aryl, heterocyclyl, and heteroaryl. $R^P$ may be selected from the group consisting of alkylene, alkenylene, alkynylene, or —(CR$^{41}$R$^{42}$—O)$_q$— wherein one end is attached to the phosphorus atom of the phosphacycle and the other end is attached to a B ring atom, wherein $R^{41}$ and $R^{42}$ are each independently hydrogen or alkyl, and wherein q is 1 or 2. In other words, when $R^P$ is alkylene, alkenylene, alkynylene, or —(CR$^{41}$R$^{42}$—O)$_q$—, $R^P$ may be a bridging group between the phosphorous atom of the phosphacycle and another ring atom of ring B.

In embodiments, the phosphacycle X has a structure corresponding to the structure of formula (Id):

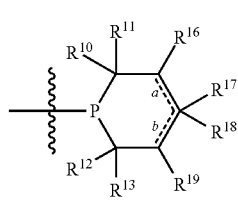

(Id)

where the groups $R^{10}$, $R^{11}$, $R^{12}$, and $R^{13}$ are as described above. The phosphacycle of formula (Id) is a six-membered ring, wherein bonds a and b are single bonds or double bonds, provided that a and b are not simultaneously double bonds. === represents a bond that is either a single or double bond.

In the phosphacycles of formula (Id), one or more of the substituents $R^{16}$, $R^{17}$, $R^{18}$, and $R^{19}$ may optionally form a ring with substituents $R^{10}$, $R^{11}$, $R^{12}$, or $R^{13}$. In addition to, or alternatively, $R^{16}$ and $R^{19}$ may be independently selected from hydrogen halo, alkyl, haloalkyl, fluoroalkyl, alkenyl, and alkoxy. In embodiments, each of $R^{16}$ and $R^{19}$ is hydrogen.

$R^{17}$ and $R^{18}$ together with the carbon atom to which they are attached may form a carbonyl; an exocyclic double bond optionally substituted with groups such as alkyl, alkenyl, alkynyl, aryl, cycloalkyl, heterocyclyl, or heteroaryl; or a 3- to 7-membered spiro ring containing zero, one, or two heteroatoms. In embodiments, the alkyl, alkenyl, alkynyl, aryl, cycloalkyl, heterocyclyl, or heteroaryl with which the exocyclic double bond is substituted, as well as the exocyclic spiro ring optionally formed by $R^{17}$ and $R^{18}$, are optionally substituted with groups such as substituents that do no interfere unacceptably with the catalytic action of the respective ligand when used in combination with transition metal compounds. In embodiments, these optional substituents are selected from those groups described for $R^1$ and $R^2$.

In addition to, or alternatively, each of $R^{17}$ and $R^{18}$ may be independently selected from moieties that do not interfere unacceptably with the catalytic action of the respective ligand when used in combination with transition metal compounds. Each of $R^{17}$ and $R^{18}$ may be independently selected from hydrogen, halo, fluoro, alkyl, alkenyl, alkynyl, haloalkyl, fluoroalkyl, alkyloxy, alkylthio, N-alkylamino, N,N-dialkylamino, substituted or unsubstituted cycloalkyl, substituted or unsubstituted heterocycloalkyl, substituted or unsubstituted $M_5$-$M_6$heteroaryl, substituted or unsubstituted phenyl; substituted or unsubstituted arylalkyl; hydroxyalkyl; alkoxyalkyl; aminoalkyl; N-alkylaminoalkyl; N,N-dialkylaminoalkyl; N,N,N-trialkylammoniumalkyl; $L^1$-C(O)—$OR^{1'}$, $L^1$-P(O)—$(OR^{1'})_2$, or $L^1$-S(O)$_2$—$OR^{1'}$ where $R^{1'}$ is hydrogen, alkyl or hydroxyalkyl and $L^1$ is a bond or alkylene; $L^2$-O—C(O)—$R^{2'}$ where $R^{2'}$ is alkyl or hydroxyalkyl and $L^2$ is a bond or alkylene; $L^3$-C(O)—$NR^{3'}R^{4'}$ where $R^{3'}$ and $R^{4'}$ are hydrogen, alkyl, or hydroxyalkyl and wherein $L^3$ is a bond or alkylene; $L^4$-$NR^5$—C(O)—$R^{6'}$ wherein $R^5$ is hydrogen or alkyl, $R^{6'}$ is alkyl or hydroxyalkyl, and $L^4$ is a bond or alkylene.

The phosphacycles may include polycyclic rings with bridging atoms.

Examples of phosphacycles having a structure corresponding to formula (Id) are as follows:

1-1

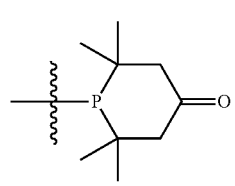

1-2

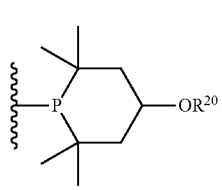

-continued 1-3

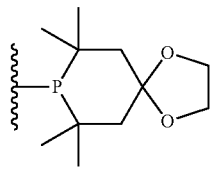

1-4

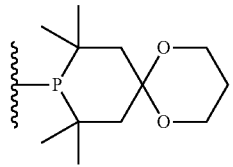

1-5

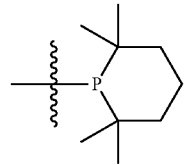

1-6

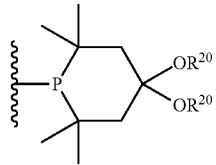

1-7

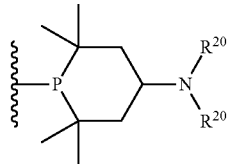

1-8

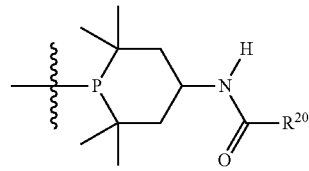

I-9

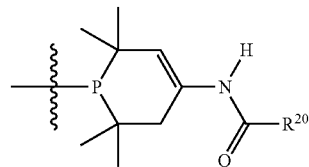

I-10

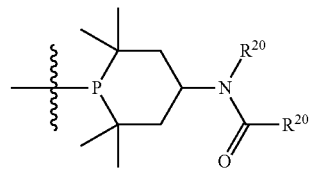

I-11

I-12
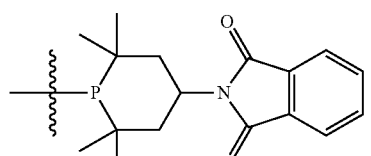
I-13
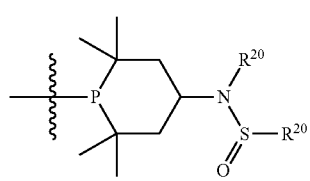
I-14
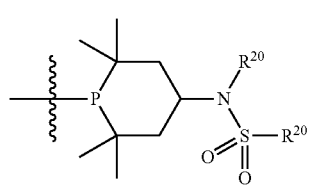
I-15
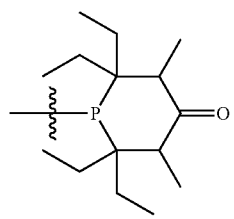
I-16
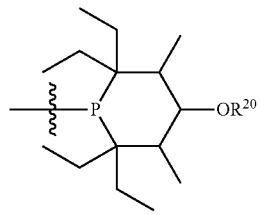
I-17
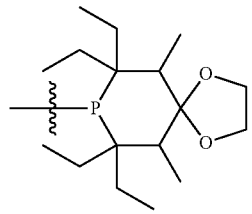
I-18
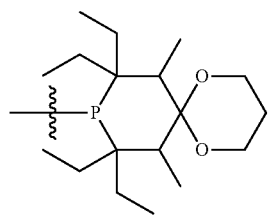
I-19
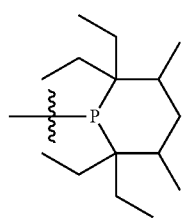
I-20
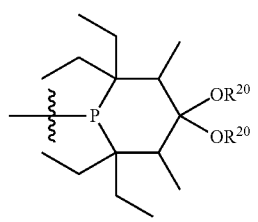
I-21
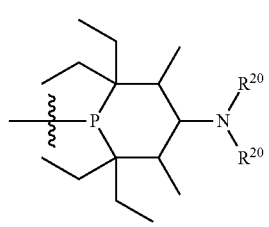
I-22
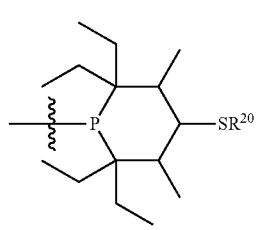
I-23
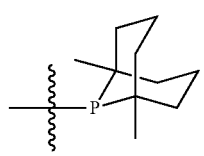
I-24
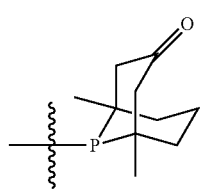
I-25
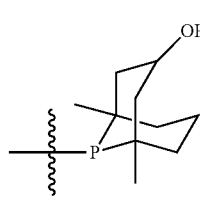

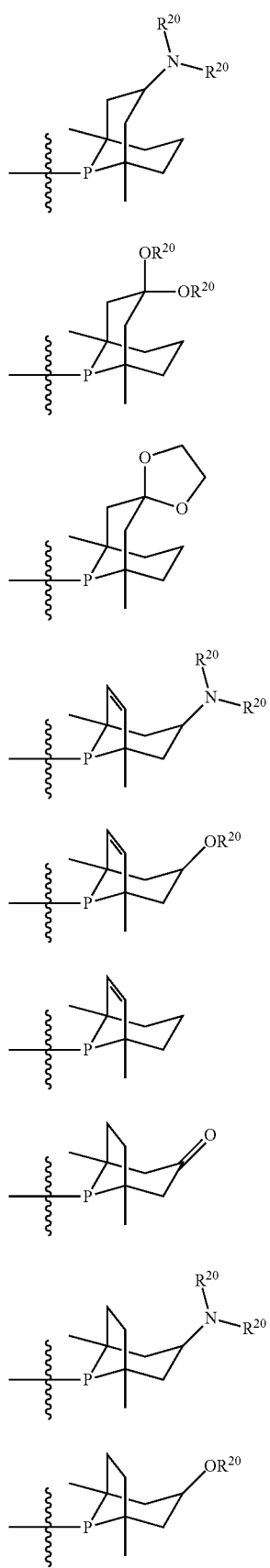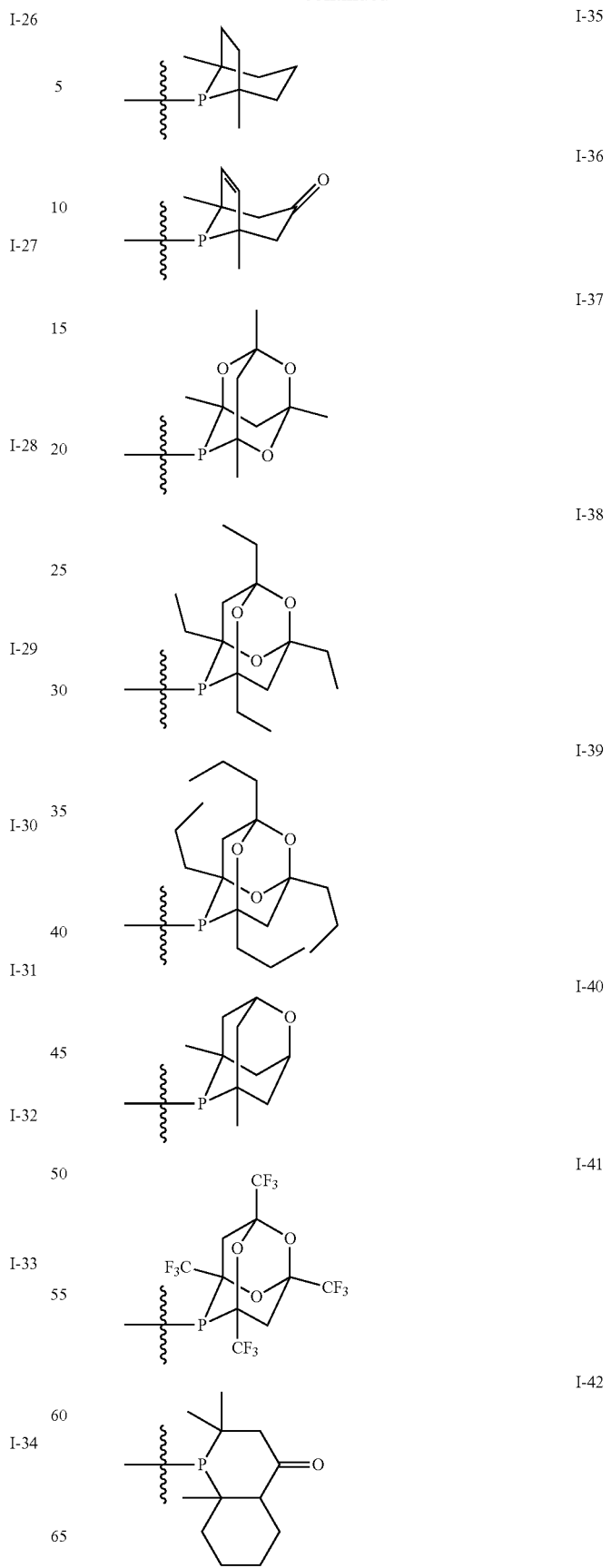

-continued
I-43 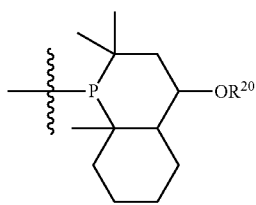
I-44 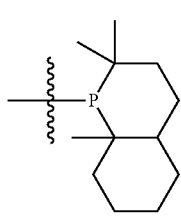
I-45 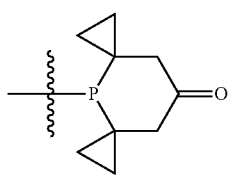
I-46 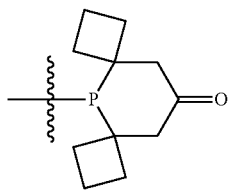
I-47 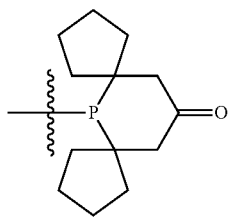
I-48 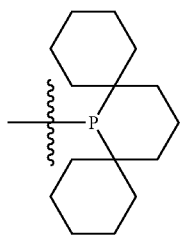
I-49 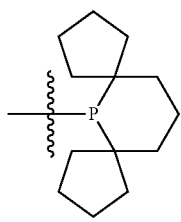
-continued
I-50 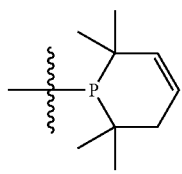
I-51 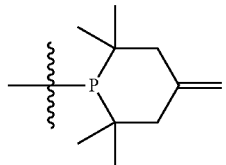
I-52 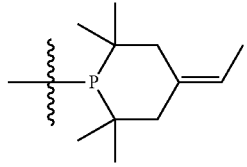
I-53 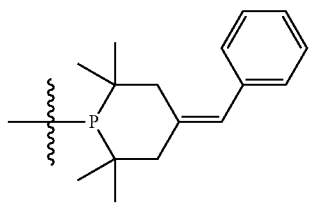
I-54 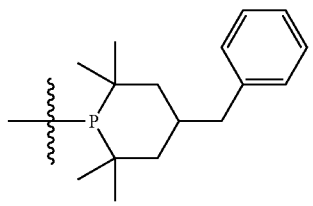
I-55 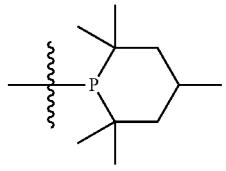
I-56 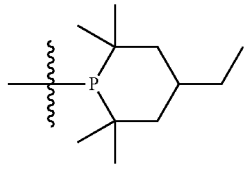
I-57 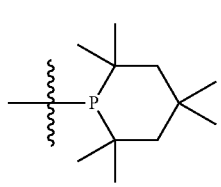

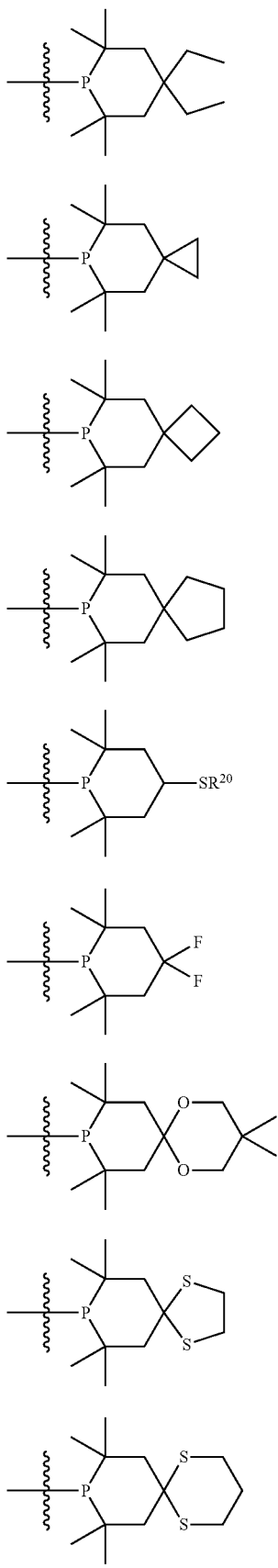

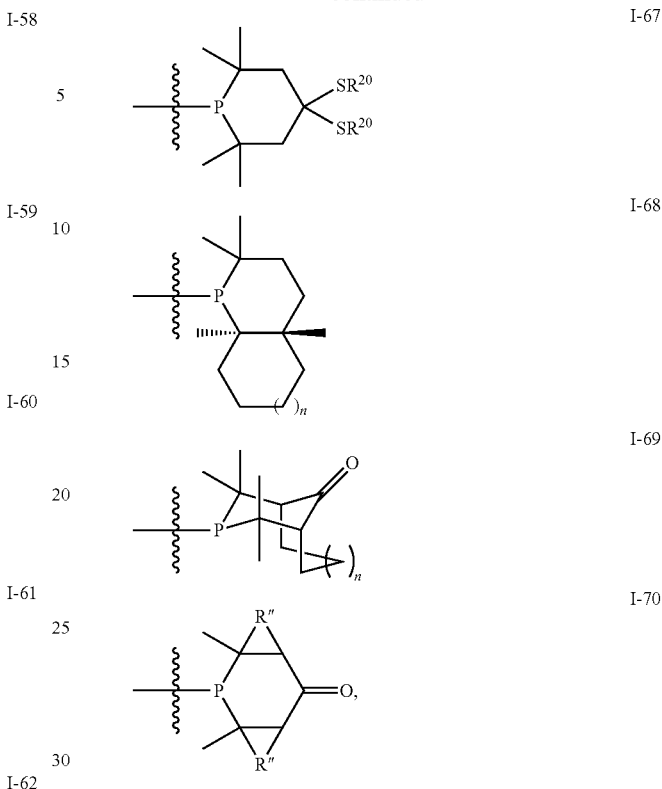

or a salt thereof, wherein R″ is selected from the group consisting of oxygen, $NR^{20}$, and $C(R^{20})_2$;

$R^{20}$ is independently, at each occurrence, hydrogen, alkyl, aryl, heteroaryl, arylalkyl or heteroarylalkyl, wherein the aryl, heteroaryl, aryl of arylalkyl and heteroaryl of heteroarylalkyl are optionally substituted with alkyl, alkenyl, alkynyl, alkoxy, cyano, halo, haloalkyl or haloalkoxy; and n is 0, 1, or 2.

The phosphacycles may have chiral centers such as, for example, phosphacycles 1-15, 1-16, 1-17, 1-18, 1-19, 1-20, 1-21, 1-22, 1-37, 1-38, 1-39, 1-41, 1-42, 1-43, 1-44, and 1-68.

In embodiments, phosphacycles X are based on rings other than a 6-membered ring. Such phosphacycles have structures corresponding to the structure of formula (Ie):

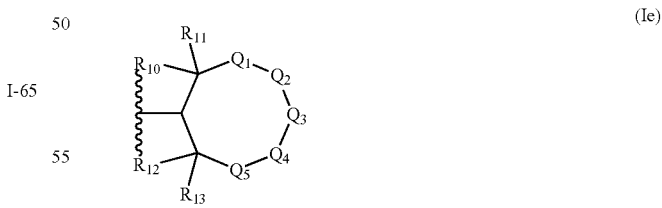

Phosphacycle X of formula (Ie) may be a 4-membered, 5-membered, 7-membered, or 8-membered ring, optionally containing bridging to form a polycyclic ring.

$Q^1$ may be a bond, —O—, —S—, —N($R^{21}$)—, =C($R^{22}$)—, or —C($R^{23}$)($R^{24}$)—; $Q^2$ may be a bond, —O—, —S—, —N($R^{25}$)—, =C($R^{26}$)—, or —C($R^{27}$)($R^{28}$)—; $Q^3$ may be a bond, —O—, —S—, —N($R^{29}$)—, =C($R^{30}$)— or —C($R^{32}$)($R^{30}$)—; $Q^4$ may be a bond, —O—, —S—, —N($R^{33}$)—, =C($R^{34}$)—, or —C($R^{35}$)($R^{36}$)—; and $Q^5$ may be a bond, —O—, —S—, —N(R$^{37}$)—, =C(R$^{38}$)—, or —C(R$^{39}$)(R$^{40}$)—; wherein R$^{10}$, R$^{11}$, R$^{12}$, R$^{13}$, and R$^{21}$ through R$^{40}$ are ring substituents. In embodiments, at least one of $Q_1$, $Q_2$, $Q_3$, $Q_4$, and $Q_5$ is not a bond, so that the phosphacycle has at least four ring members.

One or more of the ring substituents R$^{21}$ through R$^{40}$ may form a ring with another ring substituent. In addition, or alternatively, each of the ring substituents R$^{21}$ through R$^{40}$ are independently selected from hydrogen halo, fluoro, alkyl, haloalkyl, fluoroalkyl, alkenyl, alkynyl, alkyloxy, N-alkylamino, N,N-dialkylamino, N,N,N-trialkylammoniumalkyl; substituted or unsubstituted cycloalkyl, substituted or unsubstituted heterocycloalkyl, substituted or unsubstituted $M_5$-$M_6$heteroaryl, substituted or unsubstituted phenyl; hydroxyalkyl; alkoxyalkyl; aminoalkyl; N-alkylaminoalkyl; N,N-dialkylaminoalkyl; N,N,N-trialkylammoniumalkyl; L$^1$-C(O)—OR$^{1'}$, L$^1$-P(O)—(OR$^{1'}$)$_2$, or L$^1$-S(O)$_2$—OR$^{1'}$ where R$^{1'}$ is hydrogen, alkyl or hydroxyalkyl and L$^1$ is a bond or alkylene; L$^2$-O—C(O)—R$^{2'}$ where R$^{2'}$ is alkyl or hydroxyalkyl and L$^2$ is a bond or alkylene; L$^3$-C(O)—NR$^{3'}$R$^{4'}$ where R$^{3'}$ and R$^{4'}$ are each independently hydrogen, alkyl or hydroxyalkyl, and L$^3$ is a bond or alkylene; L$^4$-NR$^{5'}$C(O)—R$^{6'}$ wherein R$^{5'}$ is hydrogen or alkyl, R$^{6'}$ is alkyl or hydroxyalkyl, and L$^4$ is a bond or alkylene; and alkylthio.

In addition, or alternatively, two ring substituents on the same ring atom $Q_1$, $Q_2$, $Q_3$, $Q_4$, or $Q_5$ together may form a carbonyl; an exocyclic double bond optionally substituted with groups such as alkyl, alkenyl, aryl, cycloalkyl, heterocyclyl, or heteroaryl; or a 3- to 7-membered spiro ring containing zero, one, or two hetero ring atoms. In embodiments, the optional substituents on the exocyclic double bond or spiro ring are selected from the substituents described above for groups R$^1$ and R$^2$.

In embodiments where a phosphacycle of formula (Ie) is substituted as group X on the Ar$^1$-Ar$^2$ group of formula (I), each of R$^1$ and R$^2$ are independently selected from the group consisting of hydrogen, alkyl, aminoalkyl, and alkoxy; and each of R$^{10}$, R$^{11}$, R$^{12}$, and R$^{13}$ are independently selected from the group consisting of alkyl, aryl, and heteroaryl, and/or R$^{10}$ or R$^{11}$ together with R$^{12}$ or R$^{13}$ form a ring.

Non-limiting examples of phosphacycles of formula (Ie) are as follows:

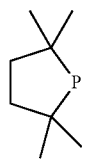

2-1

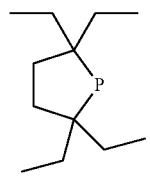

2-2

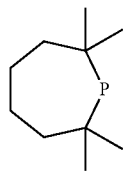

2-3

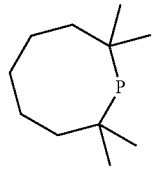

2-4

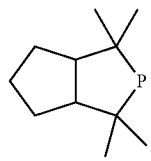

2-5

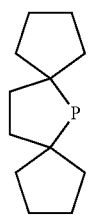

2-6

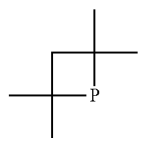

2-7

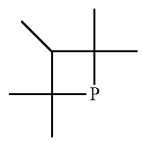

2-8

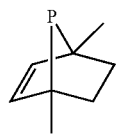

2-9

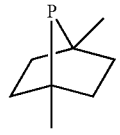

2-10

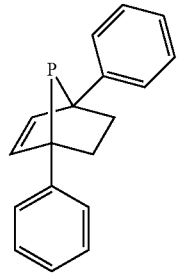

2-11

-continued

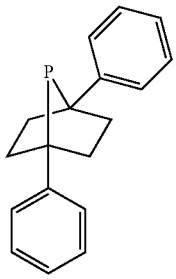

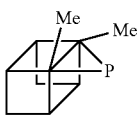

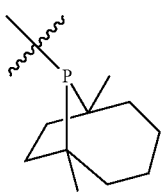

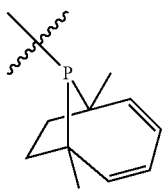

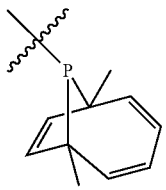

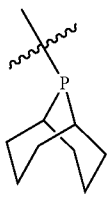

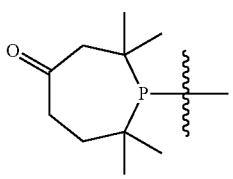

and

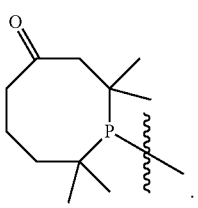

In embodiments, phosphacycles of formula (Ia), (Id), and (Ie), are substituted as group X on the $Ar^1$-$Ar^2$ group of formula (I), wherein the groups $R^1$ and $R^2$ are hydrogen or a non-hydrogen substituent.

In embodiments, X is an acyclic phosphine. In embodiments, X is a dialkyl or diaryl phosphine. In embodiments, X is —P(t-butyl)$_2$.

Phosphine ligands may include, for example, 7,7,9,9-tetramethyl-8-(2',4',6'-triisopropylbiphenyl-2-yl)-1,4-dioxa-8-phosphaspiro[4.5]decane; 2,2,6,6-tetramethyl-1-(2',4',6'-triisopropylbiphenyl-2-yl)phosphinane; 8,8,10,10-tetramethyl-9-(2',4',6'-triisopropylbiphenyl-2-yl)-1,5-dioxa-9-phosphaspiro[5.5]undecane; 2,2,6,6-tetramethyl-1-(2',4',6'-triisopropylbiphenyl-2-yl)phosphinan-4-ol; 8-(2',6'-diisopropoxybiphenyl-2-yl)-7,7,9,9-tetramethyl-1,4-dioxa-8-phosphaspiro[4.5]decane; 1,3,5,7-tetramethyl-8-(2',4',6'-triisopropylbiphenyl-2-yl)-2,4,6-trioxa-8-phosphatricyclo[3.3.1.1$^{3,7}$]decane; di-tert-butyl(2',4',6'-triisopropyl-3,4,5,6-tetramethylbiphenyl-2-yl)phosphine; di-tert-butyl(2',4',6'-triisopropylbiphenyl-2-yl)phosphine; di-tert-butyl(2'-isopropoxy-1,1'-binaphthyl-2-yl)phosphine; 2,2,5,5-tetramethyl-1-(2',4',6'-triisopropyl-3,4,5,6-tetramethylbiphenyl-2-yl)phospholane; 2,2,6,6-tetramethyl-1-(2',4',6'-triisopropyl-3,4,5,6-tetramethylbiphenyl-2-yl)phosphinane; 2,2,7,7-tetramethyl-1-(2',4',6'-triisopropyl-3,4,5,6-tetramethylbiphenyl-2-yl)phosphepane; 2,2,8,8-tetramethyl-1-(2',4',6'-triisopropyl-3,4,5,6-tetramethylbiphenyl-2-yl)phosphocane; 1,3,5,7-tetramethyl-8-phenyl-2,4,6-trioxa-8-phosphatricyclo[3.3.1.1$^{3,7}$]decane; 8-(2',6'-dimethoxybiphenyl-2-yl)-7,7,9,9-tetramethyl-1,4-dioxa-8-phosphaspiro[4.5]decane; 6-methoxy-N,N-dimethyl-2'-(7,7,9,9-tetramethyl-1,4-dioxa-8-phosphaspiro[4.5]decan-8-yl)biphenyl-2-amine; 8-(2'-methoxy-1,1'-binaphthyl-2-yl)-7,7,9,9-tetramethyl-1,4-dioxa-8-phosphaspiro[4.5]decane; 8-(1,1'-binaphthyl-2-yl)-7,7,9,9-tetramethyl-1,4-dioxa-8-phosphaspiro[4.5]decane; 7,7,9,9-tetramethyl-8-(2-(naphthalen-1-yl)phenyl)-1,4-dioxa-8-phosphaspiro[4.5]decane; 7,7,9,9-tetramethyl-8-(2-(naphthalen-2-yl)phenyl)-1,4-dioxa-8-phosphaspiro[4.5]decane; 2,2,6,6-tetramethyl-1-(2',4',6'-triisopropylbiphenyl-2-yl)phosphinan-4-one; 3,3,8,8,10,10-hexamethyl-9-(2',4',6'-triisopropylbiphenyl-2-yl)-1,5-dioxa-9-phosphaspiro[5.5]undecane; 1-(2'-(dimethylamino)-6'-methoxybiphenyl-2-yl)-2,2,6,6-tetramethylphosphinan-4-one; 1-(2',6'-bis(dimethylamino)biphenyl-2-yl)-2,2,6,6-tetramethylphosphinan-4-one; 1-(2',6'-dimethoxybiphenyl-2-yl)-2,2,6,6-tetramethylphosphinan-4-one; 1-(2',6'-diisopropoxybiphenyl-2-yl)-2,2,6,6-tetramethylphosphinan-4-one; 1-(2'-(dimethylamino)biphenyl-2-yl)-2,2,6,6-tetramethylphosphinan-4-one; 1-(biphenyl-2-yl)-2,2,6,6-tetramethylphosphinan-4-one; 1-(1,1'-binaphthyl-2-yl)-2,2,6,6-tetramethylphosphinan-4-one; 1-(2'-methoxy-1,1'-binaphthyl-2-yl)-2,2,6,6-tetramethylphosphinan-4-one; 1-(3,6-dimethoxybiphenyl-2-yl)-2,2,6,6-tetramethylphosphinan-4-one; 1-(3,6-dimethoxy-2',4',6'-trimethylbiphenyl-2-yl)-2,2,6,6-tetramethylphosphinan-4-one; 2,2,6,6-tetramethyl-1-(2',4',6'-triisopropyl-3,6-dimethoxybiphenyl-2-yl)phosphinan-4-one; 2,2,6,6-tetramethyl-1-(2',4',6'-triisopropyl-4,5-dimethoxybiphenyl-2-yl)phosphinan-4-one; 1-(3',5'-dimethoxybiphenyl-2-yl)-2,2,6,6-tetramethylphosphinan-4-one; 1-(4'-tert-butylbiphenyl-2-yl)-2,2,6,6-tetramethylphosphinan-4-one; $N^2,N^2,N^6,N^6$-tetramethyl-2'-(7,7,9,9-tetramethyl-1,4-dioxa-8-phosphaspiro[4.5]decan-8-yl)biphenyl-2,6-diamine; N,N-dimethyl-2'-(7,7,9,9-tetramethyl-1,4-dioxa-8-phosphaspiro[4.5]decan-8-yl)biphenyl-2-amine; 8-(biphenyl-2-yl)-7,7,9,9-tetramethyl-1,4-dioxa-8-phosphaspiro[4.5]decane; 8-(3,6- dimethoxybiphenyl-2-yl)-7,7,9,9-tetramethyl-1,4-dioxa-8-phosphaspiro[4.5]decane; 8-(3,6-dimethoxy-2',4',6'-trimethylbiphenyl-2-yl)-7,7,9,9-tetramethyl-1,4-dioxa-8-phosphaspiro[4.5]decane; di-tert-butyl(2',4',6'-triisopropyl-3,6-dimethoxybiphenyl-2-yl)phosphine; 7,7,9,9-tetramethyl-8-(2',4',6'-triisopropyl-3,6-dimethoxybiphenyl-2-yl)-1,4-dioxa-8-phosphaspiro[4.5]decane; or any other suitable phosphine. In embodiments, the phosphine ligand is 7,7,9,9-tetramethyl-8-(2',4',6'-triisopropylbiphenyl-2-yl)-1,4-dioxa-8-phosphaspiro[4.5]decane. In embodiments, the phosphine ligand is 2,2,6,6-tetramethyl-1-(2',4',6'-triisopropylbiphenyl-2-yl)phosphinane. In embodiments, the phosphine ligand is 8,8,10,10-tetramethyl-9-(2',4',6'-triisopropylbiphenyl-2-yl)-1,5-dioxa-9-phosphaspiro[5.5]undecane. In embodiments, the phosphine ligand is 2,2,6,6-tetramethyl-1-(2',4',6'-triisopropylbiphenyl-2-yl)phosphinan-4-ol. In embodiments, the phosphine ligand is 8-(2',6'-diisopropoxybiphenyl-2-yl)-7,7,9,9-tetramethyl-1,4-dioxa-8-phosphaspiro[4.5]decane. In embodiments, the phosphine ligand is 1,3,5,7-tetramethyl-8-(2',4',6'-triisopropylbiphenyl-2-yl)-2,4,6-trioxa-8-phosphatricyclo[3.3.1.1$^{3,7}$]decane. In embodiments, the phosphine ligand is di-tert-butyl(2',4',6'-triisopropyl-3,4,5,6-tetramethylbiphenyl-2-yl)phosphine. In embodiments, the phosphine ligand is di-tert-butyl(2',4',6'-triisopropylbiphenyl-2-yl)phosphine. In embodiments, the phosphine ligand is di-tert-butyl(2'-isopropoxy-1,1'-binaphthyl-2-yl)phosphine. In embodiments, the phosphine ligand is 2,2,5,5-tetramethyl-1-(2',4',6'-triisopropyl-3,4,5,6-tetramethylbiphenyl-2-yl)phospholane. In embodiments, the phosphine ligand is 2,2,6,6-tetramethyl-1-(2',4',6'-triisopropyl-3,4,5,6-tetramethylbiphenyl-2-yl)phosphinane. In embodiments, the phosphine ligand is 2,2,7,7-tetramethyl-1-(2',4',6'-triisopropyl-3,4,5,6-tetramethylbiphenyl-2-yl)phosphepane. In embodiments, the phosphine ligand is 2,2,8,8-tetramethyl-1-(2',4',6'-triisopropyl-3,4,5,6-tetramethylbiphenyl-2-yl)phosphocane. In embodiments, the phosphine ligand is 1,3,5,7-tetramethyl-8-phenyl-2,4,6-trioxa-8-phosphatricyclo[3.3.1.1$^{3,7}$]decane. In embodiments, the phosphine ligand is 8-(2',6'-dimethoxybiphenyl-2-yl)-7,7,9,9-tetramethyl-1,4-dioxa-8-phosphaspiro[4.5]decane. In embodiments, the phosphine ligand is 6-methoxy-N,N-dimethyl-2'-(7,7,9,9-tetramethyl-1,4-dioxa-8-phosphaspiro[4.5]decan-8-yl)biphenyl-2-amine. In embodiments, the phosphine ligand is 8-(2'-methoxy-1,1'-binaphthyl-2-yl)-7,7,9,9-tetramethyl-1,4-dioxa-8-phosphaspiro[4.5]decane. In embodiments, the phosphine ligand is 8-(1,1'-binaphthyl-2-yl)-7,7,9,9-tetramethyl-1,4-dioxa-8-phosphaspiro[4.5]decane. In embodiments, the phosphine ligand is 7,7,9,9-tetramethyl-8-(2-(naphthalen-1-yl)phenyl)-1,4-dioxa-8-phosphaspiro[4.5]decane. In embodiments, the phosphine ligand is 7,7,9,9-tetramethyl-8-(2-(naphthalen-2-yl)phenyl)-1,4-dioxa-8-phosphaspiro[4.5]decane. In embodiments, the phosphine ligand is 2,2,6,6-tetramethyl-1-(2',4',6'-triisopropylbiphenyl-2-yl)phosphinan-4-one. In embodiments, the phosphine ligand is 3,3,8,8,10,10-hexamethyl-9-(2',4',6'-triisopropylbiphenyl-2-yl)-1,5-dioxa-9-phosphaspiro[5.5]undecane. In embodiments, the phosphine ligand is 1-(2'-(dimethylamino)-6'-methoxybiphenyl-2-yl)-2,2,6,6-tetramethylphosphinan-4-one. In embodiments, the phosphine ligand is 1-(2',6'-bis(dimethylamino)biphenyl-2-yl)-2,2,6,6-tetramethylphosphinan-4-one. In embodiments, the phosphine ligand is 1-(2',6'-dimethoxybiphenyl-2-yl)-2,2,6,6-tetramethylphosphinan-4-one. In embodiments, the phosphine ligand is 1-(2',6'-diisopropoxybiphenyl-2-yl)-2,2,6,6-tetramethylphosphinan-4-one. In embodiments, the phosphine ligand is 1-(2'-(dimethylamino)biphenyl-2-yl)-2,2,6,6-tetramethylphosphinan-4-one. In embodiments, the phosphine ligand is 1-(biphenyl-2-yl)-2,2,6,6-tetramethylphosphinan-4-one. In embodiments, the phosphine ligand is 1-(1,1'-binaphthyl-2-yl)-2,2,6,6-tetramethylphosphinan-4-one. In embodiments, the phosphine ligand is 1-(2'-methoxy-1,1'-binaphthyl-2-yl)-2,2,6,6-tetramethylphosphinan-4-one. In embodiments, the phosphine ligand is 1-(3,6-dimethoxybiphenyl-2-yl)-2,2,6,6-tetramethylphosphinan-4-one. In embodiments, the phosphine ligand is 1-(3,6-dimethoxy-2',4',6'-trimethylbiphenyl-2-yl)-2,2,6,6-tetramethylphosphinan-4-one; 2,2,6,6-tetramethyl-1-(2',4',6'-triisopropyl-3,6-dimethoxybiphenyl-2-yl)phosphinan-4-one. In embodiments, the phosphine ligand is 2,2,6,6-tetramethyl-1-(2',4',6'-triisopropyl-4,5-dimethoxybiphenyl-2-yl)phosphinan-4-one; 1-(3',5'-dimethoxybiphenyl-2-yl)-2,2,6,6-tetramethylphosphinan-4-one. In embodiments, the phosphine ligand is 1-(4'-tert-butylbiphenyl-2-yl)-2,2,6,6-tetramethylphosphinan-4-one. In embodiments, the phosphine ligand is $N^2,N^2,N^6,N^6$-tetramethyl-2'-(7,7,9,9-tetramethyl-1,4-dioxa-8-phosphaspiro[4.5]decan-8-yl)biphenyl-2,6-diamine. In embodiments, the phosphine ligand is N,N-dimethyl-2'-(7,7,9,9-tetramethyl-1,4-dioxa-8-phosphaspiro[4.5]decan-8-yl)biphenyl-2-amine. In embodiments, the phosphine ligand is 8-(biphenyl-2-yl)-7,7,9,9-tetramethyl-1,4-dioxa-8-phosphaspiro[4.5]decane. In embodiments, the phosphine ligand is 8-(3,6-dimethoxybiphenyl-2-yl)-7,7,9,9-tetramethyl-1,4-dioxa-8-phosphaspiro[4.5]decane. In embodiments, the phosphine ligand is 8-(3,6-dimethoxy-2',4',6'-trimethylbiphenyl-2-yl)-7,7,9,9-tetramethyl-1,4-dioxa-8-phosphaspiro[4.5]decane. In embodiments, the phosphine ligand is di-tert-butyl(2',4',6'-triisopropyl-3,6-dimethoxybiphenyl-2-yl)phosphine. In embodiments, the phosphine ligand is 7,7,9,9-tetramethyl-8-(2',4',6'-triisopropyl-3,6-dimethoxybiphenyl-2-yl)-1,4-dioxa-8-phosphaspiro[4.5]decane.

Compound (5) may be sulfonamidated in the presence of a catalyst and/or a catalyst precursor. In embodiments, the catalyst and/or a catalyst precursor is a transition metal compound. In embodiments, the transition metal catalyst or the transition metal catalyst precursor is a palladium catalyst or a palladium catalyst precursor, respectively. Palladium catalysts or palladium catalyst precursors may include, for example, tetrakis(triphenylphosphine)palladium(0), dichlorobis(tri-o-tolylphosphine)palladium(II), palladium(II) acetate, [1,1'-bis(diphenylphosphino) ferrocene]dichloropalladium(II), bis(dibenzylideneacetone) palladium(0), tris(dibenzylideneacetone)dipalladium(0), tris(dibenzylideneacetone)dipalladium(0) chloroform adduct, dichlorobis(tricyclohexylphosphine) palladium(II), dichlorobis(triphenylphosphine) palladium(II), chloro(η3-allyl) palladium(II) dimer-triphenylphosphine, palladium(II) chloride, palladium(II) bromide, bis(acetonitrile)dichloropalladium(II) and any other suitable palladium catalyst or palladium catalyst precursor. In embodiments, the palladium catalyst precursor or palladium catalyst precursor is tetrakis(triphenylphosphine) palladium(0). In embodiments, the palladium catalyst or palladium catalyst precursor is dichlorobis(tri-o-tolylphosphine) palladium(II). In embodiments, the palladium catalyst or palladium catalyst precursor is palladium(II) acetate. In embodiments, the palladium catalyst or palladium catalyst precursor is [1,1'-bis(diphenylphosphino)ferrocene]dichloro palladium(II). In embodiments, the palladium catalyst or palladium catalyst precursor is tris(dibenzylideneacetone)dipalladium(0). In embodiments, the palladium catalyst or palladium catalyst precursor is bis(dibenzylideneacetone) palladium(0). In embodiments, the palladium catalyst or palladium catalyst precursor is palladium(II) bromide. In embodiments, the palladium catalyst or palladium catalyst precursor is palladium(II) chloride. In embodiments, the palladium catalyst or palladium catalyst precursor is bis(acetonitrile)dichloropalladium(II). In embodiments, the palladium catalyst or palladium catalyst precursor is dichlorobis(tricyclohexylphosphine) palladium(II). In embodiment, the palladium catalyst or palladium catalyst precursor is dichlorobis(triphenylphosphine) palladium(II). In embodiment, the palladium catalyst or palladium catalyst precursor is chloro(η3-allyl)palladium (II) dimer-triphenylphosphine.

In embodiments, compound (5) is sulfonamidated in the presence of solvent. Solvents may include, for example, tetrahydrofuran, N,N-dimethylformamide, N,N-dimethylacetamide, N-methylpyrrolidone, dimethyl sulfoxide, 1,2-dimethoxyethane, 1,4-dioxane, acetonitrile, cyclopentyl methyl ether, toluene, benzene, tert-amyl alcohol, and tert-butyl alcohol, 2-methyltetrahydrofuran, ethyl acetate, isopropyl acetate, anisole, trifluorotoluene and any other suitable solvent and combinations thereof. In embodiments, the solvent is tetrahydrofuran. In embodiments, the solvent is N,N-dimethylformamide. In embodiments, the solvent is N,N-dimethylacetamide. In embodiments, the solvent is N-methylpyrrolidone. In embodiments, the solvent is dimethyl sulfoxide. In embodiments, the solvent is 1,2-dimethoxyethane. In embodiments, the solvent is 1,4-dioxane. In embodiments, the solvent is acetonitrile. In embodiments, the solvent is cyclopentyl methyl ether. In embodiments, the solvent is toluene. In embodiments, the solvent is benzene. In embodiments, the solvent is tert-amyl alcohol. In embodiments, the solvent is tert-butyl alcohol. In embodiments, the solvent is 2-methyltetrahydrofuran. In embodiments, the solvent is ethyl acetate. In embodiments, the solvent is isopropyl acetate. In embodiments, the solvent is anisole. In embodiments, the solvent is trifluorotoluene. In embodiments, the solvent is a mixture of 2-methyltetrahydrofuran and ethyl acetate. In embodiments, the solvent is a mixture of tert-amyl alcohol and dimethyl sulfoxide. In embodiments, the solvent is a 7:1 mixture of tert-amyl alcohol and dimethyl sulfoxide. In embodiments, the solvent is a 1:2 mixture of 2-methyltetrahydrofuran and ethyl acetate. In embodiments, the solvent is a 1:3 mixture of 2-methyltetrahydrofuran and ethyl acetate.

Compound (5) may be sulfonamidated in the presence of base. Bases may include, for example, potassium phosphate tribasic, cesium carbonate, potassium carbonate, sodium carbonate, sodium tert-butoxide, potassium tert-butoxide, sodium phenoxide, lithium bis(trimethylsilyl)amide, lithium diisopropylamide and any other suitable base and combinations thereof. In embodiments, the base is potassium phosphate tribasic. In embodiments, the base is potassium phosphate tribasic with a particle size (D90) less than or equal to 120 µm. In embodiments, the base is potassium phosphate tribasic hydrated with less than one molar equivalent of water. In embodiments, the base is potassium phosphate tribasic hydrated with less than 0.5 molar equivalents of water. In embodiments, the base is potassium phosphate tribasic with a particle size (D90) less than or equal to 120 µm and hydrated with less than one molar equivalent of water. In embodiments, the base is potassium phosphate tribasic with a particle size (D90) less than or equal to 120 µm and hydrated with less than 0.5 molar equivalent of water. In embodiments, the base is cesium carbonate. In embodiments, the base is potassium carbonate. In embodiments, the base is sodium carbonate. In embodiments, the base is sodium tert-butoxide. In embodiments, the base is potassium tert-butoxide. In embodiments, the base is sodium phenoxide. In embodiments, the base is lithium bis(trimethylsilyl)amide. In embodiments, the base is lithium diisopropylamide.

Compound (5) may be sulfonamidated at a temperature of from about 20° C. to about 130° C. or from about 60° C. to about 100° C. In instances where the reaction is conducted above the boiling point of the reaction solvent, the reaction is conducted in a sealed vessel suitable to contain the pressure of the reaction. In embodiments, compound (5) is sulfonamidated at a temperature of about 60° C., then about 85° C., and finally about 95° C. In embodiments, compound (5) is sulfonamidated at a temperature of about 80° C. and then about 50° C. In embodiments, compound (5) is sulfonamidated at a temperature of about 80° C. and then about 90° C.

Compound (5) may be sulfonamidated in an inert atmosphere. In embodiments, the inert atmosphere is provided by nitrogen. In embodiments, the inert atmosphere is provided by argon.

In an embodiment, compound (5) is reacted with methanesulfonamide under an argon atmosphere in t-amyl alcohol in the presence of potassium phosphate tribasic, tris(dibenzylideneacetone)dipalladium(0) and di-tert-butyl(2',4',6'-triisopropyl-3,4,5,6-tetramethylbiphenyl-2-yl)phosphine to give compound (A).

In an embodiment, compound (5) is reacted with methanesulfonamide under an argon atmosphere in t-amyl alcohol in the presence of potassium phosphate tribasic, tris(dibenzylideneacetone)dipalladium(0) and 7,7,9,9-tetramethyl-8-(2',4',6'-triisopropylbiphenyl-2-yl)-1,4-dioxa-8-phosphaspiro[4.5]decane to give compound (A).

In an embodiment, compound (5) is reacted with methanesulfonamide in t-amyl alcohol in the presence of potassium phosphate tribasic, tris(dibenzylideneacetone)dipalladium(0) and 2,2,6,6-tetramethyl-1-(2',4',6'-triisopropylbiphenyl-2-yl)phosphinane to give compound (A).

In an embodiment, compound (5) is reacted with methanesulfonamide in t-amyl alcohol in the presence of potassium phosphate tribasic, tris(dibenzylideneacetone)dipalladium(0) and 8,8,10,10-tetramethyl-9-(2',4',6'-triisopropylbiphenyl-2-yl)-1,5-dioxa-9-phosphaspiro[5.5]undecane to give compound (A).

In an embodiment, compound (5) is reacted with methanesulfonamide in t-amyl alcohol in the presence of potassium phosphate tribasic, tris(dibenzylideneacetone)dipalladium(0) and 2,2,6,6-tetramethyl-1-(2',4',6'-triisopropylbiphenyl-2-yl)phosphinan-4-ol to give compound (A).

In an embodiment, compound (5) is reacted with methanesulfonamide in t-amyl alcohol in the presence of potassium phosphate tribasic, tris(dibenzylideneacetone)dipalladium(0) and 8-(2',6'-diisopropoxybiphenyl-2-yl)-7,7,9,9-tetramethyl-1,4-dioxa-8-phosphaspiro[4.5]decane to give compound (A).

In an embodiment, compound (5) is reacted with methanesulfonamide in t-amyl alcohol in the presence of potassium phosphate tribasic, tris(dibenzylideneacetone)dipalladium(0) and 1,3,5,7-tetramethyl-8-(2',4',6'-triisopropylbiphenyl-2-yl)-2,4,6-trioxa-8-phosphatricyclo[3.3.1.1$^{3,7}$]decane to give compound (A).

In an embodiment, compound (5) is reacted with methanesulfonamide in t-amyl alcohol in the presence of potassium phosphate tribasic, tris(dibenzylideneacetone)dipalladium(0) and 8-(2',6'-dimethoxybiphenyl-2-yl)-7,7,9,9-tetramethyl-1,4-dioxa-8-phosphaspiro[4.5]decane to give compound (A).

In an embodiment, compound (5) is reacted with methanesulfonamide in t-amyl alcohol in the presence of potassium phosphate tribasic, tris(dibenzylideneacetone)dipalladium(0) and 6-methoxy-N,N-dimethyl-2'-(7,7,9,9-tetramethyl-1,4-dioxa-8-phosphaspiro[4.5]decan-8-yl)biphenyl-2-amine to give compound (A).

In an embodiment, compound (5) is reacted with methanesulfonamide in t-amyl alcohol in the presence of potassium phosphate tribasic, tris(dibenzylideneacetone)dipalladium(0) and 8-(2'-methoxy-1,1'-binaphthyl-2-yl)-7,7,9,9-tetramethyl-1,4-dioxa-8-phosphaspiro[4.5]decane to give compound (A).

In an embodiment, compound (5) is reacted with methanesulfonamide in t-amyl alcohol in the presence of potassium phosphate tribasic, tris(dibenzylideneacetone)dipalladium(0) and 8-(1,1'-binaphthyl-2-yl)-7,7,9,9-tetramethyl-1,4-dioxa-8-phosphaspiro[4.5]decane to give compound (A).

In an embodiment, compound (5) is reacted with methanesulfonamide in t-amyl alcohol in the presence of potassium phosphate tribasic, tris(dibenzylideneacetone)dipalladium(0) and 7,7,9,9-tetramethyl-8-(2-(naphthalen-1-yl)phenyl)-1,4-dioxa-8-phosphaspiro[4.5]decane to give compound (A).

In an embodiment, compound (5) is reacted with methanesulfonamide in t-amyl alcohol in the presence of potassium phosphate tribasic, tris(dibenzylideneacetone)dipalladium(0) and 7,7,9,9-tetramethyl-8-(2-(naphthalen-2-yl)phenyl)-1,4-dioxa-8-phosphaspiro[4.5]decane to give compound (A).

In an embodiment, compound (5) is reacted with methanesulfonamide in tetrahydrofuran in the presence of potassium phosphate tribasic, tris(dibenzylideneacetone)dipalladium(0) and di-tert-butyl(2',4',6'-triisopropyl-3,6-dimethoxybiphenyl-2-yl)phosphine to give compound (A).

In an embodiment, compound (5) is reacted with methanesulfonamide in 2-methyltetrahydrofuran in the presence of potassium phosphate tribasic, tris(dibenzylideneacetone)dipalladium(0) and di-tert-butyl(2',4',6'-triisopropyl-3,6-dimethoxybiphenyl-2-yl)phosphine to give compound (A).

In an embodiment, compound (5) is reacted with methanesulfonamide in ethyl acetate in the presence of potassium phosphate tribasic, tris(dibenzylideneacetone)dipalladium(0) and di-tert-butyl(2',4',6'-triisopropyl-3,6-dimethoxybiphenyl-2-yl)phosphine to give compound (A).

In an embodiment, compound (5) is reacted with methanesulfonamide in t-amyl alcohol in the presence of potassium phosphate tribasic, tris(dibenzylideneacetone)dipalladium(0) and di-tert-butyl(2',4',6'-triisopropyl-3,6-dimethoxybiphenyl-2-yl)phosphine to give compound (A).

In an embodiment, compound (5) is reacted with methanesulfonamide in a mixture of 2-methyltetrahydrofuran and ethyl acetate in the presence of potassium phosphate tribasic, tris(dibenzylideneacetone)dipalladium(0) and di-tert-butyl(2',4',6'-triisopropyl-3,6-dimethoxybiphenyl-2-yl)phosphine to give compound (A).

In an embodiment, compound (5) is reacted with methanesulfonamide in a mixture of 2-methyltetrahydrofuran and ethyl acetate in the presence of potassium phosphate tribasic, tris(dibenzylideneacetone)dipalladium(0) and 7,7,9,9-tetramethyl-8-(2',4',6'-triisopropyl-3,6-dimethoxybiphenyl-2-yl)-1,4-dioxa-8-phosphaspiro[4.5]decane to give compound (A).

Compounds of formula (A) may be converted to a corresponding salt. A salt of compound (A) may be advantageous due to one or more of the properties of the salt, such as, for example, enhanced pharmaceutical stability in differing temperatures and humidities, or a desirable solubility in water or other solvents. Where a salt is intended to be administered to a patient (as opposed to, for example, being in use in an in vitro context), the salt is considered to be pharmaceutically acceptable and/or physiologically compatible. Accordingly, the term "pharmaceutically acceptable" is used adjectivally in this disclosure to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the disclosure. Pharmaceutically acceptable base addition salts of the compounds of formula (A) include, for example, metallic salts and organic salts. Metallic salts may include alkali metal (group Ia) salts, alkaline earth metal (group IIa) salts, and other physiologically acceptable metal salts. Such salts may be made from aluminum, calcium, lithium, magnesium, potassium, sodium, and zinc.

The salt of compound (A) may be the potassium salt, the sodium salt or any other suitable salt. In embodiments, the salt of compound (A) is the potassium salt. In embodiments, the salt of compound (A) is the sodium salt. In an embodiment, compounds of formula (A) may be converted to the corresponding salt, compound (A-s), by treatment with a base, solvent or base in a solvent. For convenient illustration, the salt is shown as having formed at the uracil group as is shown with formula (A-s). The sulfonamide moiety is also a functional group capable of salt formation as illustrated with formula (A-s'). The actual site of salt formation may be at either functional group.

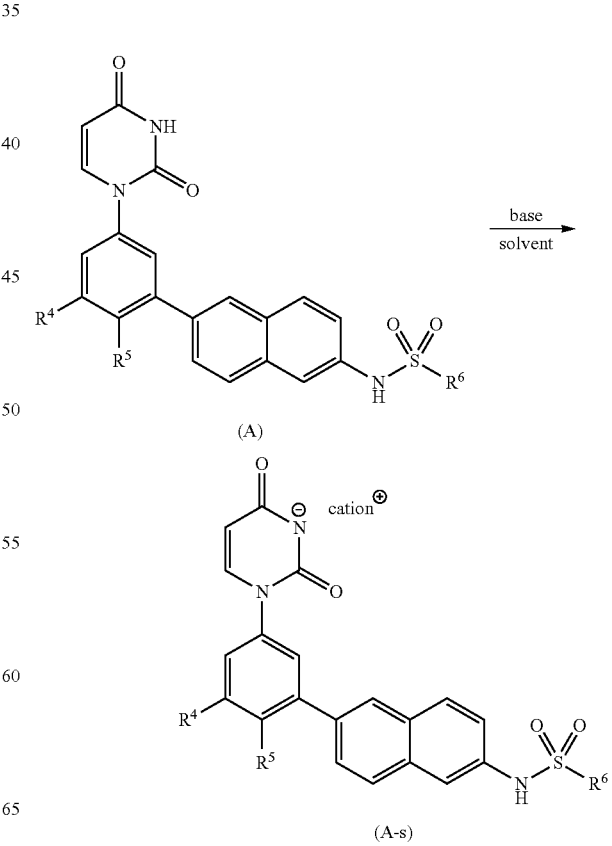

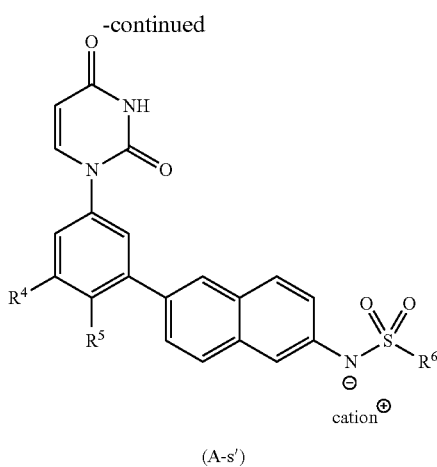

(A-s')

Bases may include, for example, potassium hydroxide, sodium hydroxide and any other suitable base. In embodiments, the base is potassium hydroxide. In embodiments, the base is sodium hydroxide. Solvents may include, for example, dimethyl sulfoxide, 2-propanol, water, and any other suitable solvent or mixtures thereof. In an embodiment, compound (A) is reacted with sodium hydroxide in a mixture of dimethyl sulfoxide, 2-propanol and water to give compound (A-s) as the sodium salt. In an embodiment the conversion to the corresponding salt is conducted at a temperature of about 68° C.

Organic salts of compound (A) may be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

In addition to preparing disclosed compounds, the disclosure is also directed to processes for preparing particular salts and polymorphs of certain disclosed compounds, including intermediates of the disclosed processes, as well as compositions comprising such compounds, salts, and polymorphs. For example, this disclosure is directed, in part, to preparing crystalline forms of N-(6-(3-tert-butyl-5-(2,4-dioxo-3,4-dihydropyrimidin-1(2H)-yl)-2-methoxyphenyl)naphthalen-2-yl)methanesulfonamide (compound (A-1)) and the corresponding sodium and potassium salts, namely the solvate, hydrate, and solvent-free crystalline forms described in International Patent Publication Nos. WO 2009/039134 and WO2009/039127 which are incorporated herein by reference.

B. Process for Preparing 6-(3-tert-butyl-5-(2,4-dioxo-3,4-dihydropyrimidin-1(2H)-yl)-2-methoxyphenyl)naphthalen-2-yl 1,1,2,2,3,3,4,4,4-nonafluorobutane-1-sulfonate (compound (5-I)

Compound (5-I) may be prepared by reacting 1-(3-tert-butyl-5-(6-hydroxynaphthalen-2-yl)-4-methoxyphenyl)pyrimidine-2,4(1H,3H)-dione (compound (4)) with a sulfonyl fluoride, sulfonyl chloride, or sulfonic acid anhydride, wherein $X^1$ is bromo, chloro, fluoro, N-phenyl-trifluoromethylsulfonamidyl, or aryloxy such as 4-nitrophenoxy, and $R^{1a}$ is independently, at each occurrence, aryl, such as p-tolyl or phenyl; alkyl such as methyl or ethyl; fluoroalkyl such as trifluoromethyl, perfluorobutyl, or isomers of perfluorobutyl and other higher and lower homologs such as, but not limited to, perfluoropentyl, perfluorohexyl, and perfluorooctyl; fluoroalkoxyfluoroalkyl such as perfluoroethoxyethyl; —N(alkyl)$_2$; fluoro; —O(alkyl) and —O(aryl); or imidazolyl:

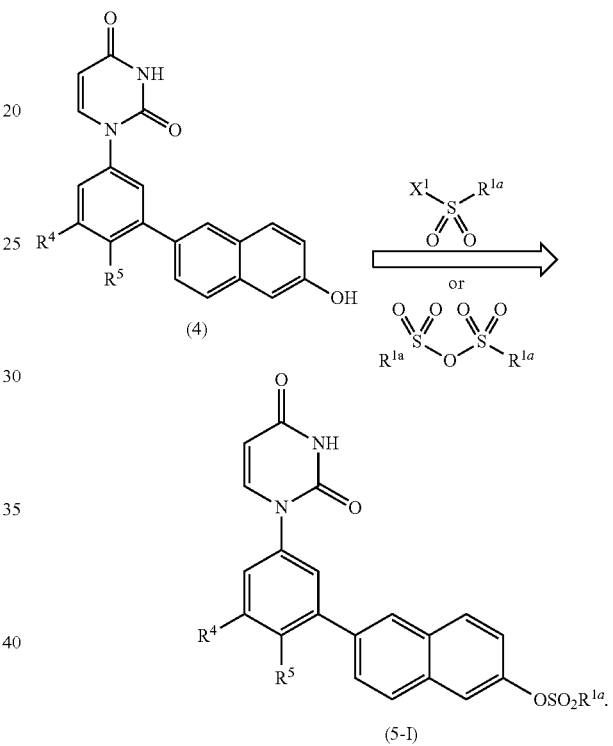

Compound (4) may be sulfonylated in the presence of a base. Bases may include, for example, sodium hydride, sodium hydroxide, sodium methoxide, sodium ethoxide, sodium tert-butoxide, potassium hydride, potassium hydroxide, potassium methoxide, potassium ethoxide, potassium tert-butoxide, potassium carbonate, cesium carbonate, sodium carbonate, sodium bicarbonate, triethylamine, diisopropylethylamine, 4-methylmorpholine, pyridine, 2,6-dimethylpyridine, or any other suitable base. In embodiments, the base is sodium hydride. In embodiments, the base is sodium hydroxide. In embodiments, the base is sodium methoxide. In embodiments, the base is sodium ethoxide. In embodiments, the base is sodium tert-butoxide. In embodiments, the base is potassium hydride. In embodiments, the base is potassium hydroxide. In embodiments, the base is potassium methoxide. In embodiments, the base is potassium ethoxide. In embodiments, the base is potassium tert-butoxide. In embodiments, the base is potassium carbonate. In embodiments, the base is cesium carbonate. In embodiments, the base is sodium carbonate. In embodiments, the base is sodium bicarbonate. In embodiments, the base is triethylamine. In embodiments, the base is diisopropylethylamine. In embodiments, the base is 4-methylmorpholine. In embodiments, the base is pyridine. In embodiments, the base is 2,6-dimethylpyridine.

Compound (4) may be sulfonylated in the presence of solvent. Solvents may include, for example, tetrahydrofuran, 2-methyltetrahydrofuran, dimethyl sulfoxide, N,N-dimethylformamide, N,N-dimethylacetamide, N-methylpyrrolidone, 1,2-dimethoxyethane, 1,4-dioxane, acetonitrile, dichloromethane, chloroform, diethyl ether, or any other suitable solvent or mixtures thereof. In embodiments, the solvent is tetrahydrofuran. In embodiments, the solvent is 2-methyltetrahydrofuran. In embodiments, the solvent is dimethyl sulfoxide. In embodiments, the solvent is N,N-dimethylformamide. In embodiments, the solvent is N,N-dimethylacetamide. In embodiments, the solvent is N-methylpyrrolidone. In embodiments, the solvent is 1,2-dimethoxyethane. In embodiments, the solvent is 1,4-dioxane. In embodiments, the solvent is acetonitrile. In embodiments, the solvent is dichloromethane. In embodiments, the solvent is chloroform. In embodiments, the solvent is diethyl ether. In embodiments, the solvent is a mixture of N,N-dimethylformamide and acetonitrile. In embodiments, the solvent is a 2:3 mixture of N,N-dimethylformamide and acetonitrile.

Compound (4) may be sulfonylated at a temperature of from about −15° C. to about 50° C. or from about −5° C. to about 30° C. In an embodiment, compound (4) is sulfonylated at ambient temperature.

Compound (4) may be sulfonylated in ambient atmosphere or inert atmosphere. In embodiments, the atmosphere is ambient. In embodiments, the inert atmosphere is provided by nitrogen. In embodiments, the inert atmosphere is provided by argon.

In an embodiment, compound (4) is reacted with perfluorobutanesulfonyl fluoride under an inert nitrogen atmosphere in N,N-dimethylformamide at ambient temperature in the presence of potassium carbonate to provide compound (5a).

In an embodiment, compound (4a) is reacted with perfluorobutanesulfonyl fluoride under an inert nitrogen atmosphere in a mixture of N,N-dimethylformamide and acetonitrile at ambient temperature in the presence of potassium carbonate to provide compound (5a).

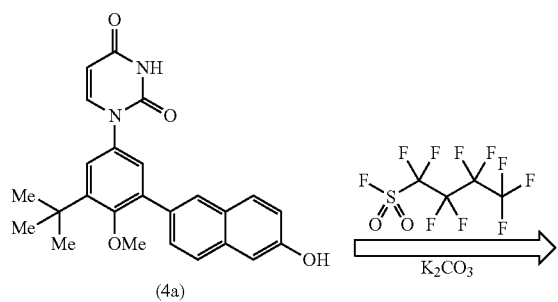

(4a)

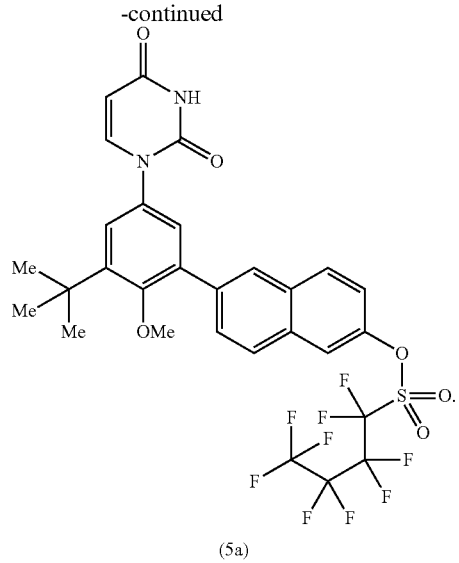

(5a)

In an embodiment, compound (4a) is reacted with 1,1,2,2,3,3,3-heptafluoropropane-1-sulfonyl fluoride under an inert nitrogen atmosphere in N,N-dimethylformamide at ambient temperature in the presence of potassium carbonate to provide 6-(3-tert-butyl-5-(2,4-dioxo-3,4-dihydropyrimidin-1(2H)-yl)-2-methoxyphenyl)naphthalen-2-yl 1,1,2,2,3,3,-heptafluoropropane-1-sulfonate, compound (5b).

In an embodiment, compound (4a) is reacted with 1,1,1,2,3,3,3-heptafluoropropane-2-sulfonyl fluoride under an inert nitrogen atmosphere in N,N-dimethylformamide at ambient temperature in the presence of potassium carbonate to provide 6-(3-tert-butyl-5-(2,4-dioxo-3,4-dihydropyrimidin-1(2H)-yl)-2-methoxyphenyl)naphthalen-2-yl 1,1,1,2,3,3,3-heptafluoropropane-2-sulfonate, compound (5c).

In an embodiment, compound (4a) is reacted with 1,1,2,2,2-pentafluoroethanesulfonyl fluoride under an inert nitrogen atmosphere in N,N-dimethylformamide at ambient temperature in the presence of potassium carbonate to provide compound 6-(3-tert-butyl-5-(2,4-dioxo-3,4-dihydropyrimidin-1(2H)-yl)-2-methoxyphenyl)naphthalen-2-yl 1,1,2,2,2-pentafluoroethanesulfonate, compound (5d).

In an embodiment, compound (4a) is reacted with trifluoromethanesulfonyl fluoride under an inert nitrogen atmosphere in N,N-dimethylformamide at ambient temperature in the presence of potassium carbonate to provide 6-(3-tert-butyl-5-(2,4-dioxo-3,4-dihydropyrimidin-1(2H)-yl)-2-methoxyphenyl)naphthalen-2-yl trifluoromethanesulfonate, compound (5e).

In an embodiment, compound (4a) is reacted with perfluoro(2-ethoxyethane)sulfonyl fluoride under an inert nitrogen atmosphere in N,N-dimethylformamide at ambient temperature in the presence of potassium carbonate to provide 6-(3-tert-butyl-5-(2,4-dioxo-3,4-dihydropyrimidin-1(2H)-yl)-2-methoxyphenyl)naphthalen-2-yl 1,1,2,2-tetrafluoro-2-(perfluoroethoxy)ethanesulfonate, compound (5f).

In an embodiment, compound (4a) is reacted with sulfuryl fluoride under an inert nitrogen atmosphere in N,N-dimethylformamide at ambient temperature in the presence of potassium carbonate to provide 6-(3-tert-butyl-5-(2,4-dioxo-3,4-dihydropyrimidin-1(2H)-yl)-2-methoxyphenyl)naphthalen-2-yl sulfofluoridate, compound (5g).

C. Process for Preparing compounds of formula (4) such as 1-(3-tert-butyl-5-(6-hydroxynaphthalen-2-yl)-4-methoxyphenyl)pyrimidine-2,4(1H,3H)-dione (compound (4))

This disclosure is directed, in part, to compound (4) such as 1-(3-tert-butyl-5-(6-hydroxynaphthalen-2-yl)-4-methoxyphenyl)pyrimidine-2,4(1H,3H)-dione (compound (4a)) or a salt thereof. Compound (4) may be prepared by reacting compound (1) with compound (3) under cross-coupling reaction conditions in the presence of a transition metal catalyst or a transition metal catalyst precursor and ligand, and base.

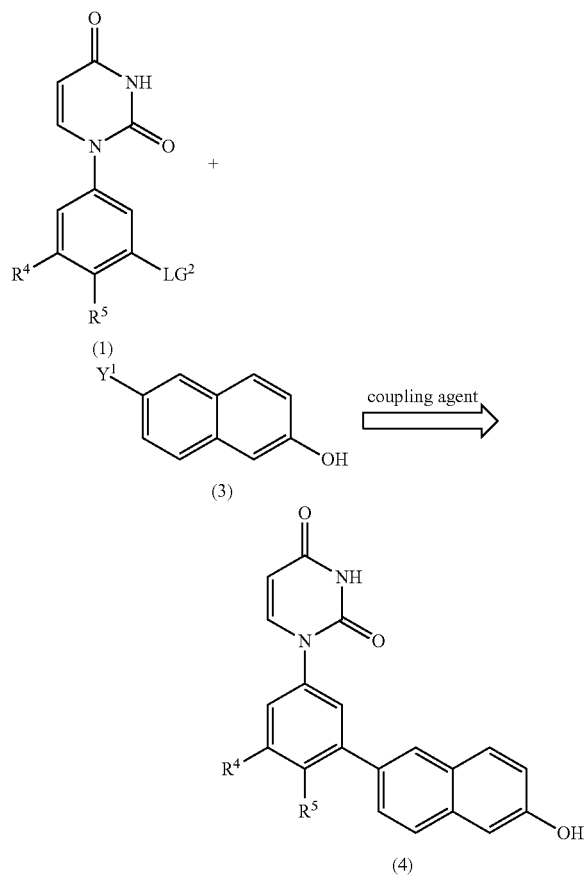

$R^4$ and $R^5$ are as described above. $LG^2$ of compound (1) may be chloro, bromo, iodo, or $-OSO_2R^{1b}$, wherein $R^{1b}$ is selected from aryl, such as p-tolyl or phenyl; alkyl such as methyl or ethyl; fluoroalkyl such as trifluoromethyl, perfluorobutyl, or isomers of perfluorobutyl and other higher and lower homologs such as, but not limited to, perfluoropentyl, perfluorohexyl, and perfluorooctyl; perfluroalkoxyfluoroalkyl such as perfluoroethoxyethyl; fluoro; $-N(alkyl)_2$, $-O(alkyl)$ and $-O(aryl)$; or imidazolyl. In embodiments, $LG^2$ is chloro. In embodiments, $LG^2$ is bromo. In embodiments, $LG^2$ is iodo. In embodiments, $LG^2$ is $-OSO_2$-p-tolyl. In embodiments, $LG^2$ is $-OSO_2$-phenyl. In embodiments, $LG^2$ is $-OSO_2CH_3$. In embodiments, $LG^2$ is $-OSO_2CF_3$. In embodiments, $LG^2$ is $-OSO_2C_4F_9$. In embodiments, $LG^2$ is $-OSO_2N(CH_3)_2$. Compound (1) may include, for example, 1-(3-tert-butyl-5-chloro-4-methoxyphenyl)pyrimidine-2,4(1H,3H)-dione (compound (1a)), 1-(3-bromo-5-tert-butyl-4-methoxyphenyl)pyrimidine-2,4(1H,3H)-dione (compound (1b)), or 1-(3-tert-butyl-5-iodo-4-methoxyphenyl)pyrimidine-2,4(1H,3H)-dione (compound (1c)). The preparation of compound (1) is described in Example 1 below as well as in International Patent Publication No. WO 2009/039127 which is incorporated herein by reference.

$Y^1$ of compound (3) is selected from the group consisting of an organoborane; boronic acid; borate ester; borate salt; zinc halide; zincate; organomagnesium; magnesium halide; magnesium alkoxide; lithium; $-Si(R^{1c})_4$, and $-Sn(R^{1d})_4$, wherein $R^{1c}$ and $R^{1d}$ are selected from the group consisting of alkyl, phenyl, hydroxy, halide, hydride, and alkoxy. In embodiments, $Y^1$ is a boronic acid. In embodiments, $Y^1$ is a borate ester. In embodiments, $Y^1$ is a borate salt. Compound (3) may include, for example, 6-hydroxynaphthalen-2-ylboronic acid (compound (3a)), potassium trifluoro(6-hydroxynaphthalen-2-yl)borate (compound (3b)), and 6-(4,4,5,5-tetramethyl-1,3,2-dioxaborolan-2-yl)naphthalen-2-ol (compound (3c)), each of which are commercially available.

The cross-coupling reaction may be conducted in the presence of catalyst or a catalyst precursor. The catalyst or catalyst precursor may comprise, for example, copper, nickel, palladium, or other suitable metal or mixtures thereof. In embodiments, the catalyst is a transition metal catalyst and/or a transition metal catalyst precursor. In embodiments, the transition metal catalyst or the transition metal catalyst precursor is a palladium catalyst or palladium catalyst precursor. Palladium catalysts or palladium catalyst precursors may include, for example, tetrakis(triphenylphosphine)palladium(0), dichlorobis(triphenylphosphine)palladium(II), tris(dibenzylidineacetone)dipalladium(0), tris(dibenzylidineacetone)dipalladium(0) chloroform adduct, bis(dibenzylidineacetone)palladium(0), palladium(II) diacetate, [1,1'-bis(diphenylphosphino)ferrocene]dichloropalladium(II), complex with dichloromethane, or any other suitable palladium catalyst or palladium catalyst precursor. In embodiments, the palladium catalyst or palladium catalyst precursor is tetrakis(triphenylphosphine)palladium(0). In embodiments, the palladium catalyst or palladium catalyst precursor is dichlorobis(triphenylphosphine)palladium(II). In embodiments, the palladium catalyst or palladium catalyst precursor is tris(dibenzylidineacetone)dipalladium(0). In embodiments, the palladium catalyst or palladium catalyst precursor is bis(dibenzylidineacetone)palladium(0). In embodiments, the palladium catalyst or palladium catalyst precursor is palladium(II) diacetate. In embodiments, the palladium catalyst or palladium catalyst precursor is dichlorobis(triphenylphosphine)palladium(II). In embodiments, the palladium catalyst or palladium catalyst precursor is [1,1'-bis(diphenylphosphino)ferrocene]dichloropalladium(II), complex with dichloromethane.

The cross-coupling reaction may be conducted in the presence of a ligand. In embodiments the ligand is a phosphine. Ligands may include, for example, tri-t-butylphosphine, tricyclohexylphosphine, tris(2-furyl)phosphine, 2,2'-bis(diphenylphosphino)-1,1'-binaphthyl, 1,3,5,7-tetramethyl-8-phenyl-2,4,6-trioxa-8-phosphatricyclo[3.3.1.1$^{3,7}$]decane, biphenyl-2-yldicyclohexylphosphine, dicyclohexyl(2',6'-dimethoxybiphenyl-2-yl)phosphine, dicyclohexyl(2',4',6'-triisopropylbiphenyl-2-yl)phosphine, [4-(dimethylamino)phenyl]bis(tert-butyl)phosphine or any other suitable ligand or salts thereof. In embodiments, the ligand is tri-t-butylphosphine. In embodiments, the ligand is tricyclohexylphosphine. In embodiments, the ligand is, tris(2-furyl)phosphine. In embodiments, the ligand is 2,2'-bis(diphenylphosphino)-1,1'-binaphthyl. In embodiments, the ligand is 1,3,5,7-tetramethyl-8-phenyl-2,4,6-trioxa-8-phosphatricyclo[3.3.1.1$^{3,7}$]decane. In embodiments, the ligand is biphenyl-2-yldicyclohexylphosphine. In embodiments, the ligand is dicyclohexyl(2',6'-dimethoxybiphenyl-2-yl)phosphine. In embodiments, the ligand is dicyclohexyl(2',4',6'-triisopropylbiphenyl-2-yl)phosphine. In embodiments, the ligand is [4-(dimethylamino)phenyl]bis(tert-butyl)phosphine.

Compound (1) may be reacted with compound (3) in the presence of a base. Bases may include, for example, potassium phosphate tribasic, cesium carbonate, potassium carbonate, sodium carbonate, potassium tert-butoxide, cesium fluoride, potassium hydroxide or any other suitable base. In embodiments, the base is potassium phosphate tribasic. In embodiments, the base is cesium carbonate. In embodiments, the base is potassium carbonate. In embodiments, the base is sodium carbonate. In embodiments, the base is potassium tert-butoxide. In embodiments, the base is cesium fluoride. In embodiments, the base is potassium hydroxide.

Compound (1) may be reacted with compound (3) in the presence of solvent. Solvents may include, for example, tetrahydrofuran, 2-methyltetrahydrofuran, N,N-dimethylformamide, 1,2-dimethoxyethane, 1,4-dioxane, ethanol, toluene, water, or any other suitable solvent or mixtures thereof. In embodiments, the solvent is tetrahydrofuran. In embodiments, the solvent is 2-methyltetrahydrofuran. In embodiments, the solvent is N,N-dimethylformamide. In embodiments, the solvent is 1,2-dimethoxyethane. In embodiments, the solvent is 1,4-dioxane. In embodiments, the solvent is ethanol. In embodiments, the solvent is toluene. In embodiments, the solvent is water. In embodiments, the solvent is a tetrahydrofuran and water mixture. In embodiments, the solvent is water. In embodiments, the solvent is a 3:1 mixture of tetrahydrofuran and water.

Compound (1) may be reacted with compound (3) at a temperature of from about 20° C. to about 130° C., or from about 40° C. to about 80° C. In instances where the reaction is conducted above the boiling point of the reaction solvent, the reaction is conducted in a sealed vessel suitable to contain the pressure of the reaction. In an embodiment the reaction is conducted at ambient or elevated temperatures. In an embodiment the reaction is conducted at about 65° C. The heating may be provided either through conventional or microwave heating.

Compound (1) may be reacted with compound (3) in an inert atmosphere. In embodiments, the inert atmosphere is provided by nitrogen. In embodiments, the inert atmosphere is provided by argon.

In an embodiment, 1-(3-tert-butyl-5-iodo-4-methoxyphenyl)pyrimidine-2,4(1H,3H)-dione (compound (1c) is reacted with 6-hydroxynaphthalen-2-ylboronic acid (compound (3a) in tetrahydrofuran in the presence of potassium phosphate tribasic, 1,3,5,7-tetramethyl-8-phenyl-2,4,6-trioxa-8-phosphatricyclo[3.3.1.1$^{3,7}$]decane, and tris(dibenzylideneacetone)dipalladium(0) to provide 1-(3-tert-butyl-5-(6-hydroxynaphthalen-2-yl)-4-methoxyphenyl)pyrimidine-2,4(1H,3H)-dione (compound (4a)).

In an embodiment, 1-(3-tert-butyl-5-iodo-4-methoxyphenyl)pyrimidine-2,4(1H,3H)-dione (compound (1c) is reacted with 6-hydroxynaphthalen-2-ylboronic acid (compound (3a) in a mixture of tetrahydrofuran and water in the presence of potassium phosphate tribasic, 1,3,5,7-tetramethyl-8-phenyl-2,4,6-trioxa-8-phosphatricyclo[3.3.1.1$^{3,7}$]decane, and tris(dibenzylideneacetone)dipalladium(0) to provide 1-(3-tert-butyl-5-(6-hydroxynaphthalen-2-yl)-4-methoxyphenyl)pyrimidine-2,4(1H,3H)-dione (compound (4a)).

Compounds of formula (4) such as 1-(3-tert-Butyl-5-(6-hydroxynaphthalen-2-yl)-4-methoxyphenyl)pyrimidine-2,4 (1H,3H)-dione (compound (4a)) may also be prepared by reacting compound (1-Y$^2$) with compound (3-LG$^3$) under cross-coupling reaction conditions in the presence of a transition metal catalyst and/or a transition metal catalyst precursor, base, and ligand.

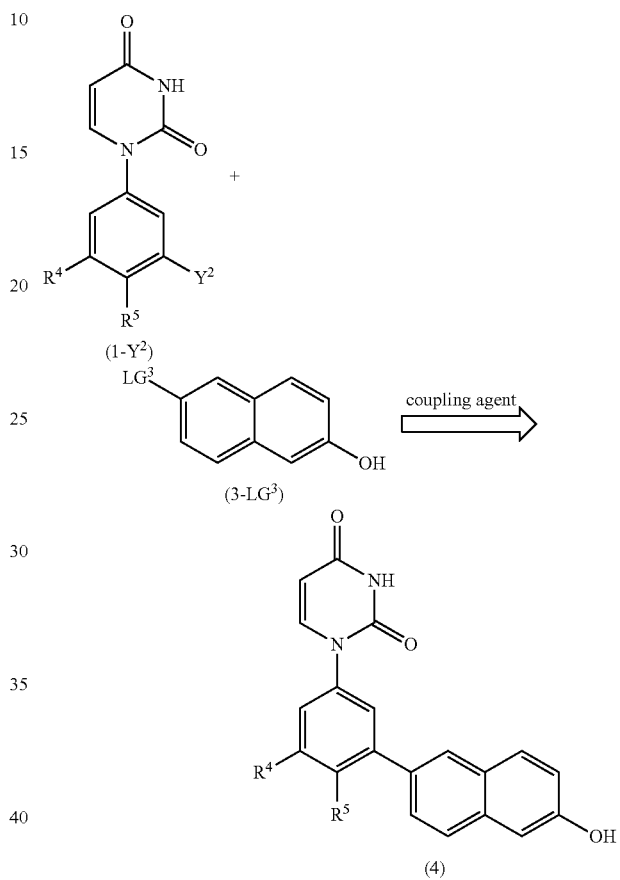

LG$^3$ of compound (3-LG$^3$) may be chloro, bromo, iodo, or —OSO$_2$R$^{1b}$, wherein R$^{1b}$ is selected from aryl, such as p-tolyl or phenyl; alkyl such as methyl or ethyl; fluoroalkyl such as trifluoromethyl, perfluorobutyl, or isomers of perfluorobutyl and other higher and lower homologs such as, but not limited to, perfluoropentyl, perfluorohexyl, and perfluorooctyl; perfluoroethoxyethyl; fluoro; —N(alkyl)$_2$; —O(alkyl) and —O(aryl); or imidazolyl. In embodiments, LG$^3$ is chloro. In embodiments, LG$^3$ is bromo. In a further embodiment, LG$^3$ is iodo. In embodiments, LG$^3$ is —OSO$_2$-p-tolyl. In embodiments, LG$^3$ is —OSO$_2$-phenyl. In embodiments, LG$^3$ is —OSO$_2$CH$_3$. In embodiments, LG$^3$ is —OSO$_2$CF$_3$. In embodiments, LG$^3$ is —OSO$_2$C$_4$F$_9$. In embodiments, LG$^3$ is —OSO$_2$N(CH$_3$)$_2$. Compound (3-LG$^3$) may include, for example, 6-chloronaphthalen-2-ol (compound (3-LG$^3$a)), 6-bromonaphthalen-2-ol (compound (3-LG$^3$b)), or 6-iodonaphthalen-2-ol (compound (3-LG$^3$c)). Compounds of formula (3-LG$^3$) are either commercially available or can be prepared by methods known to one skilled in the art.

Y$^2$ of compound (1-Y$^2$) is selected from the group consisting of an organoborane; boronic acid; borate ester; borate salt; zinc halide; zincate; organomagnesium; magnesium halide; magnesium alkoxide; lithium; —Si($R^{1c}$)$_4$, and —Sn ($R^{1d}$)$_4$, wherein $R^{1c}$ and $R^{1d}$ are selected from the group consisting of alkyl, phenyl, hydroxy, halide, hydride, and alkoxy. In embodiments, $Y^2$ is a boronic acid. In embodiments, $Y^2$ is a borate ester. In embodiments, $Y^3$ is a borate salt. Compound (1-$Y^2$) may include, for example, 3-tert-butyl-5-(2,4-dioxo-3,4-dihydropyrimidin-1(2H)-yl)-2-methoxyphenylboronic acid (compound (1-$Y^2$a)), potassium (3-tert-butyl-5-(2,4-dioxo-3,4-dihydropyrimidin-1(2H)-yl)-2-methoxyphenyl)trifluoroborate (compound (1-$Y^2$b)), and 1-(3-tert-butyl-4-methoxy-5-(4,4,5,5-tetramethyl-1,3,2-dioxaborolan-2-yl)phenyl)pyrimidine-2,4(1H,3H)-dione (compound (1-$Y^2$c)). Compounds of formula (1-$Y^2$) may be prepared from compounds of formula (1) by methods known to one skilled in the art.

The cross-coupling reaction may be conducted in the presence of catalyst or catalyst precursor. The catalyst or catalyst precursor may comprise, for example, copper, nickel, palladium, or other suitable metal or mixtures thereof. In embodiments, the catalyst or catalyst precursor is a transition metal catalyst and/or a transition metal catalyst precursor. In embodiments, the transition metal catalyst or the transition metal catalyst precursor is a palladium catalyst or palladium catalyst precursor. Palladium catalysts or palladium catalyst precursors may include, for example, tetrakis(triphenylphosphine)palladium(0), dichlorobis(triphenylphosphine)palladium(II), tris(dibenzylidineacetone)dipalladium(0), bis(dibenzylidineacetone)palladium(0), palladium(II) diacetate, [1,1'-bis(diphenylphosphino)ferrocene]dichloropalladium(II), complex with dichloromethane, or any other suitable palladium catalyst or palladium catalyst precursor. In embodiments, the palladium catalyst or palladium catalyst precursor is tetrakis(triphenylphosphine)palladium(0). In embodiments, the palladium catalyst or palladium catalyst precursor is dichlorobis(triphenylphosphine)palladium(II). In embodiments, the palladium catalyst or palladium catalyst precursor is tris(dibenzylidineacetone)dipalladium(0). In embodiments, the palladium catalyst or palladium catalyst precursor is bis(dibenzylidineacetone)palladium(0). In embodiments, the palladium catalyst or palladium catalyst precursor is palladium(II) diacetate. In embodiments, the palladium catalyst or palladium catalyst precursor is dichlorobis(triphenylphosphine)palladium. In embodiments, the palladium catalyst or palladium catalyst precursor is [1,1'-bis(diphenylphosphino)ferrocene]dichloropalladium(II), complex with dichloromethane.

The cross-coupling reaction may be conducted in the presence of a ligand. In embodiments the ligand is a phosphine. Ligands or salts thereof may include, for example, tri-t-butylphosphine, tricyclohexylphosphine, tris(2-furyl)phosphine, 2,2'-bis(diphenylphosphino)-1,1'-binaphthyl, 1,3,5,7-tetramethyl-8-phenyl-2,4,6-trioxa-8-phosphatricyclo[3.3.1.1$^{3,7}$]decane, biphenyl-2-yldicyclohexylphosphine, dicyclohexyl(2',6'-dimethoxybiphenyl-2-yl)phosphine, dicyclohexyl(2',4',6'-triisopropylbiphenyl-2-yl)phosphine, or any other suitable ligand. In embodiments, the ligand is tri-t-butylphosphine. In embodiments, the ligand is tricyclohexylphosphine. In embodiments, the ligand is, tris(2-furyl)phosphine. In embodiments, the ligand is 2,2'-bis(diphenylphosphino)-1,1'-binaphthyl. In embodiments, the ligand is 1,3,5,7-tetramethyl-8-phenyl-2,4,6-trioxa-8-phosphatricyclo[3.3.1.1$^{3,7}$]decane. In embodiments, the ligand is biphenyl-2-yldicyclohexylphosphine. In embodiments, the ligand is dicyclohexyl(2',6'-dimethoxybiphenyl-2-yl)phosphine. In embodiments, the ligand is dicyclohexyl(2',4',6'-triisopropylbiphenyl-2-yl)phosphine.

Compound (1-$Y^2$) may be reacted with compound (3-LG$^3$) in the presence of a base. Bases may include, for example, potassium phosphate tribasic, cesium carbonate, potassium carbonate, sodium carbonate, potassium tert-butoxide, cesium fluoride, potassium hydroxide or any other suitable base. In embodiments, the base is potassium phosphate tribasic. In embodiments, the base is cesium carbonate. In embodiments, the base is potassium carbonate. In embodiments, the base is sodium carbonate. In embodiments, the base is potassium tert-butoxide. In embodiments, the base is cesium fluoride. In embodiments, the base is potassium hydroxide.

Compound (1-$Y^2$) may be reacted with compound (3-LG$^3$) in the presence of solvent. Solvents may include, for example, tetrahydrofuran, 2-methyltetrahydrofuran, N,N-dimethylformamide, 1,2-dimethoxyethane, 1,4-dioxane, ethanol, toluene, water, or any other suitable solvent or mixtures thereof. In embodiments, the solvent is tetrahydrofuran. In embodiments, the solvent is 2-methyltetrahydrofuran. In embodiments, the solvent is N,N-dimethylformamide. In embodiments, the solvent is 1,2-dimethoxyethane. In embodiments, the solvent is 1,4-dioxane. In embodiments, the solvent is ethanol. In embodiments, the solvent is toluene. In embodiments, the solvent is water.

Compound (1-$Y^2$) may be reacted with compound (3-LG$^3$) at a temperature of from about 20° C. to about 130° C., or from about 40° C. to about 80° C. In instances where the reaction is conducted above the boiling point of the reaction solvent, the reaction is conducted in a sealed vessel suitable to contain the pressure of the reaction. In an embodiment the reaction is conducted at ambient or elevated temperatures. In an embodiment the reaction is conducted at about 65° C. The temperature may be controlled either through conventional or microwave heating.

Compound (1-$Y^2$) may be reacted with compound (3-LG$^3$) in an inert atmosphere. In embodiments, the inert atmosphere is provided by nitrogen. In embodiments, the inert atmosphere is provided by argon.

In an embodiment, 3-tert-butyl-5-(2,4-dioxo-3,4-dihydropyrimidin-1(2H)-yl)-2-methoxyphenylboronic acid (compound (1-$Y^2$a)) is reacted with 6-iodonaphthalen-2-ol (compound (3-LG$^3$c)) in tetrahydrofuran in the presence of potassium phosphate tribasic, 1,3,5,7-tetramethyl-8-phenyl-2,4,6-trioxa-8-phosphatricyclo[3.3.1.1$^{3,7}$]decane, and tris(dibenzylideneacetone)dipalladium(0) to provide 1-(3-tert-butyl-5-(6-hydroxynaphthalen-2-yl)-4-methoxyphenyl)pyrimidine-2,4(1H,3H)-dione (compound (4a)).

D. Definitions

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkyl" as used herein, means a straight or branched, saturated hydrocarbon chain containing from 1 to 10 carbon atoms. The term "lower alkyl" or "$C_{1-6}$ alkyl" means a straight or branched chain hydrocarbon containing 1 to 6 carbon atoms. The term "$C_{1-3}$ alkyl" means a straight or branched chain hydrocarbon containing 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylamino" or "N-alkylamino" as used herein, means an alkyl group, as defined herein, appended to the parent molecular moiety through an amino group, as defined herein. Representative examples of alkylamino include, but are not limited to, methylamino, ethylamino, and sec-butylamino.

The term "N-alkylaminoalkyl" as used herein, means an alkyl group, as defined herein, appended to the parent molecular moiety through an aminoalkyl group, as defined herein. Representative examples of N-alkylaminoalkyl include, but are not limited to, methylaminoethyl and methylamino-2-propyl.

The term "alkylcarbonyl" means an alkyl group appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylene" denotes a divalent group derived from a straight or branched chain hydrocarbon 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "N-(alkyl)sulfamoyl" as used herein, means an alkyl group, as defined herein, appended to the parent molecular moiety through a sulfamoyl group, as defined herein. Representative examples of N-(alkyl)sulfamoyl include, but are not limited to, N-methylsulfamoyl and N-ethylsulfamoyl.

The term "alkylthio" as used herein, means an alkyl group, as defined herein, appended to the parent molecular moiety through a sulfur atom. Representative examples of alkylthio include, but are not limited to, methylthio, ethylthio, tert-butylthio, and hexylthio.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amino" as used herein means an —$NH_2$ group.

The term "aminoalkyl" as used herein means at least one amino group, as defined herein, appended to the parent molecular moiety through an alkyl group, as defined herein. Representative examples of aminoalkyl include, but are not limited to, aminomethyl, 2-aminoethyl, 2-methyl-2-hydroxyethyl, and 2-aminopropyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present disclosure can be unsubstituted or substituted.

The term "arylalkyl," as used herein, refers to an aryl group attached to the parent molecular moiety through an alkyl group. Representative examples of arylalkyl include, but not limited to, phenylmethyl, phenylethyl and naphthylmethyl.

The term "carbonyl" as used herein, refers to —C(=O).

The term "cyano" as used herein, means a —CN group.

The term "cycloalkoxy" as used herein, means a cycloalkyl group, as defined herein, appended to the parent molecular moiety through an oxygen atom. Representative examples of cycloalkoxy include, but are not limited to, cyclohexyloxy and cyclopropoxy.

The term "cycloalkyl" or "cycloalkane" as used herein, means a monocyclic, a bicyclic, or a tricyclic cycloalkyl. The monocyclic cycloalkyl is a carbocyclic ring system containing three to eight carbon atoms, zero heteroatoms and zero double bonds. Examples of monocyclic ring systems include, but are not limited to, cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[$3.3.1.0^{3,7}$]nonane (octahydro-2,5-methanopentalene or noradamantane), and tricyclo[$3.3.1.1^{3,7}$]decane (adamantane). The monocyclic, bicyclic, and tricyclic cycloalkyls can be unsubstituted or substituted, and are attached to the parent molecular moiety through any substitutable atom contained within the ring system.

The term "dialkylamino" or "N,N-dialkylamino" as used herein, means two independently selected alkyl groups, as defined herein, appended to the parent molecular moiety through an amino group, as defined herein. Representative examples of dialkylamino include, but are not limited to, N,N-dimethylamino, N-ethyl-N-methylamino, and N-isopropyl-N-methylamino.

The term "N,N-dialkylaminoalkyl" as used herein, means two independently selected alkyl groups, as defined herein, appended to the parent molecular moiety through an aminoalkyl group, as defined herein. Representative examples of N,N-dialkylaminoalkyl include, but are not limited to, N,N-dimethylaminoethyl and N,N-methyl(2-propyl)aminoethyl.

The term "trialkylammoniumalkyl" or "N,N,N-trialkylammoniumalkyl" means aminoalkyl in which there are three alkyl group substituted on the nitrogen of the amino group resulting in a net positive charge. The three substituted alkyl groups can be the same of different. Examples of N,N,N-trialkylammoniumalkyl include trimethylammoniummethyl and diethylmethylammoniummethyl.

The term "N,N-(dialkyl)sulfamoyl" as used herein, means two independently selected alkyl groups, as defined herein, appended to the parent molecular moiety through a sulfamoyl group, as defined herein. Representative examples of N,N-(dialkyl)sulfamoyl include, but are not limited to, N,N-dimethylsulfamoyl and N-methyl-N-ethyl-sulfamoyl.

The term "fluoroalkoxy" as used herein, means at least one fluorine, as defined herein, appended to the parent molecular moiety through an alkoxy group, as defined herein. Representative examples of fluoroalkoxy include, but are not limited to, fluoromethoxy, 2-fluoroethoxy, trifluoromethoxy, and pentafluoroethoxy.

The term "fluoroalkyl" as used herein means at least one fluoro group, as defined herein, appended to the parent molecular moiety through an alkyl group, as defined herein. Representative examples of fluoroalkyl include, but are not limited to, fluoromethyl, difluoromethyl, trifluoromethyl, perfluorobutyl, perfluoropentyl, perfluorohexyl, perfluorooctyl pentafluoroethyl, and 2,2,2-trifluoroethyl.

The term "halo" or "halogen" as used herein, means Cl, Br, I, or F.

The term "haloalkoxy" as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl" as used herein, means an alkyl group, as defined herein, in which one, two, three, four, five or six hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl includes a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinazolinyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present disclosure can be substituted or unsubstituted and are connected to the parent molecular moiety through any carbon atom or any nitrogen atom contained within the ring systems.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of oxygen, nitrogen, phosphorus and sulfur. The three- or four-membered ring contains zero or one double bond, and one heteroatom selected from the group consisting of oxygen, nitrogen, phosphorus and sulfur. The five-membered ring contains zero or one double bond and one, two or three heteroatoms selected from the group consisting of oxygen, nitrogen, phosphorus and sulfur. The six-membered ring contains zero, one or two double bonds and one, two, or three heteroatoms selected from the group consisting of oxygen, nitrogen, phosphorus and sulfur. The seven- and eight-membered rings contains zero, one, two, or three double bonds and one, two, or three heteroatoms selected from the group consisting of oxygen, nitrogen, phosphorus and sulfur. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, phosphinane, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydropyrimidinyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, 9-phosphabicyclo[3.3.1]nonane, 8-phosphabicyclo[3.2.1]octane, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), oxa-adamantane (2-oxatricyclo[3.3.1.1$^{3,7}$]decane), and 2,4,6-trioxa-8-phosphatricyclo[3.3.1.1$^{3,7}$]decane. The monocyclic, bicyclic, and tricyclic heterocycles are connected to the parent molecular moiety through any carbon atom or any nitrogen atom contained within the rings, and can be unsubstituted or substituted.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl(thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl(furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl(azinyl), piperidinyl, diazinyl (including pyridazinyl(1,2-diazinyl), pyrimidinyl(1,3-diazinyl), or pyrazinyl(1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl alternatively may be 2 or 3 rings fused together, such as, for example, indolizinyl, pyranopyrrolyl, 4H-quinolizinyl, purinyl, naphthyridinyl, pyridopyridinyl (including pyrido[3,4-b]-pyridinyl, pyrido[3,2-b]-pyridinyl, or pyrido[4,3-b]-pyridinyl), and pteridinyl. Other examples of fused-ring heterocyclyls include benzo-fused heterocyclyls, such as indolyl, isoindolyl(isobenzazolyl, pseudoisoindolyl), indoleninyl(pseudoindolyl), isoindazolyl(benzpyrazolyl), benzazinyl (including quinolinyl(1-benzazinyl) or isoquinolinyl(2-benzazinyl)), phthalazinyl, quinoxalinyl, quinazolinyl, benzodiazinyl (including cinnolinyl(1,2-benzodiazinyl) or quinazolinyl(1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "hydroxyl" or "hydroxy" as used herein, means an —OH group.

The term "hydroxyalkoxy" as used herein, means an hydroxy group, as defined herein, appended to the parent molecular moiety through an alkoxy group, as defined herein. Representative examples of hydroxyalkoxy include, but are not limited to, hydroxyethoxy, and 2-hydroxypropoxy.

The term "hydroxyalkyl" as used herein means at least one hydroxy group, as defined herein, appended to the parent molecular moiety through an alkyl group, as defined herein. Representative examples of hydroxyalkyl include, but are not limited to, hydroxymethyl, 2-hydroxyethyl, 2-methyl-2-hydroxyethyl, 3-hydroxypropyl, 2,3-dihydroxypentyl, and 2-ethyl-4-hydroxyheptyl.

The term "oxo" as used herein, means a =O group.

The term "oxoalkyl" as used herein, means at least one oxo group, as defined herein, appended to the parent molecular moiety through an alkyl group, as defined herein. Representative examples of oxoalkyl include, but are not limited to, acetyl, propan-1-one, propan-2-one, and butan-2-one.

The term "sulfamate" as used herein, means a —OS(O)$_2$N($Z^3$)$_2$, wherein $Z^3$ is hydrogen or an optionally substituted alkyl, aryl, haloalkyl, or heteroaryl, as defined herein. Representative examples of sulfamate include, but are not limited to sulfamate and dimethylsulfamate.

The term "sulfamoyl" as used herein, means a —S(O)$_2$NH$_2$ group.

The term "sulfate" as used herein, means a $Z^1$OS(O)$_2$O—, wherein $Z^1$ is an optionally substituted alkyl, aryl, haloalkyl, or heteroaryl, as defined herein. Representative examples of sulfonate include, but are not limited to, methylsulfate, trifluoromethylsulfate, and phenylsulfate.

The term "sulfonamide" as used herein, means a $Z^1$S(O)$_2$N($Z^2$)— group, as defined herein, wherein $Z^1$ is an optionally substituted alkyl, aryl, haloalkyl, or heteroaryl as defined herein, and $Z^2$ is hydrogen or alkyl. Representative examples of sulfonamide include, but are not limited to, methanesulfonamide, trifluoromethanesulfonamide, and benzenesulfonamide.

The term "sulfonate" as used herein, means a $Z^1$S(O)$_2$O— group, as defined herein, wherein $Z^1$ is an optionally substituted alkyl, aryl, haloalkyl, or heteroaryl, as defined herein. Representative examples of sulfonate include, but are not limited to, methanesulfonate, trifluoromethanesulfonate, 1,1,2,2,3,3,4,4,4-nonafluorobutane-1-sulfonate, 1H-imidazole-1-sulfonate and p-toluenesulfonate.

The term "thio" or "mercapto" means a —SH group.

The term "thioalkyl" as used herein, means at least one thio group, as defined herein, appended to the parent molecular moiety through an alkyl group, as defined herein. Representative examples of thioalkyl include, but are not limited to, thiomethyl or mercaptomethyl and, 2-thioethyl or 2-mercaptoethyl.

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there is more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "substituent" and "radical" are used interchangeably herein.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

As used herein, the number of ring atoms in a heterocyclyl moiety can be identified by the prefix "$M_x$-$M_y$," where x is the minimum and y is the maximum number of ring atoms in the heterocyclyl moiety.

A prefix attached to a multi-component substituent only applies to the first component. To illustrate, the term "alkylcycloalkyl" contains two components: alkyl and cycloalkyl. Thus, the $C_1$-$C_6$-prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkoxyalkyl indicates that only the alkoxy component of the alkoxyalkyl substituent is substituted with one or more halogen radicals. If halogen substitution may alternatively or additionally occur on the alkyl component, the substituent would instead be described as "halogen-substituted alkoxyalkyl" rather than "haloalkoxyalkyl." If the halogen substitution may only occur on the alkyl component, the substituent would instead be described as "alkoxyhaloalkyl."

If substituents are described as being "independently selected" from a group, each substituent is selected independent of the other. Each substituent, therefore, may be identical to or different from the other substituent(s).

When words are used to describe a substituent, the rightmost-described component of the substituent is the component that has the free valence.

E. Compositions

This disclosure also is directed, in part, to compositions comprising the disclosed compounds or salts thereof or polymorphs thereof, and compositions comprising compounds or salts thereof or polymorphs thereof prepared by the disclosed processes. In embodiments, compounds of formula (A) such as N-(6-(3-tert-butyl-5-(2,4-dioxo-3,4-dihydropyrimidin-1(2H)-yl)-2-methoxyphenyl) naphthalen-2-yl)methanesulfonamide (compound (A-1)) and its salts or polymorphs thereof prepared by the above processes may be included in compositions. These compositions may also comprise one or more conventional pharmaceutically acceptable carriers, adjuvants, and/or vehicles (together referred to as "excipients").

Compositions may include solid dosage forms. Solid dosage forms may include, for example, capsules, tablets, pills, powders, granules or any other suitable solid dosage form. In such solid dosage forms, the compounds or salts may be combined with one or more excipients. If administered per os, the compounds or salts may be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, polyvinyl alcohol or any other suitable excipient, and then tableted or encapsulated for convenient administration. Such capsules or tablets may contain a controlled-release formulation, as can be provided in, for example, a dispersion of the compound or salt in hydroxypropylmethyl cellulose. In the case of capsules, tablets, and pills, the dosage forms may also comprise buffering agents, such as sodium citrate, or magnesium or calcium carbonate, bicarbonate or any other suitable buffering agent. Tablets and pills additionally may be prepared with enteric coatings.

The compounds disclosed herein may be administered as a free acid or as a salt. The compounds or their salts may be administered (in single or divided doses) in a total daily dose of from about 0.001 to about 100 mg/kg, from about 0.001 to about 30 mg/kg, or from about 0.01 to about 10 mg/kg (i.e., mg of the compound or salt per kg body weight). Compound (A-1) or a salt thereof may be administered (in single or divided doses) at a total daily dose of from about 4 mg/kg to about 30 mg/kg or from about 10 mg/kg to about 25 mg/kg. Compound (A-1) or a salt thereof may be administered in a total daily dose amount of from about 600 mg to about 1800 mg or from about 800 mg to about 1600 mg. In an embodiment, compound (A-1) or a salt thereof is administered in a dosage unit composition of about 400 mg. In an embodiment, compound (A-1) or a salt thereof is administered in a dosage unit composition of about 800 mg. In an embodiment, compound (A-1) or a salt thereof is administered in a dosage unit composition of about 1200 mg.

Dosage unit compositions may contain such amounts or submultiples thereof to make up the total daily dose. The administration of the compound or salt may be repeated a plurality of times. Multiple doses per day may be used to achieve the total daily dose.

Factors affecting the dosage regimen include the type, age, weight, sex, diet, and condition of the patient; the severity of the pathological condition; the severity of the pathological condition; pharmacological considerations, such as the activity, efficacy, pharmacokinetic, and toxicology profiles of the particular compound or salt used; whether a drug delivery system is utilized; and the specific drug combination. Thus, the dosage regimen actually employed can vary widely, and therefore, can derive from the dosage regimen set forth above.

F. Methods of Use

This disclosure also is directed, in part, to methods of using the disclosed compounds or salts thereof or polymorphs thereof, compounds or salts thereof or polymorphs thereof prepared by the disclosed processes, compositions comprising the disclosed compounds or salts thereof or polymorphs thereof, and compositions comprising compounds or salts thereof or polymorphs thereof prepared by the disclosed processes.

For example, this disclosure is directed, in part, to methods of using the disclosed compounds, salts and compositions for inhibiting replication of an RNA virus. The methods comprise exposing the virus to a disclosed compound, salt or composition. In embodiments, replication of the RNA virus is inhibited in vitro. In embodiments, replication of the RNA virus is inhibited in vivo. In embodiments, the RNA virus whose replication is being inhibited is a single-stranded, positive sense RNA virus. In embodiments, the RNA virus whose replication is being inhibited is a virus from the Flaviviridae family. In embodiments, the RNA virus whose replication is being inhibited is HCV.

This disclosure is directed, in part, to methods of using the disclosed compounds, salts and compositions for inhibiting HCV RNA polymerase. The methods comprise exposing the polymerase to a disclosed compound, salt or composition. In some embodiments, HCV RNA polymerase activity is inhibited in vitro. In some embodiments, HCV RNA polymerase activity is inhibited in vivo.

The term "inhibiting" means reducing the level of RNA virus replication/HCV polymerase activity either in vitro or in vivo. For example, if a composition of the disclosure reduces the level of RNA virus replication by at least about 10% compared to the level of RNA virus replication before the virus was exposed to the composition, then the composition inhibits RNA virus replication. In some embodiments, the compound, salt or composition can inhibit RNA virus replication by at least about 20%, at least about 30%, at least about 40%, at least about 50%, at least about 60%, at least about 70%, at least about 80%, at least about 90%, or at least about 95%.

This disclosure is directed, in part, to methods of using the disclosed compounds, salts and compositions for treating a disease that can be treated by inhibiting HCV RNA polymerase. Thus, this disclosure also is directed, in part, to a method for treating hepatitis C in an animal in need of such treatment. These methods comprise administering to the animal one or more of the disclosed compounds, salts and compositions. In some embodiments, a therapeutically effective amount of the compound (or salt thereof) is administered to the animal "Treating" means ameliorating, suppressing, eradicating, preventing, reducing the risk of, and/or delaying the onset of the disease being treated. Applicants specifically intend that the term "treating" encompass administration of the compositions of the disclosure to an HCV-negative patient that is a candidate for an organ transplant. The methods of treatment are particularly suitable for use with humans, but may be used with other animals, particularly mammals. A "therapeutically-effective amount" or "effective amount" is an amount that will achieve the goal of treating the targeted condition.

In some embodiments, the methods comprise combination therapy, wherein a compound, salt, and/or composition of the disclosure is co-administered with one or more additional therapeutic agents, such as, for example, another therapeutic agent used to treat hepatitis C (e.g., interferon or interferon/ribavirin combination, or an HCV inhibitor such as, for example, an HCV polymerase inhibitor an HCV protease inhibitor, an NS5a inhibitor). The compound, salts, and/or compositions of this disclosure can also be co-administered with therapeutic agents other than therapeutic agents used to treat hepatitis C (e.g., anti-HIV agents). In these co-administration embodiments, the compound, salts, and/or compositions of the disclosure and the additional therapeutic agent(s) may be administered in a substantially simultaneous manner (e.g., or within about 5 minutes of each other), in a sequential manner, or both. It is contemplated that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient.

This disclosure also is directed, in part, to use of the disclosed compounds, salts, and/or compositions, and, optionally one or more additional therapeutic agents to prepare a medicament. For example, compounds of formula (A) such as N-(6-(3-tert-butyl-5-(2,4-dioxo-3,4-dihydropyrimidin-1(2H)-yl)-2-methoxyphenyl)naphthalen-2-yl)methanesulfonamide (compound (A-1)) made by disclosed processes can be used in the manufacture of a medicament.

In embodiments, the medicament is for co-administration with one or more additional therapeutic agents.

In embodiments, the medicament is for inhibiting replication of an RNA virus such as HCV.

In embodiments, the medicament is for inhibiting HCV RNA polymerase.

In embodiments, the medicament is for treating hepatitis C.

This disclosure also is directed, in part, to the disclosed compounds, salts, and/or compositions, and, optionally one or more additional therapeutic agents, for use in inhibiting replication of an RNA virus, for inhibiting HCV RNA polymerase, or for treating hepatitis C.

EXAMPLES

The following examples are merely illustrative, and not limiting to this disclosure in any way.

Abbreviations which have been used in the descriptions of the Schemes and Examples that follow are: DMF for N,N-dimethylformamide; DMSO for dimethyl sulfoxide; HPLC for high performance liquid chromatography; LC-MS for liquid chromatographyl-mass spectrometry; Me for methyl; MeCN for acetonitrile; pa % for peak area %; $Pd_2dba_3$ for tris(dibenzylideneacetone)dipalladium(0); THF for tetrahydrofuran; v/v for volume/volume; wt for weight; w/w for weight/weight.

Certain reactions in the Examples below may have been analyzed using reversed-phase HPLC. Analyses may have been conducted using a reversed-phase amide column (Ascentis® Express RP-Amide, 100×4.6 mm ID, 2.7 micron). Compounds may have been eluted using a gradient of about 25-95% acetonitrile in 0.1% aqueous perchloric acid at a flow rate of 1.9 mL/minute. One specific gradient starts with 25-44% acetonitrile over 12.5 minutes; 44-77% acetonitrile over 6 minutes; 77-95% acetonitrile over 1.5 minutes; hold at 95% acetonitrile for 3.5 minutes; 95-25% acetonitrile over 0.01 minutes; and hold at 25% acetonitrile for 3.99 minutes.

Example 1

Preparation of 1-(3-tert-butyl-5-iodo-4-methoxyphenyl)pyrimidine-2,4(1H,3H)-dione (compound (1c))

Part A

Preparation of 2-tert-butyl-4,6-diiodophenol 2-tert-Butylphenol (99.95 g, 665.36 mmol) was dissolved in 1250 mL methanol and converted to the corresponding phenoxide with 31.96 g (799.0 mmol, 1.2 equivalents) of sodium hydroxide by stirring the sodium hydroxide pellets at room temperature, and then cooling the reaction mixture in an ice/salt bath. Sodium iodide (299.34 g, 1997.07 mmol, 3.0 equivalents) and 8.3% bleach (1265.83 g, 1411.39 mmol, 2.1 equivalents) were added to the cold reaction solution in four equal portions, the bleach being added while keeping the reaction mixture at <0° C. 500 mL of 20% (w/w) sodium thiosulfate solution was added over an 18 minute period, with the temperature rising from −0.6° C. to 2.5° C. The pH of the reaction mixture was adjusted to approximately 3 by adding 197.5 mL of concentrated HCl over a period of 97 minutes with the reaction temperature going from 1.2° C. to 4.1° C. The resulting slurry was filtered, and the wet cake washed with approximately 2 L of water. The wet cake was left on the Buchner funnel under vacuum overnight (approximately 15 hours) to yield 289.33 g (potency adjusted yield=254.61 g) of the title product.

Part B

Preparation of 1-tert-butyl-3,5-diiodo-2-methoxybenzene

The product from Part A (93% assay, 21.6 g, 50 mmol) was dissolved in 140 mL of acetone. Methyl iodide (4.2 mL, 67.5 mmol, 1.35 equivalents) was added, followed by 50% aqueous sodium hydroxide (5.0 g, 62.5 mmol, 1.25 equivalents). The reaction was stirred overnight, then concentrated to approximately 50-60 mL. 80 mL of heptanes were added followed by 50 mL of water, and the layers were shaken and separated, and the aqueous layer was back extracted with 20 mL of heptanes. The organic layers were combined and washed twice with 50 mL each of 10% aqueous NaCl to afford 91.1 grams of a heptane solution, which assayed to 19.1 g of the title compound.

Part C

Preparation of 1-(3-tert-butyl-5-iodo-4-methoxyphenyl)pyrimidine-2,4(1H,3H)-dione Uracil (33.3 g, 297 mmol, 1.2 equivalents), K₃PO₄ (106 g, 500 mmol, 2.1 equivalents), CuI (4.6 g, 24.2 mmol, 0.1 equivalents), and N-(2-cyanophenyl)picolinamide (6.4 g, 28.7 mmol, 0.12 equivalents) were charged to a flask, and the mixture was sparged with argon. The 1-tert-butyl-3,5-diiodo-2-methoxybenzene was solvent switched into acetonitrile, dissolved in 1 L dimethyl sulfoxide and sparged with argon and added to the solids. The reaction was heated to 60° C. for 16 hours. After cooling, the reaction was diluted with 2 L ethyl acetate and washed with 2.6 L water (back extracted with 3×1 L ethyl acetate). The combined organic layers were washed with 2×1 L of 0.25 M copper(II) acetate then 2×830 mL of 15% NH₄Cl and then 800 mL of brine. The organic layer was then concentrated, heptane (1 L) was added to the residue, and the mixture was re-evaporated. The resulting residue was then triturated with refluxing 85:15 (v/v) heptane:isopropyl acetate for 4 hours. After cooling, the product was collected by filtration and washed with an additional 330 mL of 85:15 v/v heptanes: ethyl acetate to yield after drying 66.9 g (70% yield) of the title compound as a white solid. ¹H NMR (400 MHz, CDCl₃) δ ppm 8.66 (s, 1H), 7.65 (d, J=2.6 Hz, 1H), 7.25 (dd, J=4.8, 3.2 Hz, 2H), 5.81 (dd, J=7.9, 2.0 Hz, 1H), 3.93 (s, 3H), 1.39 (s, 9H).

Example 1-2

Preparation of 1-(3-tert-butyl-5-iodo-4-methoxyphenyl)pyrimidine-2,4(1H,3H)-dione (compound (1c))

Six reactions were set up as follows: A degassed solution of 1-tert-butyl-3,5-diiodo-2-methoxybenzene (1.18 grams, 2.5 mmol) in 10 mL of dimethyl sulfoxide was degassed, then added to a vial containing uracil (336 mg, 3.0 mmol, 1.2 equiv.), N-(2-cyanophenyl)benzamide (67 mg, 0.30 mmol, 0.12 equiv.), CuI (48 mg, 0.25 mmol, 0.10 equiv.) and potassium phosphate (1.11 grams, 5.25 mmol, 2.1 equiv.). Three of the reactions also contained sodium ascorbate (20 mg, 0.10 mmol, 0.04 equiv.).

The reactions were heated to 60° C. for 10 minutes, and then treated as follows. Of the experiments without ascorbate, one was not further treated, one was treated with 2.5 mL of air, and one with 5 mL of air. Likewise, of the experiments with ascorbate, one was not further treated, one was treated with 2.5 mL of air, and one with 5 mL of air. Heating was continued at 60° C. for an additional 15 hours, then analyzed by HPLC. The table below indicates the effect of both air and sodium ascorbate on the course of the reaction.

| Reaction | Air added | Ascorbate added | Conversion |
|---|---|---|---|
| 1 | none | none | 82% |
| 2 | none | 0.04 equiv. | 91% |
| 3 | 2.5 mL | none | 74% |
| 4 | 2.5 mL | 0.04 equiv. | 88% |
| 5 | 5 mL | none | 60% |
| 6 | 5 mL | 0.04 equiv. | 82% |

As seen in FIG. 1, reactions with ascorbate afford higher conversion than corresponding reactions without the additive, and they are less sensitive to the presence of air.

Example 2

Preparation of 1-(3-tert-butyl-5-(6-hydroxynaphthalen-2-yl)-4-methoxyphenyl)pyrimidine-2,4(1H,3H)-dione (compound (4a))

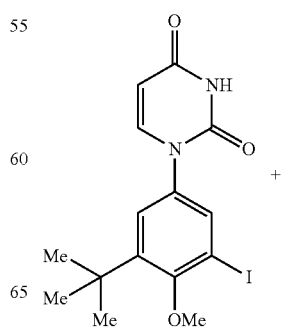

-continued

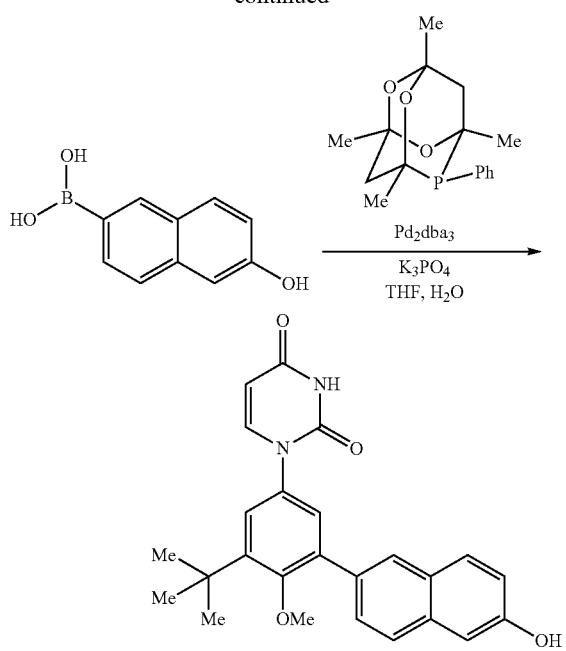

This reaction is sensitive to oxygen, and care was taken to establish and maintain an inert atmosphere in the handling and use of air-sensitive materials or mixtures. All solution transfers were accomplished by cannula technique using nitrogen as the inert gas. Anhydrous tetrahydrofuran was sparged with nitrogen gas for 2 hours prior to use to render it anaerobic. Hereafter this is referred to as degassed tetrahydrofuran.

A 100-mL round-bottom flask was charged with 12.9 g of potassium phosphate tribasic (60.8 mmol, 2.0 equivalents), a magnetic stir bar, and 60 mL of water. The mixture was stirred to dissolve the solids, and the aqueous solution was sparged with nitrogen gas for 2 hours prior to use. Hereafter this is referred to as the phosphate solution.

A 100-mL round-bottom flask was purged with nitrogen gas and charged with 282 mg of tris(dibenzylideneacetone)dipalladium(0) (0.31 mmol, 0.02 equivalents Pd), 413 mg of phosphine ligand, 1,3,5,7-tetramethyl-8-phenyl-2,4,6-trioxa-8-phosphatricyclo[3.3.1.1$^{3,7}$]decane (1.4 mmol, 2.3 equivalents relative to Pd) and a magnetic stir bar. The flask was sealed with a septum and the atmosphere above the solids was purged with nitrogen gas. Sixty mL of degassed tetrahydrofuran was added to the flask and the mixture was stirred under a nitrogen atmosphere. This solution was sparged with nitrogen for 15 minutes prior to use and is hereafter referred to as the catalyst solution.

A 500-mL jacketed reactor was equipped with an overhead stirrer and reflux condenser and the atmosphere was purged with nitrogen gas. The reactor was charged with 12.1 g of 1-(3-tert-butyl-5-iodo-4-methoxyphenyl)pyrimidine-2,4(1H,3H)-dione, (30.3 mmol, 1.0 equivalent) and 5.98 g of 6-hydroxynaphthalen-2-ylboronic acid (31.8 mmol, 1.05 equivalents). The atmosphere was purged with nitrogen gas with stirring of the solid reagents for 20 minutes. The reactor was charged with 120 mL of degassed tetrahydrofuran, and the mixture was stirred to dissolve the solids. The solution was sparged with nitrogen gas for 10 minutes. The phosphate solution was added to the reactor by cannula, followed by the catalyst solution. The resulting biphasic mixture was stirred aggressively to ensure adequate phase mixing, and the jacket was warmed to 65° C. The reaction jacket was cooled to room temperature prior to quench.

After 2.5 hours, the reaction jacket was cooled to room temperature prior to quench.

The workup of the reaction was also conducted under anaerobic conditions. Fifty-seven grams of sodium chloride and 4.2 g of cysteine (15 weight equivalents relative to palladium catalyst) were dissolved in 300 mL of water, and the resulting solution was sparged with inert gas for 2 hours prior to use. To quench the reaction, approximately ⅓ of this solution was transferred to the reaction mixture by cannula under nitrogen gas and the resulting biphasic mixture was stirred vigorously for 2 hours. The mechanical agitation was halted, the two solutions were allowed to separate, and the aqueous solution was drained out of the reactor through the bottom valve. Approximately ⅓ of the quench solution was transferred to the reaction mixture by cannula under nitrogen gas and the resulting biphasic mixture was stirred vigorously for 45 minutes. The mechanical agitation was halted, the two solutions were allowed to separate, and the aqueous solution was drained out of the reactor through the bottom valve. The final portion of the quench solution was transferred to the reaction mixture by cannula, the resulting biphasic mixture was stirred vigorously for 45 minutes and the aqueous solution was drained out of the reactor through the bottom valve.

The remainder of the workup was not conducted under anaerobic conditions. The pale yellow organic solution was drained from the reactor through the bottom valve and filtered over a pad of grade 4 Filtrol® (1 cm deep by 4.5 cm diameter). The reactor and filter cake were rinsed with 70 mL of tetrahydrofuran. The bulk of the solvent was distilled in vacuo (ca 90-130 torr) at ca 40° C. with good agitation from an overhead stirrer. The solution was concentrated to approximately 50 mL volume, during which time the product began to precipitate out. Ethyl acetate (100 mL, about 8 mL of solvent per gram of the product) was added to the mixture, and the resultant slurry was stirred overnight at room temperature. The crystalline material was isolated by filtration and the filter cake was washed twice with 20 mL portions of ethyl acetate. The wet cake was air-dried on the filter and dried in a vacuum oven at 50° C. at approximately 250 torr with a gentle nitrogen sweep overnight.

The desired product was isolated as a white solid (11.6 g, 96.4% potency vs. standard, 88% potency-adjusted yield). $^1$H NMR (400 MHz, DMSO-d$_6$) δ ppm 11.39 (d, J=2.1 Hz, 1H), 9.82 (s, 1H), 7.91 (d, J=0.8 Hz, 1H), 7.80 (d, J=8.9 Hz, 1H), 7.77-7.74 (m, 2H), 7.58 (dd, J=8.5, 1.7 Hz, 1H), 7.32 (d, J=2.7 Hz, 1H), 7.27 (d, J=2.7 Hz, 1H), 7.16 (d, J=2.3 Hz, 1H), 7.10 (dd, J=8.8, 2.4 Hz, 1H), 5.64 (dd, J=7.9, 2.2 Hz, 1H), 3.23 (s, 3H), 1.41 (s, 9H).

Example 2-1

Alternative preparation of 1-(3-tert-butyl-5-(6-hydroxynaphthalen-2-yl)-4-methoxyphenyl)pyrimidine-2,4(1H,3H)-dione (compound (4a))

This reaction is air-sensitive and the reaction was conducted under anaerobic conditions. A 100-mL round-bottom flask was purged with nitrogen gas and charged with 229 mg of tris(dibenzylideneacetone)dipalladium(0) (0.25 mmol, 0.02 equivalents Pd), 323 mg of 1,3,5,7-tetramethyl-8-phenyl-2,4,6-trioxa-8-phosphatricyclo[3.3.1.1$^{3,7}$]decane (1.13 mmol, 0.045 equivalents) and a magnetic stir bar. The flask was sealed with a septum and the atmosphere above the solids was purged with nitrogen gas. Sixty mL of degassed tetrahydrofuran was added to the flask and the mixture was stirred under a nitrogen atmosphere for 20 minutes. This solution is hereafter referred to as the catalyst solution.

A 500-mL jacketed reactor was equipped with an overhead stirrer and reflux condenser and the atmosphere was purged with nitrogen gas. The reactor was charged with 10.0 g of 1-(3-tert-butyl-5-iodo-4-methoxyphenyl)pyrimidine-2,4(1H,3H)-dione, (25.1 mmol, 1.0 equivalent), 4.98 g of 6-hydroxynaphthalen-2-ylboronic acid (26.6 mmol, 1.06 equivalents) and 10.3 g of potassium phosphate tribasic (48.7 mmol, 2.0 equivalents). The atmosphere was purged with nitrogen gas with stirring of the solid reagents for 20 minutes. The reactor was charged with 100 mL of tetrahydrofuran, 50 mL of water, and the mixture was stirred to dissolve the solids. The biphasic mixture was sparged with nitrogen gas for 30 minutes. The catalyst solution was transferred to the main reactor by positive nitrogen pressure through a cannula. The resulting biphasic mixture was stirred aggressively and warmed to an internal temperature between 60 and 65° C. under nitrogen for 2 hours. The reaction mixture was cooled to an internal temperature between 50 and 55° C. before quench.

The workup of the reaction was conducted under anaerobic conditions at an internal temperature between 50 and 55° C. Fifteen grams of sodium chloride and 1.0 g of cysteine were dissolved in 80 mL of water, and the resulting solution was sparged for 1 hour. This solution was transferred to the reaction mixture by cannula with nitrogen gas pressure and the resulting biphasic mixture was stirred vigorously for 45 minutes. The mechanical agitation was halted, the two solutions were allowed to separate, and the aqueous solution was drained out of the reactor through the bottom valve. Fifteen grams of sodium chloride and 1.0 g of cysteine were dissolved in 80 mL of water, and the resulting solution was sparged for 1 hour. This solution was transferred to the reaction mixture by cannula with nitrogen gas pressure and the resulting biphasic mixture was stirred vigorously for 45 minutes. The mechanical agitation was halted, the two solutions were allowed to separate, and the aqueous solution was drained out of the reactor through the bottom valve.

The pale yellow organic solution was drained from the reactor through the bottom valve and filtered over a polypropylene filter to remove palladium black. The reactor and filter cake were rinsed with 22 mL of tetrahydrofuran and 50 mL of ethyl acetate was added to the organic solution. The solution was distilled at atmospheric pressure (approximately 66° C. internal temperature) with continuous addition of 110 mL of ethyl acetate, keeping the volume of the solution roughly constant during the distillation. During the constant-volume distillation, solids began to precipitate in the reactor. After the ethyl acetate was charged, the distillation was continued at atmospheric pressure, concentrating the slurry to approximately 60 mL total volume. The solution was cooled to an internal temperature of approximately 30° C. and held for 3 hours with stirring. The crystalline material was isolated by filtration and the filter cake was washed twice with 20 mL portions of ethyl acetate. The wet cake was dried in a vacuum oven at 50° C. with a gentle nitrogen sweep overnight. The desired product was isolated as an off-white solid (8.33 g, 80% yield). $^1$H NMR (400 MHz, DMSO-$d_6$) δ ppm δ 11.39 (d, J=2.1 Hz, 1H), 9.82 (s, 1H), 7.91 (d, J=0.8 Hz, 1H), 7.80 (d, J=8.9 Hz, 1H), 7.77-7.74 (m, 2H), 7.58 (dd, J=8.5, 1.7 Hz, 1H), 7.32 (d, J=2.7 Hz, 1H), 7.27 (d, J=2.7 Hz, 1H), 7.16 (d, J=2.3 Hz, 1H), 7.10 (dd, J=8.8, 2.4 Hz, 1H), 5.64 (dd, J=7.9, 2.2 Hz, 1H), 3.23 (s, 3H), 1.41 (s, 9H).

Example 2-2

Alternative preparation of 1-(3-tert-butyl-5-(6-hydroxynaphthalen-2-yl)-4-methoxyphenyl)pyrimidine-2,4(1H,3H)-dione (compound (4a))

This reaction is air-sensitive and the reaction was conducted under nitrogen atmosphere. A 100-mL round-bottom flask was purged with nitrogen gas and charged with 303 mg of tris(dibenzylideneacetone)dipalladium(0) (0.33 mmol, 0.02 equivalents Pd), 411 mg of 1,3,5,7-tetramethyl-8-phenyl-2,4,6-trioxa-8-phosphatricyclo[3.3.1.1$^{3,7}$]decane (1.40 mmol, 0.045 equivalents) and a magnetic stir bar. The flask was sealed with a septum and the atmosphere above the solids was purged with nitrogen gas. Seventy-five (75) mL of degassed tetrahydrofuran was added to the flask and the mixture was stirred under a nitrogen atmosphere for 25 minutes. This solution is hereafter referred to as the catalyst solution.

A 500-mL jacketed reactor was equipped with an overhead stirrer and reflux condenser and the atmosphere was purged with nitrogen gas. The reactor was charged with 12.5 g of 1-(3-tert-butyl-5-iodo-4-methoxyphenyl)pyrimidine-2,4(1H,3H)-dione, (31.2 mmol, 1.0 equivalent), 6.20 g of 6-hydroxynaphthalen-2-ylboronic acid (33.0 mmol, 1.06 equivalents) and 13.0 g of potassium phosphate tribasic (61.2 mmol, 2.0 equivalents). The reactor was charged with 130 mL of tetrahydrofuran, 65 mL of water, and the mixture was stirred to dissolve the solids. The biphasic mixture was sparged with nitrogen gas for 30 minutes. The catalyst solution was transferred to the main reactor by positive nitrogen pressure through a cannula. The resulting biphasic mixture was stirred aggressively and warmed to an internal temperature between 60 and 65° C. under nitrogen for 2.5 hours. The reaction mixture was cooled to an internal temperature between 50 and 55° C. before quench.

The workup of the reaction was conducted under anaerobic conditions at an internal temperature between 50 and 55° C. Sodium chloride (18.8 g) and cysteine (1.25 g) were dissolved in 100 mL of water, and the resulting solution was sparged with nitrogen for 40 minutes. This solution was transferred to the reaction mixture by cannula with nitrogen gas pressure and the resulting biphasic mixture was stirred vigorously for 45 minutes. The mechanical agitation was halted, the two solutions were allowed to separate, and the aqueous solution was drained out of the reactor through the bottom valve. Sixty-three (63) mL of degassed tetrahydrofuran were added to the reactor by cannula with positive nitrogen pressure. Sodium chloride (18.9 g) and cysteine (1.333 g) were dissolved in 100 mL of water, and the resulting solution was sparged with nitrogen for 40 minutes. This solution was transferred to the reaction mixture by cannula with nitrogen gas pressure and the resulting biphasic mixture was stirred vigorously for 45 minutes. The mechanical agitation was halted, the two solutions were allowed to separate, and the aqueous solution was drained out of the reactor through the bottom valve.

The pale yellow organic solution was drained from the reactor through the bottom valve and filtered through a thin pad of filter aid on a polyethylene filter while warm. The reactor and filter cake were rinsed with 32 mL of tetrahydrofuran, and 65 mL of ethyl acetate was added to the organic solution. The solution was distilled at atmospheric pressure (approximately 66° C. internal temperature) with continuous addition of 190 mL of ethyl acetate, keeping the volume of the solution roughly constant during the distillation. During the constant-volume distillation, solids began to precipitate in the reactor. After the ethyl acetate was charged, the distillation was continued at atmospheric pressure, concentrating the slurry to approximately 90 mL total volume. The slurry was cooled to an internal temperature of approximately 40° C. and was concentrated further in vacuo to a total volume of approximately 50 mL. The slurry was cooled to an internal temperature of 30° C. and held for 16 hours with stirring. The crystalline material was isolated by filtration, and the filter cake was washed twice with 25 mL portions of ethyl acetate. The wet cake was dried in a vacuum oven at 50° C. with a gentle nitrogen sweep overnight. The desired product was isolated as an off-white solid (11.4 g, 99.5% potent vs. standard, 87% potency-adjusted yield).

Example 3

Preparation of 6-(3-tert-butyl-5-(2,4-dioxo-3,4-dihydropyrimidin-1(2H)-yl)-2-methoxyphenyl)naphthalen-2-yl 1,1,2,2,3,3,4,4,4-nonafluorobutane-1-sulfonate (compound (5a))

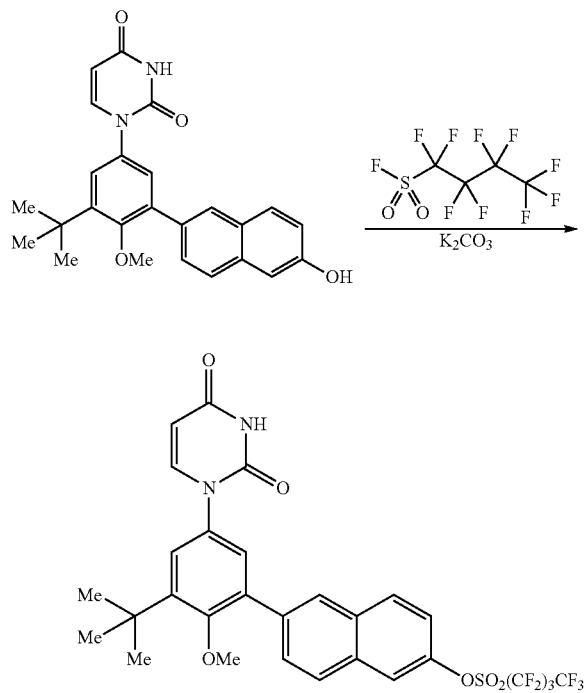

A reactor was equipped with an overhead stirrer in the central neck and charged with 45.0 g of 1-(3-tert-butyl-5-(6-hydroxynaphthalen-2-yl)-4-methoxyphenyl)pyrimidine-2,4(1H,3H)-dione (97.8 weight %, 106 mmol, 1.0 equivalent) and 21.9 g of 325 mesh potassium carbonate (159 mmol, 1.5 equivalents). The atmosphere was purged with nitrogen gas while the solids were stirred. The flask was charged with 445 mL of N,N-dimethylformamide, and the slurry was stirred to dissolve the 1-(3-tert-butyl-5-(6-hydroxynaphthalen-2-yl)-4-methoxyphenyl)pyrimidine-2,4(1H,3H)-dione. The purge was stopped and the reaction was conducted under a slight positive pressure of nitrogen gas. Perfluorobutanesulfonyl fluoride (35.2 g, 117 mmol, 1.1 equivalents) was added in one portion, and the mixture was stirred vigorously to mix the immiscible liquids overnight.

The inorganic solids were separated by filtration, and the flask and filter cake were rinsed with approximately 30 mL of N,N-dimethylformamide. The N,N-dimethylformamide solution was filtered directly into a second flask with an overhead stirrer. With stirring, 112 g of water (25 weight % of total N,N-dimethylformamide employed) was added to the N,N-dimethylformamide solution of product over approximately 0.5 hour to induce precipitation of the desired product, and the mixture was allowed to stir for 5 hours. The wet cake was isolated by filtration with recirculation of the liquors to recover all the solids. The wet cake was washed with 60 mL of 25% (v/v) water/N,N-dimethylformamide, then 85 mL water.

The solids were dissolved in 760 mL of isopropyl acetate. The resultant organic solution was washed once with 200 mL of water, twice with 270 mL portions of water and once with 200 mL of water to remove residual N,N-dimethylformamide. Solvent was removed by distillation at approximately 130 torr with heating to 55° C. until the total volume was approximately 200 mL. With efficient stirring, heptane (450 mL) was added to the warm (55° C.) slurry. The slurry was allowed to cool to room temperature overnight with stirring. The desired product was isolated by filtration, with recycling of the liquors to isolate all of the solids material. The wet cake was washed twice with 100 mL portions of 20% (v/v) isopropyl acetate/heptane. The wet cake was air-dried on the filter and dried in a vacuum oven at 50° C. at approximately 250 torr with a gentle nitrogen sweep overnight. The title compound was isolated as a white solid (64.0 g, 87% yield). $^1$H NMR (600 MHz, DMSO-$d_6$) δ ppm 11.42 (s, 1H), 8.21-8.15 (m, 4H), 7.84 (dd, J=8.6, 1.7 Hz, 1H), 7.77 (d, J=7.9 Hz, 1H), 7.60 (dd, J=9.0, 2.5 Hz, 1H), 7.39 (d, J=2.7 Hz, 1H), 7.35 (d, J=2.7 Hz, 1H), 5.66 (d, J=7.9 Hz, 1H), 3.21 (s, 3H), 1.41 (s, 9H); $^{13}$C NMR (151 MHz, DMSO-$d_6$) δ ppm 163.7, 156.7, 150.6, 147.1, 145.7, 143.6, 137.4, 134.2, 134.1, 132.3, 132.1, 131.3, 128.5, 128.4, 128.1, 127.2, 125.2, 120.0, 119.2, 101.4, 60.5, 35.0, 30.4; $^{19}$F NMR (564 MHz, DMSO-$d_6$) δ ppm −79.9 (3F), −109.9 (2F), −120.7 (2F), −125.4 (2F).

Example 3-1

Alternative preparation of 6-(3-tert-butyl-5-(2,4-dioxo-3,4-dihydropyrimidin-1(2H)-yl)-2-methoxyphenyl)naphthalen-2-yl 1,1,2,2,3,3,4,4,4-nonafluorobutane-1-sulfonate (compound (5a))

A 250-L, 3-neck round-bottom flask equipped with an overhead stirrer was charged with 10 g of 1-(3-tert-butyl-5-(6-hydroxynaphthalen-2-yl)-4-methoxyphenyl)pyrimidine-2,4(1H,3H)-dione (98 wt %, 23.5 mmol, 1.0 equiv) and 6.5 g of milled potassium carbonate (325 mesh, 47.1 mmol, 2.0 equiv). Acetonitrile (MeCN, 60 mL, 6 mL per gram of naphthol) and N,N-dimethylformamide (DMF, 40 mL, 4 mL per gram of naphthol) was charged to the reactor and the slurry was stirred. Perfluorobutanesulfonyl fluoride (8.3 g, 26 mmol, 1.1 equiv) was charged to the well-stirred mixture over 60 minutes by syringe pump. A trace (<0.1 area %) of starting material was detected by HPLC analysis of an aliquot after 20 minutes of reaction time. The acetonitrile/dimethylformamide solution was filtered over a coarse fritted funnel to separate the inorganic solids, and the flask and filter was rinsed with 15 mL of 3:2 (v/v) acetonitrile/dimethylformamide. The total mass of solvents employed was approximately 92 g.

First Crystallization:

The acetonitrile/dimethylformamide solution was transferred to a 3-neck flask equipped with an overhead stirrer. Water (50 g, 54 wt % with respect to total solution charged) was added to the well-stirred solution over 100 minutes. This adjusts the solvent composition to 35 wt % water. During the addition of water the mixture self-seeded, and the solution was held for approximately 1 hour after complete addition of water. The solids were isolated by filtration, and the wet cake was washed with two 30 mL portions of a rinse solution of 40 wt % water/27 wt % dimethylformamide/33 wt % acetonitrile and then once with 40 mL of water.

Aqueous Washing:

A 500-L jacketed cylindrical reactor equipped with an overhead stirrer and polytetrafluoroethylene (PTFE) baffle to aid in vertical mixing was charged with the wet cake and 133 g of ethyl acetate (8× theoretical mass of product, 150 mL). The mixture was stirred to dissolve the substrate and the solution was washed twice with 40 mL portions of water.

Concentration and Crystallization:

A constant-volume distillation was conducted with heptanes, in vacuo (ca 100 mmHg, jacket temperature of 50° C.), to adjust the solvent composition to approximately 12 wt % ethyl acetate/88 wt % heptanes. During the distillation, solids begin to crystallize out of the solution. Once the distillation was complete, the solution was cooled to ambient temperature (23° C.). The solids were isolated by filtration and the wet cake was washed with a 50-mL portions heptane. The wet cake was dried to give the final product (14.0 g). The solids were 98.1% pure by HPLC analysis and 100% potent vs. reference standard, for an isolated yield of 85%.

Example 3-2

Alternative preparation of 6-(3-tert-butyl-5-(2,4-dioxo-3,4-dihydropyrimidin-1(2H)-yl)-2-methoxyphenyl)naphthalen-2-yl 1,1,2,2,3,3,4,4,4-nonafluorobutane-1-sulfonate (compound (5a))

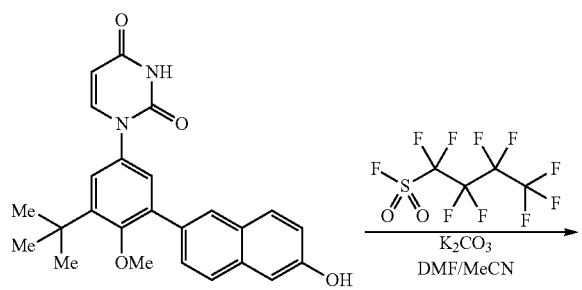

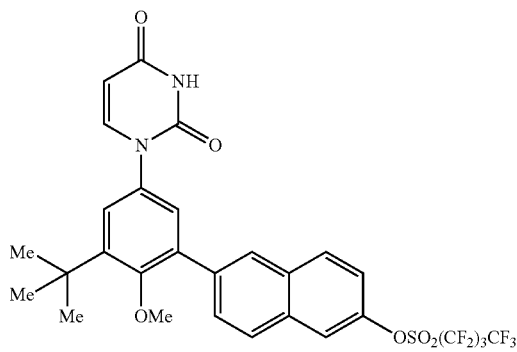

A reactor was equipped with an overhead stirrer and charged with 8.04 g of 1-(3-tert-butyl-5-(6-hydroxynaphthalen-2-yl)-4-methoxyphenyl)pyrimidine-2,4(1H,3H)-dione (19.2 mmol, 1.0 equivalent) and 5.28 g of 325-mesh potassium carbonate (38.4 mmol, 2.0 equivalents). The flask was charged with 33 mL of N,N-dimethylformamide and 51 mL of acetonitrile and the slurry was stirred. Perfluorobutanesulfonyl fluoride (7.16 g, 23.7 mmol, 1.2 equivalents) was added over 1.5 hours, and the mixture was stirred for an hour. The inorganic solids were separated by filtration, and the flask and filter cake were rinsed with a mixture of 4.8 mL of N,N-dimethylformamide and 7.2 mL of acetonitrile. With stirring, 6.0 g of water was added to the organic solution and the mixture was allowed to stir for 30 minutes to allow solids to crystallize. An additional 34 mL of water was added to the slurry over 1 hour, and the mixture was allowed to stir for 2 hours. The wet cake was isolated by filtration with recirculation of the liquors to recover all the solids. The wet cake was washed with a pre-mixed solution of 6.5 mL of N,N-dimethylformamide, 8.0 mL of acetonitrile and 9.5 mL of water.

The wet cake was dissolved in 65 mL of ethyl acetate. The resultant organic solution was washed twice with 33 mL portions of a 5 wt % aqueous sodium chloride solution. The organic solution was filtered into a reactor and the filter rinsed with 25 mL of ethyl acetate. The bulk of the solvent was removed by distillation at approximately 90 torr with heating to 40° C. until the total volume was approximately 25 mL. The slurry was heated to 53° C. and 10 mL of ethyl acetate was added to completely dissolve the precipitated solids. Heptanes (125 mL) were added to the warm (55° C.) slurry over 40 minutes. The mixture was cooled to room temperature over an hour with stirring and the slurry was stirred at ambient temperature for 17 hours. The desired product was isolated by filtration, with recycling of the liquors to isolate all of the solids material. The wet cake was washed with 22 mL of heptanes. The wet cake was dried in a vacuum oven at 50° C. with a gentle nitrogen sweep. The title compound was isolated as a white solid (10.4 g, 77% yield). $^1$H NMR (600 MHz, DMSO-$d_6$) δ ppm 11.42 (s, 1H), 8.21-8.15 (m, 4H), 7.84 (dd, J=8.6, 1.7 Hz, 1H), 7.77 (d, J=7.9 Hz, 1H), 7.60 (dd, J=9.0, 2.5 Hz, 1H), 7.39 (d, J=2.7 Hz, 1H), 7.35 (d, J=2.7 Hz, 1H), 5.66 (d, J=7.9 Hz, 1H), 3.21 (s, 3H), 1.41 (s, 9H).

Example 3-3

Preparation of 6-(3-tert-butyl-5-(2,4-dioxo-3,4-dihydropyrimidin-1(2H)-yl)-2-methoxyphenyl)naphthalen-2-yl 1,1,2,2,3,3,-heptafluoropropane-1-sulfonate (compound (5b))

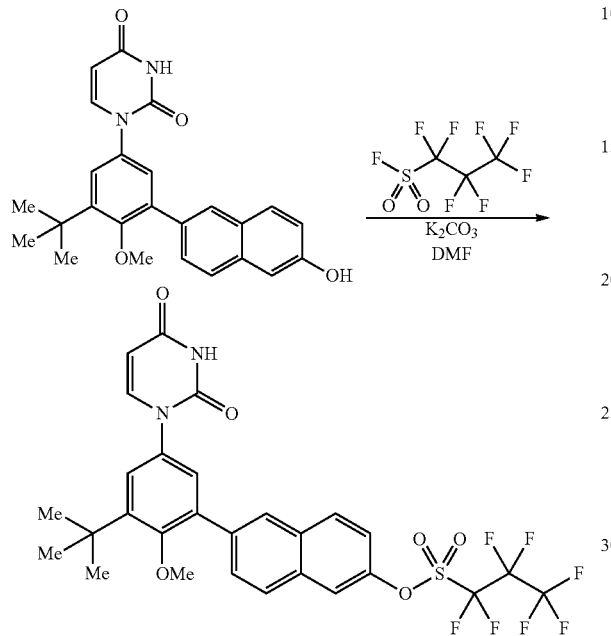

To a stirred solution of 6.0 g of 1-(3-tert-butyl-5-(6-hydroxynaphthalen-2-yl)-4-methoxyphenyl)pyrimidine-2,4 (1H,3H)-dione (14.4 mmol, 1.0 equivalent) in 60 mL of N,N-dimethylformamide was added 4.0 g of 325-mesh potassium carbonate (29 mmol, 2.0 equivalents). 1,1,2,2,3,3,3-heptafluoropropane-1-sulfonyl fluoride (3.85 g, 15.3 mmol, 1.06 equivalents) was added over 20 minutes, and the mixture was stirred for 3 hours. The inorganic solids were separated by filtration, and the flask and filter cake were rinsed with 75 mL of ethyl acetate. The solution was diluted with an additional 75 mL of ethyl acetate and the resultant solution was washed four times with 50 mL portions of 10 wt % aqueous sodium chloride, followed by 50 mL of saturated aqueous sodium chloride solution. The organic solution was dried over sodium sulfate, the drying agent was filtered off and the organic solution was concentrated in vacuo. The resultant oil was dissolved in 5.8 mL of ethyl acetate and 90 mL of heptanes was added over 25 minutes. The product crystallized and was isolated by filtration. The wet cake was washed with 20 mL of heptanes and dried in vacuo with heating at 50° C. The title compound was isolated as a white solid (8.43 g, 90% yield). $^1$H NMR (400 MHz, CDCl$_3$) δ ppm 8.66 (s, 1H), 8.04 (s, 1H), 7.95 (d, J=9.5 Hz, 1H), 7.93 (d, J=9.1 Hz, 1H), 7.83 (dd, J=8.5, 1.7 Hz, 1H), 7.79 (d, J=2.4 Hz, 1H), 7.41 (dd, J=8.9, 2.5 Hz, 1H), 7.36 (d, J=7.9 Hz, 1H), 7.27-7.24 (m, 2H), 5.82 (dd, J=7.9, 2.2 Hz, 1H), 3.30 (s, 3H), 1.46 (s, 9H). $^{13}$C NMR (101 MHz, CDCl$_3$) δ ppm 162.6 (C), 157.5 (C), 149.9 (C), 147.2 (C), 145.0 (C), 144.5 (CH), 137.2 (C), 135.1 (C), 133.0 (C), 132.2 (C), 132.2 (C), 130.5 (CH), 128.5 (CH), 128.1 (CH), 127.4 (CH), 127.2 (CH), 124.4 (CH), 119.9 (CH), 118.9 (CH), 102.4 (CH), 60.9 (CH$_3$), 35.8 (C), 30.8 (CH$_3$). $^{19}$F NMR (564 MHz, DMSO-d$_6$) δ ppm −79.9 (3F), −109.9 (2F), −124.0 (2F). LC-MS m/z 649.1 [M+H]$^+$.

Example 3-4

Preparation of 6-(3-tert-butyl-5-(2,4-dioxo-3,4-dihydropyrimidin-1(2H)-yl)-2-methoxyphenyl)naphthalen-2-yl 1,1,1,2,3,3,3-heptafluoropropane-2-sulfonate (compound (5c))

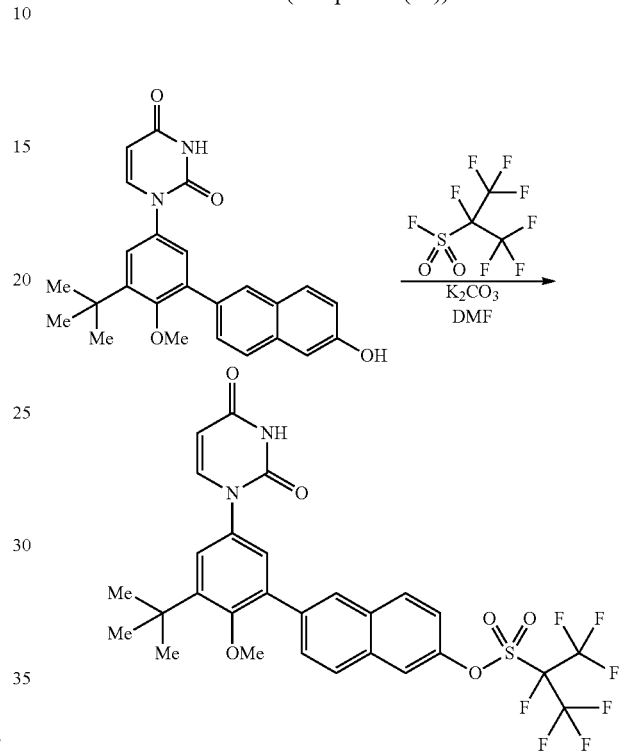

To a stirred solution of 6.0 g of 1-(3-tert-butyl-5-(6-hydroxynaphthalen-2-yl)-4-methoxyphenyl)pyrimidine-2,4 (1H,3H)-dione (14.4 mmol, 1.0 equivalent) in 60 mL of N,N-dimethylformamide was added 4.0 g of 325-mesh potassium carbonate (29 mmol, 2.0 equivalents). 1,1,1,2,3,3,3-heptafluoropropane-2-sulfonyl fluoride (3.6 g, 14.3 mmol, 1.0 equivalents) was added over 30 minutes, and the mixture was stirred for 2 hours. An additional portion of 1,1,1,2,3,3,3-heptafluoropropane-2-sulfonyl fluoride (0.21 g, 0.83 mmol, 0.06 equivalents) was added, and the mixture was stirred for 1.5 hours. The inorganic solids were separated by filtration, and the flask and filter cake were rinsed with 75 mL of ethyl acetate. The solution was diluted with an additional 75 mL of ethyl acetate and the resultant solution was washed four times with 50 mL portions of 10 wt % aqueous sodium chloride, followed by 50 mL of saturated aqueous sodium chloride solution. The organic solution was dried over sodium sulfate, the drying agent was filtered off and the organic solution was concentrated in vacuo. The resultant oil was dissolved in 7 mL of ethyl acetate, which resulted in crystallization after stirring for a few minutes. Heptanes (90 mL) were added slowly to the stirred mixture. The product was isolated by filtration, washed with 20 mL of heptanes and dried in vacuo with heating at 50° C. The title compound was isolated as a white solid (8.30 g, 89% yield). $^1$H NMR (400 MHz, CDCl$_3$) δ ppm 8.05 (s, 1H), 7.95 (d, J=9.6 Hz, 1H), 7.93 (d, J=9.6 Hz, 1H), 7.83 (dd, J=8.5, 1.7 Hz, 1H), 7.78 (d, J=2.4 Hz, 1H), 7.40 (dd, J=8.9, 2.4 Hz, 1H), 7.36 (d, J=7.9 Hz, 1H), 7.27-7.23 (m, 2H), 5.81 (d, J=7.9 Hz, 1H), 3.29 (s, 3H), 1.46 (s, 9H) (NH not observed in this spectrum). $^{13}$C NMR (101 MHz, CDCl$_3$) δ ppm 162.7 (C), 157.5 (C), 149.8 (C), 146.9 (C), 145.0 (C), 144.5 (CH), 137.2 (C), 135.1 (C), 133.0 (C), 132.2 (C), 132.2 (C), 130.5 (CH), 128.5 (CH), 128.1 (CH), 127.4 (CH), 127.2 (CH), 124.4 (CH), 119.9 (CH), 118.9 (CH), 102.4 (CH), 60.9 (CH$_3$), 35.8 (C), 30.8 (CH$_3$). $^{19}$F NMR (564 MHz, DMSO) δ ppm −71.08 (6F), −167.87 (1F). LC-MS m/z 649.1 [M+H]$^+$.

Example 3-5

Preparation of 6-(3-tert-butyl-5-(2,4-dioxo-3,4-dihydropyrimidin-1(2H)-yl)-2-methoxyphenyl)naphthalen-2-yl 1,1,2,2,2-pentafluoroethanesulfonate (compound (5d))

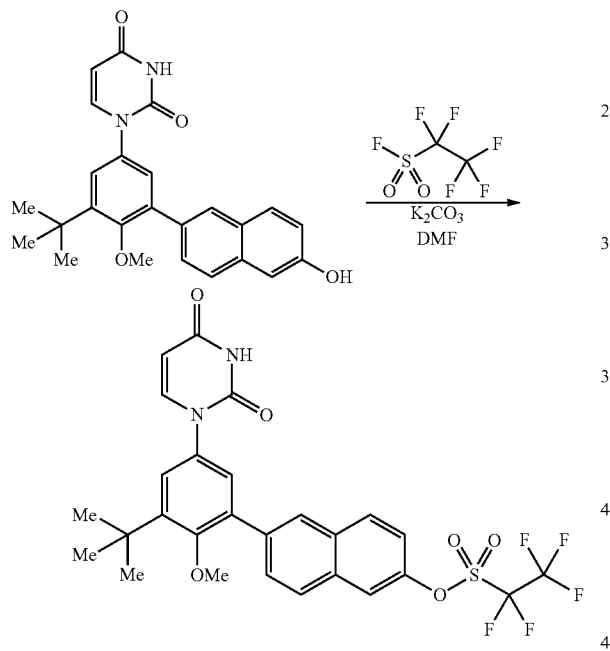

To a stirred solution of 10.0 g of 1-(3-tert-butyl-5-(6-hydroxynaphthalen-2-yl)-4-methoxyphenyl)pyrimidine-2,4 (1H,3H)-dione (23.5 mmol, 1.0 equivalent) in 100 mL of N,N-dimethylformamide was added 6.5 g of 325-mesh potassium carbonate (47 mmol, 2.0 equivalents). 1,1,2,2,2-pentafluoroethanesulfonyl fluoride (4 g, 20 mmol, 0.85 equivalents) was bubbled sub-surface into the reaction mixture over 3 hours, and the mixture was stirred for 0.5 hours. The inorganic solids were separated by filtration, and the flask and filter cake were rinsed with 5 mL of N,N-dimethylformamide. The solution was diluted with 24 mL of water and 150 mL of ethyl acetate and the resultant solution was washed four times with 50 mL portions of 10 wt % aqueous sodium chloride, followed by 25 mL of saturated aqueous sodium chloride solution. The organic solution was dried over sodium sulfate, the drying agent was filtered off and the organic solution was concentrated in vacuo. The resultant solid was purified by chromatography over silica gel with gradient elution (40% ethyl acetate/hexanes to 60% ethyl acetate/hexanes). The desired product was dissolved in 10 mL of ethyl acetate and 200 mL of heptanes was added over 60 minutes. The product crystallized and was isolated by filtration. The wet cake was washed with 40 mL of heptanes and dried in vacuo with heating at 50° C. The title compound was isolated as a white solid (9.4 g, 67% yield). $^1$H NMR (600 MHz, CDCl$_3$) δ ppm 8.60 (d, J=0.5 Hz, 1H), 8.06 (d, J=0.8 Hz, 1H), 7.97 (d, J=9.1 Hz, 1H), 7.94 (d, J=8.7 Hz, 1H), 7.84 (dd, J=8.5, 1.7 Hz, 1H), 7.80 (d, J=2.5 Hz, 1H), 7.42 (dd, J=9.0, 2.5 Hz, 1H), 7.37 (d, J=8.0 Hz, 1H), 7.27-7.26 (m, 2H), 5.82 (dd, J=8.0, 2.3 Hz, 1H), 3.30 (s, 3H), 1.46 (s, 9H). $^{13}$C NMR (101 MHz, CDCl$_3$) δ ppm 162.6 (C), 157.5 (C), 149.8 (C), 147.1 (C), 145.0 (C), 144.5 (CH), 137.2 (C), 135.1 (C), 133.0 (C), 132.23 (C), 132.18 (C), 130.5 (CH), 128.5 (CH), 128.1 (CH), 127.4 (CH), 127.2 (CH), 124.4 (CH), 119.9 (CH), 118.9 (CH), 102.4 (CH), 61.0 (CH$_3$), 35.8 (C), 30.8 (CH$_3$). $^{19}$F NMR (564 MHz, CDCl$_3$) δ ppm −79.1 (3F), −113.4 (2F). LC-MS m/z 599.1 [M+H]$^+$.

Example 3-6

Preparation of 6-(3-tert-butyl-5-(2,4-dioxo-3,4-dihydropyrimidin-1(2H)-yl)-2-methoxyphenyl)naphthalen-2-yl trifluoromethanesulfonate (compound (5e))

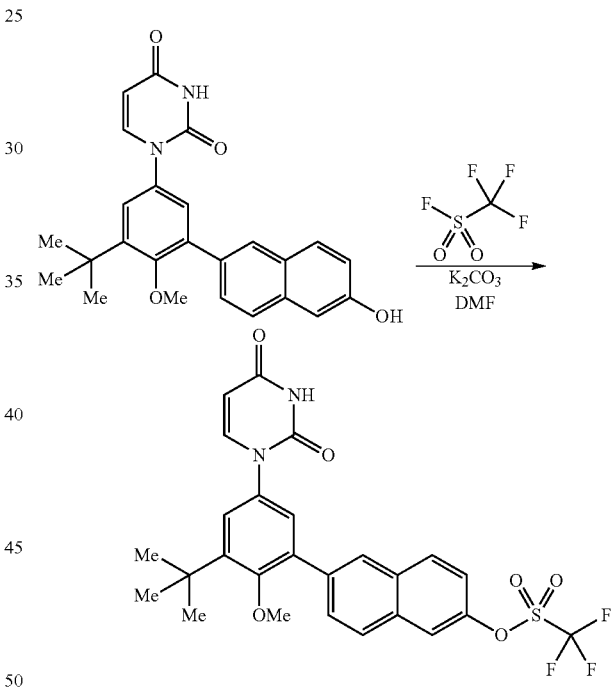

To a stirred solution of 9.0 g of 1-(3-tert-butyl-5-(6-hydroxynaphthalen-2-yl)-4-methoxyphenyl)pyrimidine-2,4 (1H,3H)-dione (21.1 mmol, 1.0 equivalent) in 90 mL of N,N-dimethylformamide was added 5.9 g of 325-mesh potassium carbonate (42.8 mmol, 2.0 equivalents). Trifluoromethanesulfonyl fluoride was bubbled sub-surface into the reaction mixture slowly over 1 hour until the starting material was no longer detected by HPLC. The inorganic solids were separated by filtration, and the flask and filter cake were rinsed with 50 mL of ethyl acetate. The solution was diluted with 50 mL of ethyl acetate and the resultant solution was washed three times with 50 mL portions of 10 wt % aqueous sodium chloride, followed by 50 mL of saturated aqueous sodium chloride solution. The organic solution was dried over sodium sulfate, the drying agent was filtered off and the organic solution was concentrated in vacuo. The resultant oil was solidified by adding 70 mL of 10% ethyl acetate/heptanes and holding for 16 hours. The product was isolated by filtration. The wet cake was washed with 25 mL of 10% ethyl acetate/heptanes and dried in vacuo with heating at 50° C. The title compound was isolated as a white solid (10.8 g, 93% yield). $^1$H NMR (600 MHz, CDCl$_3$) δ ppm 8.63 (s, 1H), 8.06 (d, J=0.8 Hz, 1H), 7.97 (d, J=9.1 Hz, 1H), 7.94 (d, J=8.6 Hz, 1H), 7.84 (dd, J=8.5, 1.7 Hz, 1H), 7.79 (d, J=2.5 Hz, 1H), 7.41 (dd, J=9.0, 2.5 Hz, 1H), 7.37 (d, J=7.9 Hz, 1H), 7.27-7.26 (m, 2H), 5.82 (dd, J=7.9, 2.3 Hz, 1H), 3.30 (s, 3H), 1.46 (s, 9H). $^{13}$C NMR (101 MHz, CDCl$_3$) δ ppm 162.7 (C), 157.5 (C), 149.9 (C), 147.0 (C), 145.0 (C), 144.5 (CH), 137.2 (C), 135.1 (C), 133.0 (C), 132.2 4 (C), 132.19 (C), 130.5 (CH), 128.5 (CH), 128.0 (CH), 127.4 (CH), 127.2 (CH), 124.4 (CH), 119.9 (CH), 118.9 (CH), 102.4 (CH), 61.0 (CH$_3$), 35.8 (C), 30.8 (CH$_3$). $^{19}$F NMR (564 MHz, CDCl$_3$) δ ppm −72.8 (3F). LC-MS m/z 549.2 [M+H]$^+$.

Example 3-7

Preparation of 6-(3-tert-butyl-5-(2,4-dioxo-3,4-dihydropyrimidin-1(2H)-yl)-2-methoxyphenyl)naphthalen-2-yl 1,1,2,2-tetrafluoro-2-(perfluoroethoxy)ethanesulfonate (compound (5f))

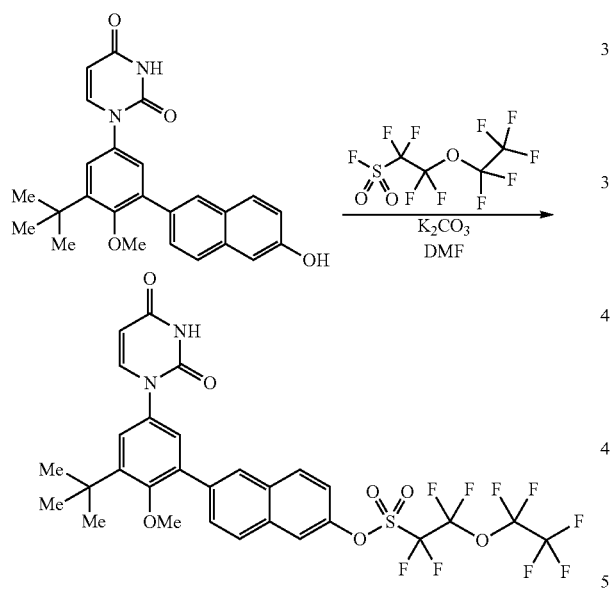

To a stirred solution of 0.53 g of 1-(3-tert-butyl-5-(6-hydroxynaphthalen-2-yl)-4-methoxyphenyl)pyrimidine-2,4(1H,3H)-dione (1.27 mmol, 1.0 equivalent) in 5 mL of N,N-dimethylformamide was added 0.35 g of 325-mesh potassium carbonate (2.6 mmol, 2.0 equivalents). Perfluoro (2-ethoxyethane)sulfonyl fluoride (0.46 g, 1.4 mmol, 1.1 equivalents) was added in one portion, and the mixture was stirred for an hour. The inorganic solids were separated by filtration, and the flask and filter cake were rinsed with 1 mL of N,N-dimethylformamide followed by 2 mL of ethyl acetate. The solution was diluted with 30 mL of ethyl acetate and the resultant solution was washed twice with 20 mL portions of 10 wt % aqueous sodium chloride, followed by 20 mL of saturated aqueous sodium chloride solution. The washing procedure was repeated once. The organic solution was dried over sodium sulfate, the drying agent was filtered off and the organic solution was concentrated in vacuo. The resultant solid was purified by chromatography over silica gel with gradient elution (30% ethyl acetate/hexanes to 60% ethyl acetate/hexanes). The title compound was isolated as a white solid (0.76 g, 84% yield). $^1$H NMR (400 MHz, CDCl$_3$) δ ppm 8.54 (d, J=1.7 Hz, 1H), 8.04 (s, 1H), 7.95 (d, J=9.4 Hz, 1H), 7.92 (d, J=10.1 Hz, 1H), 7.83 (dd, J=8.5, 1.7 Hz, 1H), 7.78 (d, J=2.4 Hz, 1H), 7.40 (dd, J=9.0, 2.5 Hz, 1H), 7.36 (d, J=7.9 Hz, 1H), 7.27-7.23 (m, 2H), 5.81 (dd, J=7.9, 2.4 Hz, 1H), 3.29 (s, 3H), 1.46 (s, 9H). $^{13}$C NMR (101 MHz, CDCl$_3$) δ ppm 162.6 (C), 157.5 (C), 149.8 (C), 147.1 (C), 145.0 (C), 144.5 (CH), 137.2 (C), 135.1 (C), 133.0 (C), 132.2 (C), 132.2 (C), 130.5 (CH), 128.5 (CH), 128.1 (CH), 127.4 (CH), 127.2 (CH), 124.4 (CH), 119.9 (CH), 118.9 (CH), 102.4 (CH), 60.9 (CH$_3$), 35.8 (C), 30.8 (CH$_3$). $^{19}$F NMR (564 MHz, CDCl$_3$) δ ppm −81.61 (2F), −86.42 (3F), −88.11 (2F), −112.90 (2F). LC-MS m/z 715.0 [M+H]$^+$.

Example 3-8

Preparation of 6-(3-tert-butyl-5-(2,4-dioxo-3,4-dihydropyrimidin-1(2H)-yl)-2-methoxyphenyl)naphthalen-2-yl sulfofluoridate (compound (5g))

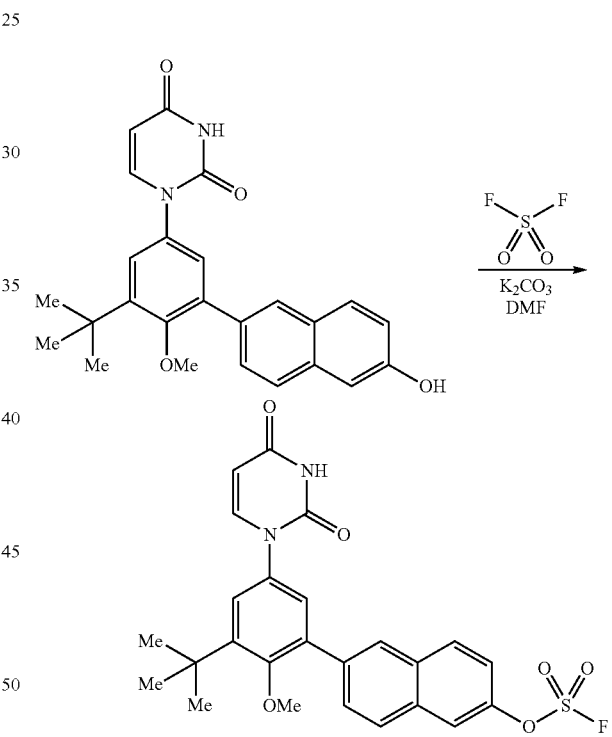

To a stirred solution of 5.1 g of 1-(3-tert-butyl-5-(6-hydroxynaphthalen-2-yl)-4-methoxyphenyl)pyrimidine-2,4(1H,3H)-dione (12.2 mmol, 1.0 equivalent) in 50 mL of N,N-dimethylformamide at ambient temperature was added 3.3 g of 325-mesh potassium carbonate (24 mmol, 2.0 equivalents). The reaction flask was equipped with a dry ice/acetone condenser and sulfuryl fluoride was bubbled sub-surface into the reaction mixture slowly over 10 minutes. HPLC analysis at that time indicated no starting material remained. The mixture was allowed to stir for an additional 1 hour. The solution was sparged sub-surface with nitrogen gas to purge any residual sulfuryl fluoride from the reactor, and the inorganic solids were separated by filtration. The DMF solution was diluted with 125 mL of ethyl acetate and the resultant solution was washed four times with 50 mL portions of 10 wt % aqueous sodium chloride, followed by 50 mL of saturated aqueous sodium chloride solution. The organic solution was dried over sodium sulfate, the drying agent was filtered off and the organic solution was concentrated in vacuo. The resultant oil was crystallized by adding 2 mL of ethyl acetate, followed by 75 mL of heptanes slowly over several hours. The resultant slurry was mixed for 16 hours, and the product was isolated by filtration. The wet cake was washed with heptanes and dried in vacuo with heating at 50° C. The title compound was isolated as a white solid (5.7 g, 95% yield). $^1$H NMR (600 MHz, DMSO-d$_6$) δ ppm 11.40 (d, J=2.0 Hz, 1H), 8.29 (d, J=2.4 Hz, 1H), 8.26-8.22 (m, 2H), 8.18 (d, J=8.6 Hz, 1H), 7.87 (dd, J=8.6, 1.7 Hz, 1H), 7.79 (d, J=7.9 Hz, 1H), 7.75 (dd, J=9.1, 2.5 Hz, 1H), 7.41 (d, J=2.7 Hz, 1H), 7.36 (d, J=2.7 Hz, 1H), 5.66 (dd, J=7.9, 2.3 Hz, 1H), 3.24 (s, 3H), 1.43 (s, 9H). $^{13}$C NMR (101 MHz, DMSO-d$_6$) δ ppm 163.0 (C), 156.0 (C), 149.9 (C), 146.9 (C), 145.2 (CH), 143.0 (C), 136.9 (C), 133.7 (C), 133.6 (C), 131.9 (C), 131.6 (C), 130.9 (CH), 128.1 (CH), 128.0 (CH), 127.6 (CH), 126.8 (CH), 124.8 (CH), 119.2 (CH), 118.4 (CH), 101.1 (CH), 60.5 (CH$_3$), 35.1 (C), 30.5 (CH$_3$). $^{19}$F NMR (564 MHz, DMSO-d$_6$) δ ppm 38.9 (F). LC-MS m/z 499.15 [M+H]$^+$.

Example 3-9

Preparation of 6-(3-tert-butyl-5-(2,4-dioxo-3,4-dihydropyrimidin-1(2H)-yl)-2-methoxyphenyl)naphthalen-2-yl methanesulfonate (compound (5h))

dride (4 mmol, 0.3 equiv) was added to the mixture. The reaction mixture was quenched by the addition of 30 mL of water with stirring. The resultant heterogeneous mixture was dissolved in 150 mL of ethyl acetate, and the resultant solution was washed five times with 50 mL portions of 10 wt % aqueous sodium chloride. The organic solution was dried over sodium sulfate, the drying agent was filtered off and the organic solution was concentrated in vacuo. The resultant oil was solidified by holding in a refrigerator and purified by slurrying in 20 mL of ethyl acetate. The product was isolated by filtration, the wet cake was washed with ethyl acetate and dried in vacuo with heating at 50° C. The title compound was isolated as a white solid (4.5 g, 91% potent, 69% yield). $^1$H NMR (400 MHz, DMSO-d$_6$) δ ppm 11.36 (d, J=1.4 Hz, 1H), 8.12 (s, 1H), 8.08 (d, J=9.1 Hz, 1H), 8.05 (d, J=8.7 Hz, 1H), 7.94 (d, J=2.3 Hz, 1H), 7.79-7.72 (m, 2H), 7.49 (dd, J=8.9, 2.4 Hz, 1H), 7.34 (d, J=2.6 Hz, 1H), 7.29 (d, J=2.7 Hz, 1H), 5.61 (dd, J=7.9, 1.9 Hz, 1H), 3.43 (s, 3H), 3.20 (s, 3H), 1.39 (s, 9H). $^{13}$C NMR (101 MHz, DMSO-d$_6$) δ ppm 163.0 (C), 156.0 (C), 150.0 (C), 146.4 (C), 145.2 (CH), 143.0 (C), 135.9 (C), 134.0 (C), 133.6 (C), 131.9 (C), 131.3 (C), 130.0 (CH), 127.7 (CH), 127.6 (CH), 127.5 (CH), 126.7 (CH), 124.6 (CH), 121.3 (CH), 119.0 (CH), 101.1 (CH), 60.4 (CH$_3$), 37.6 (CH$_3$), 35.1 (C), 30.5 (CH$_3$). LC-MS m/z 495.1 [M+H]$^+$.

Example 4

Preparation of N-(6-(3-tert-butyl-5-(2,4-dioxo-3,4-dihydropyrimidin-1(2H)-yl)-2-methoxyphenyl)naphthalen-2-yl)methanesulfonamide (compound (A-1))

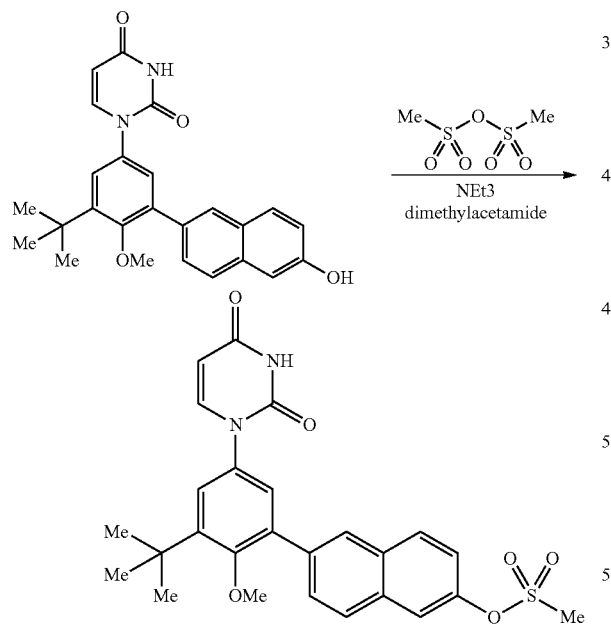

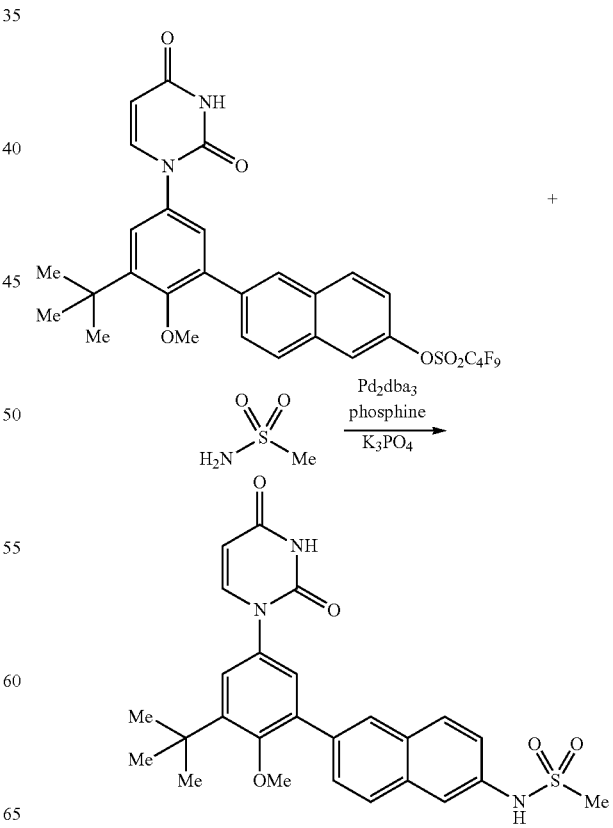

To a stirred slurry of 5.0 g of 1-(3-tert-butyl-5-(6-hydroxynaphthalen-2-yl)-4-methoxyphenyl)pyrimidine-2,4 (1H,3H)-dione (12.0 mmol, 1.0 equivalent) in 25 mL of N,N-dimethylacetamide was added 4.4 g of methanesulfonic anhydride (25 mmol, 2.1 equivalents). The solution was cooled in a water bath to keep the internal temperature below 30° C. during the addition of 8.5 mL of triethylamine (61 mmol, 5.1 equivalents). After stirring for 2.5 hours at room temperature, an additional 0.70 g of methanesulfonic anhy- A 3-L, 3-neck, round-bottom flask was equipped with an overhead stirrer, a thermocouple, a Claisen condenser and a reflux condenser. Tris(dibenzylideneacetone)dipalladium(0) (0.330 g, 0.360 mmol), di-tert-butyl(2',4',6'-triisopropyl-3,4,5,6-tetramethylbiphenyl-2-yl)phosphine (0.416 g, 0.864 mmol) and milled potassium phosphate tribasic (21.0 g, 99.0 mmol) were charged to the 3-L flask. The flask was purged with argon for not less than 90 minutes with constant stirring of the solids. t-Amyl alcohol (250 ml) was charged to a separate 500-mL round-bottom flask and was purged with argon for not less than 30 minutes and was transferred to the 3-L flask using a cannula under argon atmosphere. The contents of the 3-L flask were heated to 80° C. and stirred at this temperature for 30 minutes. A 1-L round-bottom flask equipped with a magnetic stir bar was charged with 6-(3-tert-butyl-5-(2,4-dioxo-3,4-dihydropyrimidin-1(2H)-yl)-2-methoxyphenyl)naphthalen-2-yl 1,1,2,2,3,3,4,4,4-nonafluorobutane-1-sulfonate (62.9 g, 90 mmol), methanesulfonamide (12.85 g, 135 mmol) and t-amyl alcohol (505 mL), purged with argon and heated to 60° C. The reagent mixture was stirred under argon for not less than 30 minutes. A clear yellow solution was observed. This solution was transferred to the 3-L flask using a cannula under argon atmosphere. The temperature of the 3-L flask was raised to 85° C. and the contents were stirred for 14 hours under a positive pressure of argon. The temperature was then raised to 95° C. and the contents were stirred for an additional 4 hours under a positive pressure of argon. The reaction mixture was allowed to cool down to room temperature, diluted with tetrahydrofuran (2200 mL) and water (800 mL) and was transferred to a 6-L separatory funnel. The organic layer was washed thrice with water (2000 mL) containing L-cysteine (17.3 g) and NaCl (235 g). The organic layer was collected, filtered through a pad of diatomaceous earth and was concentrated in vacuo to approximately 250 mL. Ethyl acetate (775 mL) was added over 7 hours with stirring, and the mixture was allowed to stir for an additional 14 hours. White solid was isolated by filtration, and the solid was washed with ethyl acetate (1000 mL). The solid was dissolved in tetrahydrofuran (1500 mL) and filtered through a pad of diatomaceous earth to obtain a clear solution. The diatomaceous earth was washed with tetrahydrofuran (300 mL). The combined tetrahydrofuran solution was concentrated in vacuo to approximately 250 mL, and then ethyl acetate (775 mL) was added over 7 hours with stirring. The product solution was allowed to stir for an additional 14 hours. White solid was isolated by filtration. The solid was washed with ethyl acetate (1000 mL) and dried in a vacuum oven at 60° C. for 24 hours. The solid was slurried in 308 mL of 200 proof ethanol for 1.5 hours, then isolated by filtration. The solid was washed with 132 mL of 200 proof ethanol and dried in a vacuum oven at 50° C. for 18 hours. The title compound was isolated as a white solid (32.6 g, 100% potency vs. standard, 73% yield). $^1$H NMR (400 MHz, DMSO-$d_6$) δ ppm 11.41 (d, J=2.1 Hz, 1H), 10.04 (s, 1H), 8.02 (d, J=0.9 Hz, 1H), 7.98-7.91 (m, 2H), 7.79 (d, J=7.9 Hz, 1H), 7.72 (d, J=2.0 Hz, 1H), 7.69 (dd, J=8.5, 1.7 Hz, 1H), 7.41 (dd, J=8.8, 2.2 Hz, 1H), 7.36 (d, J=2.7 Hz, 1H), 7.31 (d, J=2.7 Hz, 1H), 5.65 (dd, J=7.9, 2.2 Hz, 1H), 3.24 (s, 3H), 3.08 (s, 3H), 1.42 (s, 9H). $^{13}$C NMR (101 MHz, DMSO-$d_6$) δ ppm 163.1 (C), 156.0 (C), 150.0 (C), 145.3 (CH), 142.9 (C), 136.0 (C), 134.3 (C), 134.2 CO, 133.5 (C), 132.2 (C), 129.5 (C), 129.0 (CH), 127.6 (CH), 127.1 (CH), 127.0 (CH), 126.5 (CH), 124.3 (CH), 120.2 (CH), 114.5 (CH), 101.1 (CH), 60.3 (CH$_3$), 39.4 (CH$_3$), 35.1 (C), 30.5 (CH$_3$).

Other ligands such as 2,2,7,7-tetramethyl-1-(2',4',6'-triisopropylbiphenyl-2-yl)phosphepane; 7,7,9,9-tetramethyl-8-(2',4',6'-triisopropyl-3,6-dimethoxybiphenyl-2-yl)-1,4-dioxa-8-phosphaspiro[4.5]decane; and 8-(2-(2-methoxynaphthalen-1-yl)phenyl)-7,7,9,9-tetramethyl-1,4-dioxa-8-phosphaspiro[4.5]decane were tested under the conditions described above and produced favorable yields of greater than 50% of the sulfonamidated product.

TABLE 1

Alternative Ligands for Sulfonamidation

| Pd (mol %) | Ligand (mol %) |
|---|---|
| 1 | 7,7,9,9-tetramethyl-8-(2',4',6'-triisopropylbiphenyl-2-yl)-1,4-dioxa-8-phosphaspiro[4.5]decane (1.2) |
| 1 | 2,2,6,6-tetramethyl-1-(2',4',6'-triisopropylbiphenyl-2-yl)phosphinane (1.2) |
| 1 | 8,8,10,10-tetramethyl-9-(2',4',6'-triisopropylbiphenyl-2-yl)-1,5-dioxa-9-phosphaspiro[5.5]undecane (1.2) |
| 1 | 2,2,6,6-tetramethyl-1-(2',4',6'-triisopropylbiphenyl-2-yl)phosphinan-4-ol (1.2) |
| 1 | 8-(2',6'-diisopropoxybiphenyl-2-yl)-7,7,9,9-tetramethyl-1,4-dioxa-8-phosphaspiro[4.5]decane (1.2) |
| 1 | 1,3,5,7-tetramethyl-8-(2',4',6'-triisopropylbiphenyl-2-yl)-2,4,6-trioxa-8-phosphatricyclo[3.3.1.1$^{3,7}$]decane (1.2) |
| 1 | 8-(2',6'-dimethoxybiphenyl-2-yl)-7,7,9,9-tetramethyl-1,4-dioxa-8-phosphaspiro[4.5]decane |
| 1 | 6-methoxy-N,N-dimethyl-2'-(7,7,9,9-tetramethyl-1,4-dioxa-8-phosphaspiro[4.5]decan-8-yl)biphenyl-2-amine (1.2) |
| 1 | 8-(2'-methoxy-1,1'-binaphthyl-2-yl)-7,7,9,9-tetramethyl-1,4-dioxa-8-phosphaspiro[4.5]decane (1.2) |
| 1 | 8-(1,1'-binaphthyl-2-yl)-7,7,9,9-tetramethyl-1,4-dioxa-8-phosphaspiro[4.5]decane (1.2) |
| 1 | 7,7,9,9-tetramethyl-8-(2-(naphthalen-1-yl)phenyl)-1,4-dioxa-8-phosphaspiro[4.5]decane (1.2) |
| 1 | 7,7,9,9-tetramethyl-8-(2-(naphthalen-2-yl)phenyl)-1,4-dioxa-8-phosphaspiro[4.5]decane (1.2) |

Example 4-1

Alternative Preparation of N-(6-(3-tert-butyl-5-(2,4-dioxo-3,4-dihydropyrimidin-1(2H)-yl)-2-methoxyphenyl)naphthalen-2-yl)methanesulfonamide (compound (A-1))

A 450-mL, stainless steel Parr® pressure reactor equipped with an overhead stirrer was charged with tris(dibenzylideneacetone)dipalladium(0) (0.131 g, 0.143 mmol), di-tert-butyl(2',4',6'-triisopropyl-3,6-dimethoxybiphenyl-2-yl)

phosphine (0.167 g, 0.344 mmol) and milled potassium phosphate tribasic (6.69 g, 31.5 mmol). The flask was purged with argon for not less than 90 minutes. Tetrahydrofuran (90 mL) was taken in a 100-mL round bottom flask, purged with argon for not less than 30 minutes and was transferred to the 450-mL reactor using a cannula under argon atmosphere. The contents of the 450-mL reactor were heated to 80° C. and stirred at this temperature for 30 minutes. A 250-mL, round-bottom flask equipped with a magnetic stir bar was charged with 6-(3-tert-butyl-5-(2,4-dioxo-3,4-dihydropyrimidin-1(2H)-yl)-2-methoxyphenyl)naphthalen-2-yl 1,1,2,2,3,3,4,4,4-nonafluorobutane-1-sulfonate (20.0 g, 28.6 mmol), methanesulfonamide (3.27 g, 34.4 mmol) and tetrahydrofuran (160 mL), purged with argon for not less than 45 minutes. A clear yellow solution was observed. This solution was transferred to the 450-mL reactor that has been cooled to the room temperature using a cannula under argon atmosphere. The temperature of the 450-mL reactor was raised to 90° C. and the contents were stirred for 20 hours. The reaction mixture was allowed to cool down to 50° C., diluted with tetrahydrofuran (70 mL) and water (70 mL) containing L-cysteine (0.875 g) and sodium chloride (7.7 g). The contents were stirred for 2 hours at 50° C. The aqueous layer was discarded and the organic layer was filtered through an approximately 2-inch pad of diatomaceous earth and rinsed with tetrahydrofuran (45 mL) to obtain a clear, light yellow solution. The total weight of reaction mixture was 363.43 g. HPLC analysis of the reaction mixture revealed 13.71 g (97%) of the title compound was present in the reaction mixture. A portion of the reaction mixture (50 g) was concentrated to a final volume of 12-14 mL under vacuum. Ethyl acetate (45 mL) was added slowly and the reaction mixture was stirred over night at room temperature to obtain white slurry. Product was collected by filtration, washed with ethyl acetate (7 mL) and dried overnight in a vacuum oven at 50-60° C. to obtain 2.02 g of white solid. Ethanol (14 mL) was added to the solid and stirred overnight at the room temperature. The product was collected by filtration, washed with ethanol (4 mL) and dried overnight in a vacuum oven at 50-60° C. to obtain the title compound (1.79 g, 95.4%).

Example 4-2

Alternative preparation of N-(6-(3-tert-butyl-5-(2,4-dioxo-3,4-dihydropyrimidin-1(2H)-yl)-2-methoxyphenyl)naphthalen-2-yl)methanesulfonamide (compound (A-1))

A 450-mL, stainless steel Parr® pressure reactor equipped with an overhead stirrer was charged with tris(dibenzylideneacetone)dipalladium(0) (0.105 g, 0.115 mmol), di-tert-butyl(2',4',6'-triisopropyl-3,6-dimethoxybiphenyl-2-yl)phosphine (0.133 g, 0.275 mmol) and milled potassium phosphate tribasic (5.35 g, 25.2 mmol). The flask was purged with argon for not less than 90 minutes. 2-Methyltetrahydrofuran (70 mL) was taken in a 100-mL round bottom flask, purged with argon for not less than 30 minutes and was transferred to the 450-mL reactor using a cannula under argon atmosphere. The contents of the 450-mL reactor were heated to 80° C. and stirred at this temperature for 30 minutes. A 250-mL, round bottom flask equipped with a magnetic stir bar was charged with 6-(3-tert-butyl-5-(2,4-dioxo-3,4-dihydropyrimidin-1(2H)-yl)-2-methoxyphenyl)naphthalen-2-yl 1,1,2,2,3,3,4,4,4-nonafluorobutane-1-sulfonate (16.0 g, 22.9 mmol), methanesulfonamide (2.61 g, 27.5 mmol) and 2-methyltetrahydrofuran (155 mL), purged with argon for not less than 60 minutes. This solution was transferred to the 450-mL reactor that has been cooled to the room temperature using a cannula under argon atmosphere. The temperature of the 450-mL flask was raised to 90° C. and the contents were stirred for 14 hours. The reaction mixture was allowed to cool down to 70° C., diluted with ethyl acetate (190 mL) and stirred for 3 hours at 70° C., cooled to the room temperature, stirred for an additional 4 hours, filtered through a fine frit filter funnel and rinsed with ethyl acetate (90 mL) to obtain 29.4 g of light brown solid. A portion of this solid (13.04 g) was transferred to a 500-mL, 3-neck round bottom flask equipped with an overhead stirrer and a thermocouple. Tetrahydrofuran (175 mL) was added, followed by the addition of water 50 mL containing L-cysteine (0.63 g) and sodium chloride (5.5 g). The reaction mixture was stirred for 2 hours at 50° C. under a slight positive pressure of argon. The reaction mixture was transferred to a 500-mL separatory funnel and the aqueous layer was discarded. The organic layer was filtered through an approximately 2-inch pad of diatomaceous earth and rinsed with tetrahydrofuran (45 mL) to obtain a clear, light yellow solution. The organic layer was concentrated to a total weight of 45.59 g. A portion of this organic solution (41.58 g) was charged to a 250-mL, 3-neck round bottom flask fitted with an overhead stirrer. Ethyl acetate (80 mL) was added over 6 hours by a pump with constant stirring at room temperature. The product was collected by filtration, rinsed with ethyl acetate (20 mL) and dried in a vacuum oven for 2 hours to obtain 3.17 g of the title compound (>99.8 pure and 94.6% potent vs. standard).

Example 4-3

Alternative preparation of N-(6-(3-tert-butyl-5-(2,4-dioxo-3,4-dihydropyrimidin-1(2H)-yl)-2-methoxyphenyl)naphthalen-2-yl)methanesulfonamide (compound (A-1))

A 600-mL, stainless steel Parr® pressure reactor equipped with an overhead stirrer was charged with tris(dibenzylideneacetone)dipalladium(0) (0.229 g, 0.251 mmol), di-tert-butyl(2',4',6'-triisopropyl-3,6-dimethoxybiphenyl-2-yl)phosphine (0.291 g, 0.601 mmol) and milled potassium phosphate tribasic (11.70 g, 55.1 mmol). The flask was purged with argon for not less than 90 minutes. Ethyl acetate (140 mL) was taken in a 250-mL, round bottom flask, purged with argon for not less than 30 minutes and was transferred to the 600-mL reactor using a cannula under argon atmosphere. The contents of the 600-mL reactor were heated to 80° C. and stirred at this temperature for 30 minutes. A 500-mL round bottom flask equipped with a magnetic stir bar was charged with 6-(3-tert-butyl-5-(2,4-dioxo-3,4-dihydropyrimidin-1(2H)-yl)-2-methoxyphenyl)naphthalen-2-yl 1,1,2,2,3,3,4,4,4-nonafluorobutane-1-sulfonate (35.0 g, 50.1 mmol), methanesulfonamide (5.72 g, 60.1 mmol) and ethyl acetate (280 mL), purged with argon for not less than 60 minutes while stirring at 50° C. This solution was transferred to the 600-mL reactor that had been cooled to room temperature using a cannula under argon atmosphere. The temperature of the 600-mL flask was raised to 90° C., and the contents were stirred for 18 hours. The reaction mixture was allowed to cool down to 40° C., filtered and rinsed with ethyl acetate (140 mL). Solid (41.50 g) was obtained after drying for 2 hours on high vacuum. This solid contained the titled product (23.06 g, 93%).

Example 4-4

Alternative preparation of N-(6-(3-tert-butyl-5-(2,4-dioxo-3,4-dihydropyrimidin-1(2H)-yl)-2-methoxyphenyl)naphthalen-2-yl)methanesulfonamide (compound (A-1))

Tris(dibenzylideneacetone)dipalladium(0) (0.0066 g, 7.16 µmol), di-tert-butyl(2',4',6'-triisopropyl-3,6-dimethoxybiphenyl-2-yl)phosphine (0.0083 g, 17 µmol) and milled potassium phosphate tribasic (0.334 g, 1.58 mmol) were charged to a 40-mL reaction vial inside an inert atmosphere glove box. t-Amyl alcohol (4 mL) was added, the vial was capped, and the contents were heated to 80° C. and stirred at this temperature for 30 minutes. The reaction mixture was cooled down to the room temperature. 6-(3-tert-Butyl-5-(2,4-dioxo-3,4-dihydropyrimidin-1(2H)-yl)-2-methoxyphenyl)naphthalen-2-yl 1,1,2,2,3,3,4,4,4-nonafluorobutane-1-sulfonate (1.0 g, 1.43 mmol), methanesulfonamide (0.163 g, 1.72 mmol) and t-amyl alcohol (8 mL) were added to the 40-mL reaction vial, and the vial was capped. The reaction temperature was raised to 90° C. and the contents were stirred for 5 hours. HPLC analysis of the reaction mixture showed that the product was formed in 94 area % at 210 nm.

Example 4-5

Alternative preparation of N-(6-(3-tert-butyl-5-(2,4-dioxo-3,4-dihydropyrimidin-1(2H)-yl)-2-methoxyphenyl)naphthalen-2-yl)methanesulfonamide (compound (A-1))

A 600-mL, stainless steel, Parr® reactor was equipped with an overhead stirrer, thermocouple and a heating mantle. Tris(dibenzylideneacetone)dipalladium(0) (0.164 g, 0.179 mmol), di-tert-butyl(2',4',6'-triisopropyl-3,6-dimethoxybiphenyl-2-yl)phosphine (0.208 g, 0.429 mmol) and milled potassium phosphate tribasic (8.36 g, 39.4 mmol) were charged to the 600-mL reactor. The reactor was purged with argon for not less than 90 minutes. 2-Methyltetrahydrofuran (100 mL) was purged with argon for not less than 30 minutes and was transferred to the 600-mL reactor using a cannula under argon atmosphere. The reactor was tightly sealed, the contents were heated to 80° C. and stirred at this temperature for 30 minutes. A 500-mL round bottom flask equipped with a magnetic stir bar was charged with 6-(3-tert-butyl-5-(2,4-dioxo-3,4-dihydropyrimidin-1(2H)-yl)-2-methoxyphenyl)naphthalen-2-yl 1,1,2,2,3,3,4,4,4-nonafluorobutane-1-sulfonate (25 g, 35.8 mmol), methanesulfonamide (4.09 g, 42.9 mmol) and ethyl acetate (200 mL), purged with argon for not less than 30 minutes with stirring and heated to 60° C. A clear solution was observed. This solution was transferred to the 600-mL reactor using a cannula under argon atmosphere. The reactor was tightly sealed, the contents were heated to 90° C. and stirred at this temperature for 14 hours. The reaction mixture was cooled to 35° C., solids were collected by filtration, washed with ethyl acetate (300 mL) and dried under high vacuum for 2-4 hours. The solids were then transferred to a 1-L, three-neck, round-bottom flask equipped with an overhead stirrer and a thermocouple. N-Acetyl-L-cysteine (0.58 g, 3.5 mmol), dimethylformamide (DMF) (100 mL) and glacial acetic acid (0.85 g) were charged to the 1-L flask; the contents were heated to 60° C. and mixed for 1 hour. The mixture was filtered through approximately 2-inch pad of diatomaceous earth and washed with DMF (50 mL). The dark-brown/black-colored solid collected on diatomaceous earth was discarded and the light yellow/clear filtrate was charged to a separate 1-L, three-neck, round-bottom flask equipped with an overhead stirrer, a thermocouple and a syringe pump. The DMF solution was mixed and methanol (300 mL) was added over 8 hours, while maintaining the internal temperature at 25±5° C. The white solid was collected by filtration washed with methanol (150 mL) and dried in a vacuum oven at 50° C. for not less than 8 hours. The title compound was isolated as a white solid (15.8 g, 89% yield).

Example 4-6

Alternative preparation of N-(6-(3-tert-butyl-5-(2,4-dioxo-3,4-dihydropyrimidin-1(2H)-yl)-2-methoxyphenyl)naphthalen-2-yl)methanesulfonamide (compound (A-1))

A 600-mL, stainless steel, Parr® reactor was equipped with an overhead stirrer, thermocouple and a heating mantle. Tris(dibenzylideneacetone)dipalladium(0) (0.164 g, 0.179 mmol), 7,7,9,9-tetramethyl-8-(2',4',6'-triisopropyl-3,6-dimethoxybiphenyl-2-yl)-1,4-dioxa-8-phosphaspiro[4.5]decane (0.238 g, 0.429 mmol) and milled potassium phosphate tribasic (8.36 g, 39.4 mmol) were charged to the 600-mL reactor. The reactor was purged with argon for not less than 90 minutes. 2-Methyltetrahydrofuran (100 mL) was purged with argon for not less than 30 minutes and was transferred to the 600-mL reactor using a cannula under argon atmosphere. The reactor was tightly sealed, the contents were heated to 80° C. and stirred at this temperature for 30 minutes. A 500-mL round bottom flask equipped with a magnetic stir bar was charged with 6-(3-tert-butyl-5-(2,4-dioxo-3,4-dihydropyrimidin-1(2H)-yl)-2-methoxyphenyl)naphthalen-2-yl 1,1,2,2,3,3,4,4,4-nonafluorobutane-1-sulfonate (25 g, 35.8 mmol), methanesulfonamide (4.09 g, 42.9 mmol) and ethyl acetate (200 mL), purged with argon for not less than 30 minutes with stirring and heated to 60° C. A clear solution was observed. This solution was transferred to the 600-mL reactor using a cannula under argon atmosphere. The reactor was tightly sealed, the contents were heated to 90° C. and stirred at this temperature for 14 hours. The reaction mixture was cooled to 35° C., 5% aqueous N-acetyl-L-cysteine solution (100 mL) was added and the contents were mixed for 1 hour at 35° C. Solids were collected by filtration, washed with water (2×25 mL) and ethyl acetate (3×80 mL) and were dried under high vacuum for 2-4 hours. The solids were then transferred to a 1-L, three-neck, round-bottom flask equipped with an overhead stirrer and a thermocouple. N-Acetyl-L-cysteine (0.58 g, 3.5 mmol), dimethylformamide (DMF) (100 mL) and glacial acetic acid (0.85 g) were charged to the 1-L flask; the contents were heated to 60° C. and mixed for 1 hour. The mixture was filtered through an approximately 2-inch pad of diatomaceous earth and washed with DMF (50 mL). The dark-brown/black-colored solid collected on the diatomaceous earth was discarded and the light yellow/clear filtrate was charged to a separate 1-L, three-neck, round-bottom flask equipped with an overhead stirrer, a thermocouple and a syringe pump. The DMF solution was mixed and methanol (300 mL) was added over 8 hours, while maintaining the internal temperature at 25±5° C. The white solid was collected by filtration washed with methanol (150 mL) and dried in a vacuum oven at 50° C. for not less than 8 hours. The title compound was isolated as a white solid (15.6 g, 88% yield).

Example 4-7

Alternative preparation of N-(6-(3-tert-butyl-5-(2,4-dioxo-3,4-dihydropyrimidin-1(2H)-yl)-2-methoxyphenyl)naphthalen-2-yl)methanesulfonamide (compound (A-1))

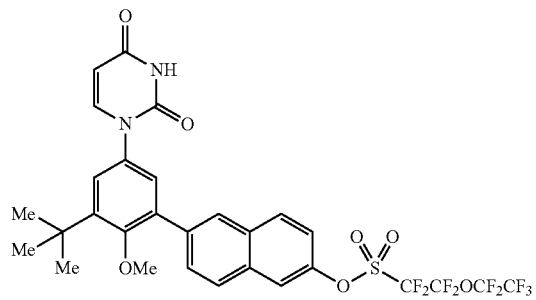

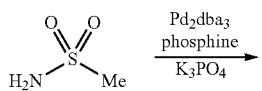

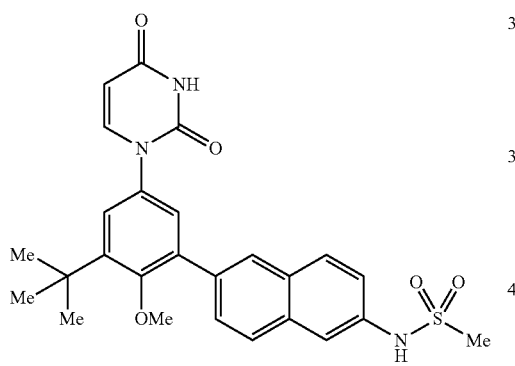

Tris(dibenzylideneacetone)dipalladium(0) (0.0026 g, 2.80 µmol), di-tert-butyl(2',4',6'-triisopropyl-3,6-dimethoxybiphenyl-2-yl)phosphine (0.0033 g, 6.72 µmol) and milled potassium phosphate tribasic (0.131 g, 0.616 mmol) were charged to a 40-mL reaction vial inside an inert atmosphere glove box. 2-Methyltetrahydrofuran (1.5 mL) was added, the vial was capped, and the contents were heated to 80° C. and stirred at this temperature for 30 minutes. The reaction mixture was cooled down to room temperature. 6-(3-tert-Butyl-5-(2,4-dioxo-3,4-dihydropyrimidin-1(2H)-yl)-2-methoxyphenyl)naphthalen-2-yl 1,1,2,2-tetrafluoro-2-(perfluoroethoxy)ethanesulfonate (0.4 g, 0.560 mmol, Example 3-7, compound (5f)), methanesulfonamide (0.064 g, 0.672 mmol) and ethyl acetate (3 mL) were added to the 40-mL reaction vial. The temperature of the closed vial was raised to 90° C. and the contents were magnetically stirred for 16 hours. HPLC analysis of the reaction mixture showed that the product was formed in 97 area % at 210 nm.

Example 4-8

Alternative preparation of N-(6-(3-tert-butyl-5-(2,4-dioxo-3,4-dihydropyrimidin-1(2H)-yl)-2-methoxyphenyl)naphthalen-2-yl)methanesulfonamide (compound (A-1))

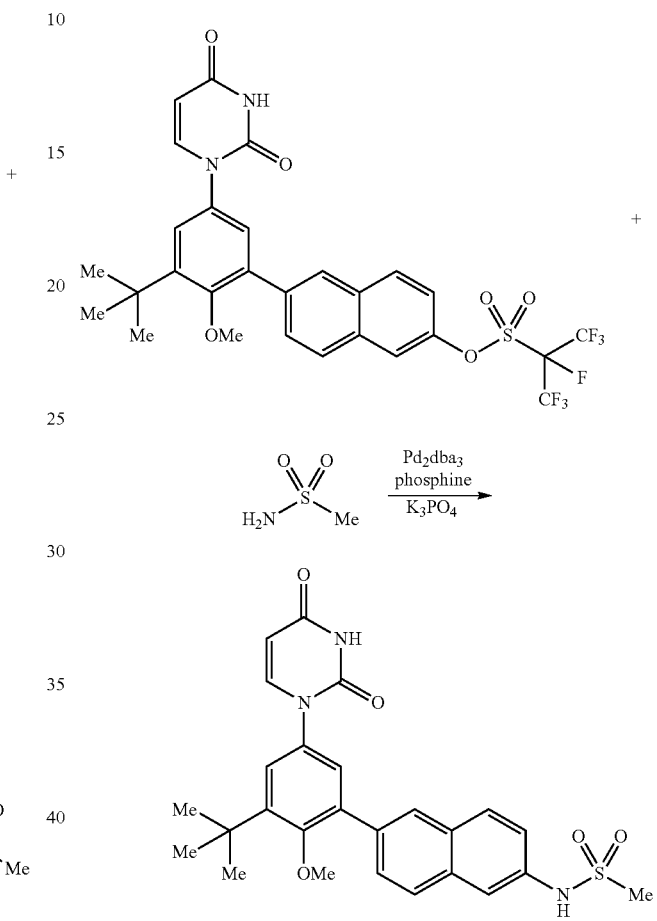

Tris(dibenzylideneacetone)dipalladium(0) (0.0071 g, 7.71 µmol), di-tert-butyl(2',4',6'-triisopropyl-3,6-dimethoxybiphenyl-2-yl)phosphine (0.0089 g, 19.0 µmol) and milled potassium phosphate tribasic (0.360 g, 1.696 mmol) were charged to a 40-mL reaction vial inside an inert atmosphere glove box. 2-Methyltetrahydrofuran (4 mL) was added, and the closed vial and its contents were heated to 80° C. with magnetic stirring for 30 minutes. The reaction mixture was cooled down to room temperature. 6-(3-tert-Butyl-5-(2,4-dioxo-3,4-dihydropyrimidin-1(2H)-yl)-2-methoxyphenyl)naphthalen-2-yl 1,1,1,2,3,3,3-heptafluoropropane-2-sulfonate (1.0 g, 1.542 mmol, Example 3-4, compound (5c)), methanesulfonamide (0.176 g, 1.850 mmol) and ethyl acetate (8 mL) were added to the 40-mL reaction vial. The temperature of the closed vial and its contents was raised to 90° C. and stirred for 20 hours. HPLC analysis of the reaction mixture showed that the product was formed in 95 area % at 210 nm.

Example 4-9

Alternative preparation of N-(6-(3-tert-butyl-5-(2,4-dioxo-3,4-dihydropyrimidin-1(2H)-yl)-2-methoxyphenyl)naphthalen-2-yl)methanesulfonamide (compound (A-1))

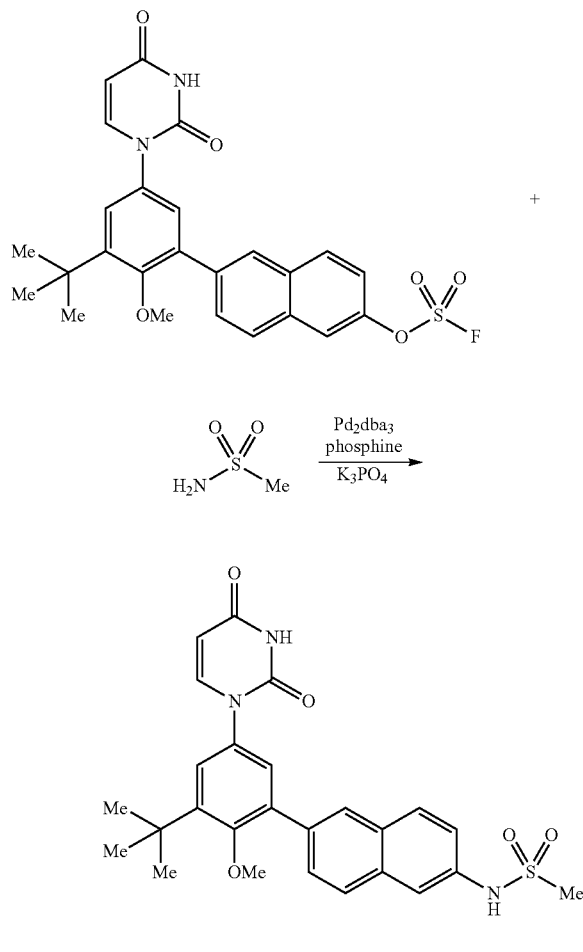

Tris(dibenzylideneacetone)dipalladium(0) (0.0055 g, 6.02 μmol), di-tert-butyl(2',4',6'-triisopropyl-3,6-dimethoxybiphenyl-2-yl)phosphine (0.0070 g, 14.0 μmol) and milled potassium phosphate tribasic (0.281 g, 1.324 mmol) were charged to a 40-mL reaction vial inside an inert atmosphere glove box. 2-Methyltetrahydrofuran (3.4 mL) was added, and the closed vial and its contents were heated to 80° C. with magnetic stirring for 30 minutes. The reaction mixture was cooled down to room temperature. 6-(3-tert-Butyl-5-(2,4-dioxo-3,4-dihydropyrimidin-1(2H)-yl)-2-methoxyphenyl)naphthalen-2-yl sulfofluoridate (0.6 g, 1.204 mmol, Example 3-8, compound (5g)), methanesulfonamide (0.137 g, 1.444 mmol) and ethyl acetate (6.7 mL) were added to the 40-mL reaction vial. The temperature of the closed reaction vial and its contents was raised to 90° C. and the contents were stirred for 20 hours. HPLC analysis of the reaction mixture showed that the product was formed in 79 area % at 210 nm.

Example 4-10

Alternative preparation of N-(6-(3-tert-butyl-5-(2,4-dioxo-3,4-dihydropyrimidin-1(2H)-yl)-2-methoxyphenyl)naphthalen-2-yl)methanesulfonamide (compound (A-1))

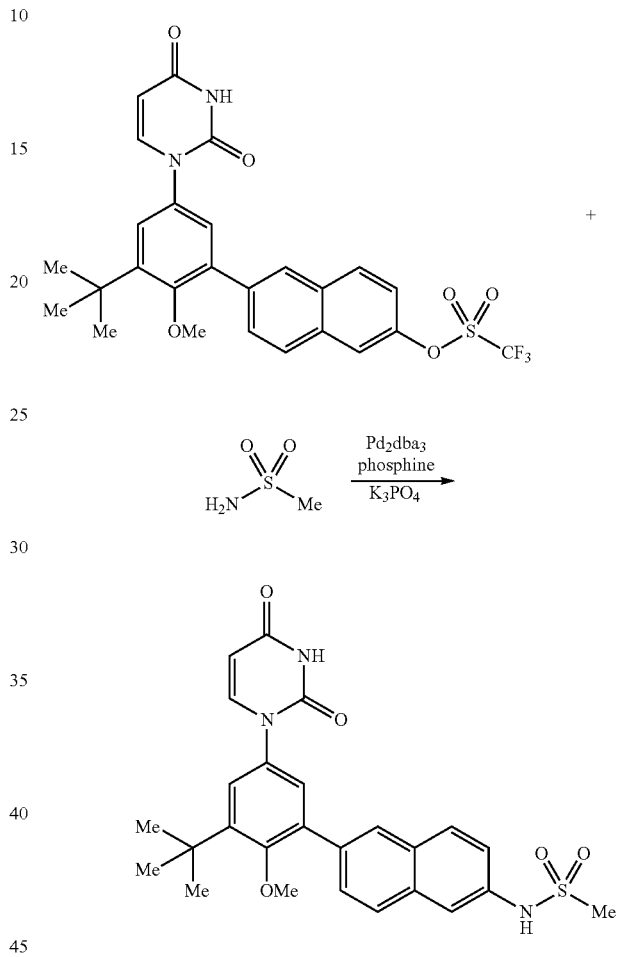

Tris(dibenzylideneacetone)dipalladium(0) (0.0042 g, 4.56 μmol), di-tert-butyl(2',4',6'-triisopropyl-3,6-dimethoxybiphenyl-2-yl)phosphine (0.0053 g, 12.0 μmol) and milled potassium phosphate tribasic (0.213 g, 1.003 mmol) were charged to a 40-mL reaction vial inside an inert atmosphere glove box. 2-Methyltetrahydrofuran (1.9 mL) was added, and the closed vial and its contents were heated to 80° C. with magnetic stirring for 30 minutes. The reaction mixture was cooled down to room temperature. 6-(3-tert-Butyl-5-(2,4-dioxo-3,4-dihydropyrimidin-1(211)-yl)-2-methoxyphenyl)naphthalen-2-yl trifluoromethanesulfonate (0.5 g, 0.912 mmol, Example 3-6, compound (5e)), methanesulfonamide (0.104 g, 1.094 mmol) and ethyl acetate (5.7 mL) were added to the 40-mL reaction vial. The temperature of the closed vial and its contents was raised to 90° C. and stirred for 14 hours. HPLC analysis of the reaction mixture showed that the product was formed in 91 area % at 210 nm.

Example 4-11

Alternative preparation of N-(6-(3-tert-butyl-5-(2,4-dioxo-3,4-dihydropyrimidin-1(2H)-yl)-2-methoxyphenyl)naphthalen-2-yl)methanesulfonamide (compound (A-1))

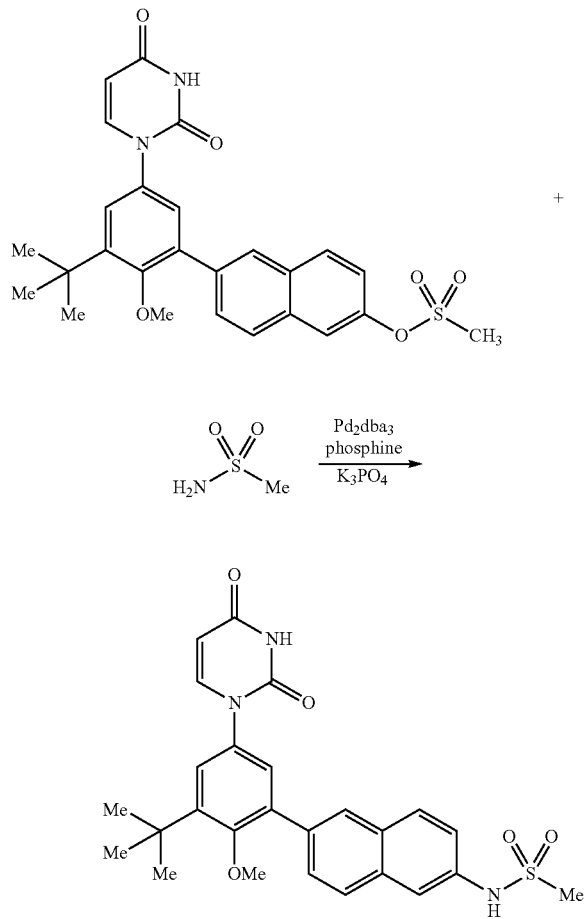

Tris(dibenzylideneacetone)dipalladium(0) (0.0037 g, 4.04 μmol), di-tert-butyl(2',4',6'-triisopropyl-3,6-dimethoxybiphenyl-2-yl)phosphine (0.0047 g, 9.7 μmol) and milled potassium phosphate tribasic (0.094 g, 0.445 mmol) were charged to a 40-mL reaction vial inside an inert atmosphere glove box. tert-Amyl alcohol (1.0 mL) was added, the contents were heated to 80° C. and stirred at this temperature for 30 minutes. The reaction mixture was cooled down to room temperature. 6-(3-tert-Butyl-5-(2,4-dioxo-3,4-dihydropyrimidin-1(2H)-yl)-2-methoxyphenyl)naphthalen-2-yl methanesulfonate (0.2 g, 0.404 mmol), methanesulfonamide (0.046 g, 0.485 mmol) and tert-amyl alcohol (1.5 mL) were added to a 40-mL reaction vial. The reaction temperature was raised to 110° C., and the contents were stirred for 14 hours. HPLC analysis of the reaction mixture showed that the titled compound was formed in 7 area % at 210 nm.

Example 4-12

Alternative preparation of N-(6-(3-tert-butyl-5-(2,4-dioxo-3,4-dihydropyrimidin-1(2H)-yl)-2-methoxyphenyl)naphthalen-2-yl)methanesulfonamide (compound (A-1))

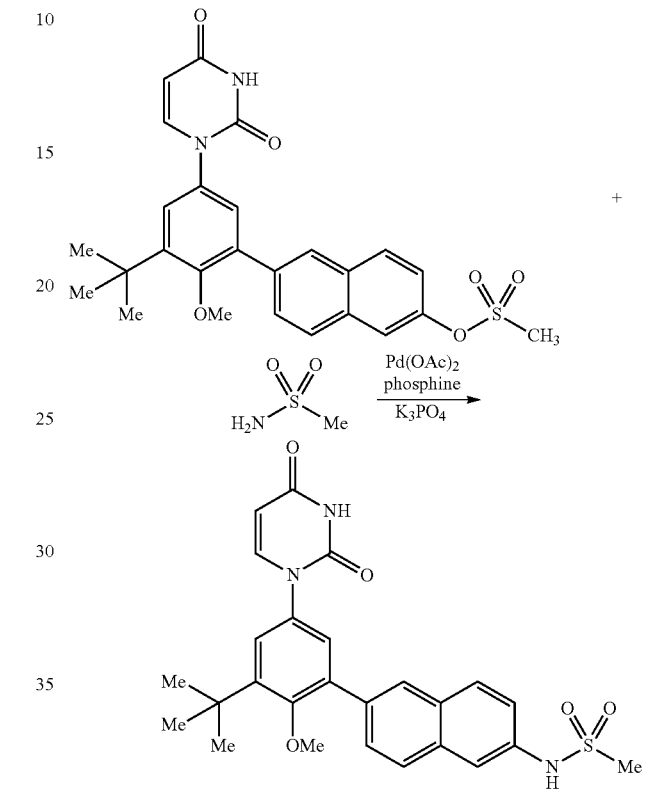

Palladium acetate (0.0018 g, 8.09 μmol), di-tert-butyl(2', 4',6'-triisopropyl-3,6-dimethoxybiphenyl-2-yl)phosphine (0.0086 g, 0.018 mmol) and water (0.6 μL, 0.032 mmol) were charged to a 40-mL reaction vial inside an inert atmosphere glove box. tert-Amyl alcohol (1.0 mL) was added, and the contents were heated to 80° C. and stirred at this temperature for 15 minutes. The reaction mixture was cooled down to room temperature. Potassium phosphate tribasic (0.094 g, 0.445 mmol), 6-(3-tert-butyl-5-(2,4-dioxo-3,4-dihydropyrimidin-1(2H)-yl)-2-methoxyphenyl)naphthalen-2-yl methanesulfonate (0.2 g, 0.404 mmol), methanesulfonamide (0.046 g, 0.485 mmol) and tert-amyl alcohol (1.5 mL) were added to the 40-mL reaction vial. The reaction temperature was raised to 110° C., and the contents were stirred for 14 hours. HPLC analysis of the reaction mixture showed that the titled compound was formed in 5 area % at 210 nm.

Example 4-13

Filterability of N-(6-(3-tert-butyl-5-(2,4-dioxo-3,4-dihydropyrimidin-1(2H)-yl)-2-methoxyphenyl)naphthalen-2-yl)methanesulfonamide (compound (A-1))

A filter pad was inserted in the leaf filter bottom, before attaching the assembly to the filter body. The top assembly was attached and sealed. The system was leak tested at 5-10 psig nitrogen to ensure a tight seal, the pressure was relieved, and the nitrogen line regulator set to the desired pressure for the filtration test. The distance from the filter pad to a reference mark on the filter body was measured using a tape measure. About 50 mL of the process solvent was charged to the filter, and the system was inspected to check for leaks. The filter top assembly was then attached to the filter body, and sealed. The solvent was passed through the filter to pre-wet the pad. The outlet valve was then closed.

About 200-250 mL of the slurry sample to be tested was transferred into a graduated cylinder. The graduated cylinder was weighed. A tared filtrate flask (receiver) was placed on an electronic balance located below the filter to collect the filtrate. Collection of the data signal from the electronic balance was started. The test slurry was charged into the filter body using a funnel, and the top assembly re-attached and sealed. The nitrogen pressure was checked, and re-adjusted to the target value, as necessary. The nitrogen inlet valve was opened to pressurize the filter body, and then the bottom drain valve was opened to start flow of filtrate into the receiver.

The actual nitrogen pressure achieved during the test was recorded. The filtrate weight was recorded as a function of time of filtration by the data collection system. The graduated cylinder was re-weighed to determine the weight of slurry charged. Once filtrate flow had stopped, the filtrate weight was determined, as well as the filtrate volume. The top assembly was opened, and the distance from the reference point on the filter body to the top of the solid wet cake was measured. This allowed calculation of the cake height by difference from the starting value. The filtrate density was calculated from the weight and volume of filtrate. (Alternatively, a tared 10 mL volumetric flask was filled to the mark with filtrate, and the weight determined to calculate the filtrate density). The slurry density was calculated from the weight and volume of slurry charged. The solvent viscosity was estimated using the pure solvent values, or, for mixtures by mass fraction averaging of the pure component viscosities. The filtration data were analyzed by plotting (t/V) versus V where t is the time (s) of filtration, and V is the volume of filtrate ($m^3$ or $ft^3$) collected up until time t. This allowed estimation of the filter cake resistance from the method outline in Geankoplis, C. J. "Transport Processes and Unit Operations", 3rd ed., copyright 1993. P T R Prentice-Hall, Inc, Englewood Cliffs, N.J., wherein the slope of the line on the (t/V) versus V plot is $K_p/2$ where $K_p = \mu \alpha C_s/(A^2 \Delta P g_c)$ where $\mu$=is the viscosity in Pa·s or ($lb_m/ft·s$)
$\alpha$=is the specific cake resistance, m/kg or $ft/lb_m$
$C_s$=solids concentration, $kg/m^3$ or $lb_m/ft^3$
A=cross-sectional area, $m^2$ or $ft^2$
$\Delta P$=pressure drop, $N/m^2$ or ($lb_f/ft^2$)
$g_c$=32.174 $lb_m$ ft/($lb_f$·s)

| Experiment | Pressure (psig) | Cake Resistance (ft/lb) | Permeability ($m^2$) | Reaction Crude Source [Free Acid Crystal Form] |
|---|---|---|---|---|
| 1 | 9 | 6.6 × $10^9$ | 2.3 × $10^{-13}$ | 2-methyltetrahydrofuran/ethyl acetate [ethyl acetate solvate] |
| 2 | 5 | 4.6 × $10^9$ | 3.9 × $10^{-13}$ | 2-methyltetrahydrofuran/ethyl acetate [ethyl acetate solvate] |
| 3 | 10 | 6.0 × $10^{10}$ | 4.4 × $10^{-14}$ | 2-methyltetrahydrofuran [anhydrate] |

-continued

| Experiment | Pressure (psig) | Cake Resistance (ft/lb) | Permeability ($m^2$) | Reaction Crude Source [Free Acid Crystal Form] |
|---|---|---|---|---|
| 4 | 23 | 3.65 × $10^{10}$ | 5.4 × $10^{-14}$ | 2-methyltetrahydrofuran [anhydrate] |
| 5 | 10 | 1.5 × $10^{11}$ | 2.3 × $10^{-14}$ | t-amyl alcohol [anhydrate] |

Cake Resistance Interpretation: 1 ft/lb = 0.67 kg/m
1.0 × $10^9$ ft/lb: moderately fast filtering
1.0 × $10^{10}$ ft/lb: slow but acceptable filtering
1.0 × $10^{11}$ ft/lb: very slow filtering
1.0 × $10^{12}$ ft/lb: difficult to filter As seen in the above table, reaction solvent mixtures in Experiments 1-4 provided enhanced rates of filtration.

Example 5

Preparation of the sodium salt of N-(6-(3-tert-butyl-5-(2,4-dioxo-3,4-dihydropyrimidin-1(2H)-yl)-2-methoxyphenyl)naphthalen-2-yl)methanesulfonamide (compound (A-s1))

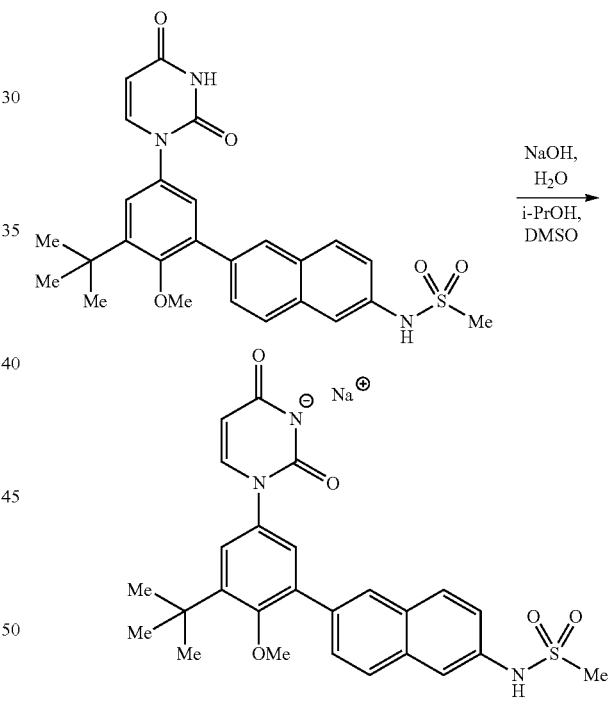

A solution of 2-propanol and water was prepared by combining 18.5 g of water and 512 g of 2-propanol. Hereafter, this solution is referred to as the "antisolvent solution."

A solution of 2-propanol and water was prepared by combining 23.94 g of water and 564 g of 2-propanol. This solution was cooled in a refrigerator prior to use. Hereafter, this solution is referred to as the "chilled wash solution."

A jacketed reactor was equipped with an overhead stirrer and charged with 32.0 g (64.8 mmol) of N-(6-(3-tert-butyl-5-(2,4-dioxo-3,4-dihydropyrimidin-1(2H)-yl)-2-methoxyphenyl)naphthalen-2-yl)methanesulfonamide and 105.9 g of dimethyl sulfoxide. With stirring the mixture was heated to an internal temperature of 68° C. A solution of 2.66 g of sodium hydroxide (66.5 mmol, 1.026 equiv) in 16 g of water was added to the reactor over several minutes, followed by 12.4 g of 2-propanol while maintaining the internal temperature at 68° C. Antisolvent solution (24.5 g) was added to the reactor while maintaining the internal temperature at 68° C. A slurry of 0.32 g of seed crystals of the final product in 22.8 g of antisolvent solution was added to the reactor, followed by a 2.6 g rinse of the flask with antisolvent solution. The reaction mixture was stirred for 1.5 hours while maintaining the internal temperature at 68° C. Antisolvent solution (354 g) was added to the reactor over 7 hours while maintaining the internal temperature at 68° C. The contents of the reactor were cooled to an internal temperature of 0° C. over 7 hours and then mixed at 0° C. for 7 hours. The solids were isolated by filtration and washed with 252 g of the chilled wash solution. The isolated solids were dried in a vacuum oven at 50° C. for 19 hours. The title compound was isolated as a white solid (30.7 g, 92% potency vs. free acid standard, 57.2 mmol free acid equivalent, 88% yield). $^1$H NMR (400 MHz, DMSO-$d_6$) δ ppm 7.75 (s, 1H), 7.72 (d, J=7.8 Hz, 1H), 7.59 (dd, J=8.8, 2.2 Hz, 2H), 7.45 (dd, J=8.5, 1.8 Hz, 1H), 7.27 (d, J=2.6 Hz, 2H), 7.21 (d, J=2.7 Hz, 1H), 7.06 (dd, J=8.8, 2.2 Hz, 1H), 5.62 (d, J=7.8 Hz, 1H), 3.24 (s, 3H), 2.68 (s, 3H), 1.40 (s, 9H).

All references (patent and non-patent) cited above are incorporated by reference into this patent application. The discussion of those references is intended merely to summarize assertions made by their authors. No admission is made that any reference (or a portion of a reference) is relevant prior art (or prior art at all). Applicants reserve the right to challenge the accuracy and pertinence of the cited references.

We claim:

1. A process for preparing compound (5-I), comprising:
reacting a compound of formula (4) or salt thereof with a sulfonylating agent in the presence of a solvent and a base:

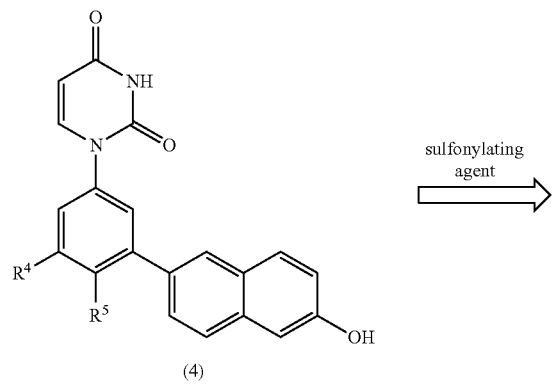

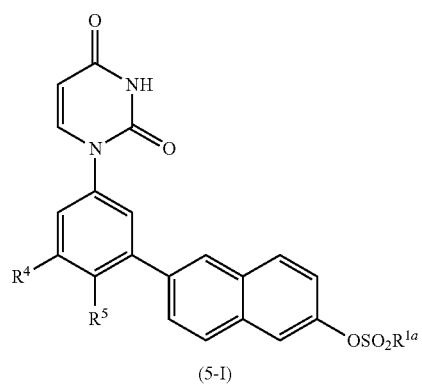

wherein $R^{1a}$ is, at each occurrence, independently selected from the group consisting of aryl, alkyl, fluoroalkyl, -fluoroalkyl-O-fluoroalkyl, —N(alkyl)$_2$, fluoro and imidazolyl;

$R^4$ is selected from the group consisting of $C_1$-$C_6$-alkyl, $C_1$-$C_6$-fluoroalkyl, phenyl, 2-thienyl, 3-thienyl, 2-furanyl, and 3-furanyl; and $R^5$ is selected from the group consisting of hydrogen, fluoro, chloro, $C_1$-$C_6$-alkyl, and $C_1$-$C_6$-alkyloxy;

wherein the sulfonylating agent corresponds in structure to

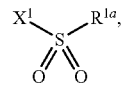

or

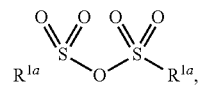

and $X^1$ is selected from the group consisting of bromine, chlorine, and fluorine.

2. The process of claim 1, wherein $R^{1a}$ is selected from the group consisting of p-tolyl, phenyl, methyl, ethyl, fluoro, trifluoromethyl, pentafluoroethyl, 1-heptafluoropropyl, 2-heptafluoropropyl, perfluorobutyl, isomers of perfluorobutyl, perfluoropentyl, perfluorohexyl, perfluorooctyl, and perfluoroethoxyethyl.

3. The process of claim 1, wherein $R^{1a}$ is perfluorobutyl.

4. The process of claim 1, wherein the sulfonylating agent is perfluorobutanesulfonyl fluoride.

5. The process of claim 1, wherein compound (5-I) has a structure corresponding to formula (5a):

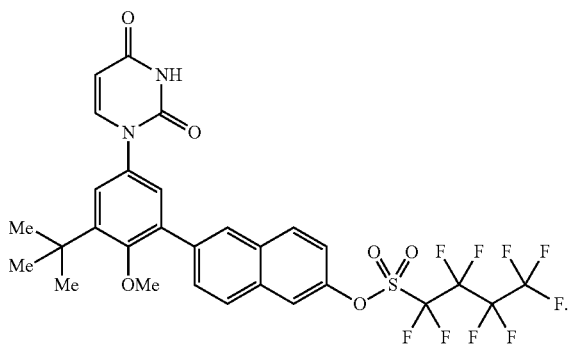

(5a)

6. The process of claim 1, wherein compound (5-I) has a structure corresponding to formula (5e):

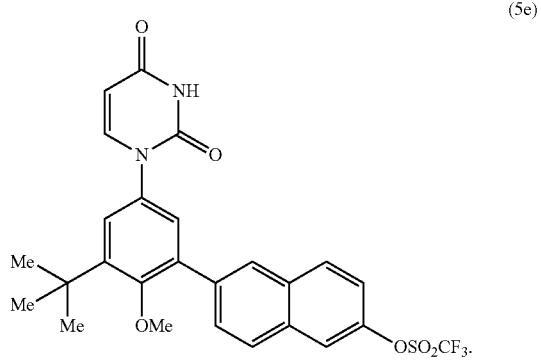

(5e)

7. The process of claim 1, wherein compound (4) has a structure corresponding to formula (4a):

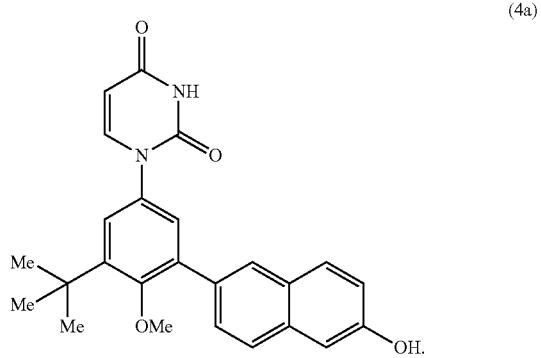 [SMILES: COc1c(-c2ccc3cc(O)ccc3c2)cc(-n2ccc(=O)[nH]c2=O)cc1C(C)(C)C]

(4a)

8. The process of claim 7, wherein compound (4a) is reacted with perfluorobutanesulfonyl fluoride to provide 6-(3-tert-butyl-5-(2,4-dioxo-3,4-dihydropyrimidin-1(2H)-yl)-2-methoxyphenyl)naphthalen-2-yl 1,1,2,2,3,3,4,4,4-nonafluorobutane-1-sulfonate (compound (5a)).

9. The process of claim 7, wherein compound (4a) is reacted with 1,1,2,2,3,3,3-heptafluoropropane-1-sulfonyl fluoride under an inert nitrogen atmosphere in N,N-dimethylformamide at ambient temperature in the presence of potassium carbonate to provide 6-(3-tert-butyl-5-(2,4-dioxo-3,4-dihydropyrimidin-1(2H)-yl)-2-methoxyphenyl)naphthalen-2-yl 1,1,2,2,3,3,-heptafluoropropane-1-sulfonate (compound (5b)).

10. The process of claim 7, wherein compound (4a) is reacted with 1,1,1,2,3,3,3-heptafluoropropane-2-sulfonyl fluoride under an inert nitrogen atmosphere in N,N-dimethylformamide at ambient temperature in the presence of potassium carbonate to provide 6-(3-tert-butyl-5-(2,4-dioxo-3,4-dihydropyrimidin-1(2H)-yl)-2-methoxyphenyl)naphthalen-2-yl 1,1,1,2,3,3,3-heptafluoropropane-2-sulfonate (compound (5c)).

11. The process of claim 7, wherein compound (4a) is reacted with 1,1,2,2,2-pentafluoroethanesulfonyl fluoride under an inert nitrogen atmosphere in N,N-dimethylformamide at ambient temperature in the presence of potassium carbonate to provide compound 6-(3-tert-butyl-5-(2,4-dioxo-3,4-dihydropyrimidin-1(2H)-yl)-2-methoxyphenyl) naphthalen-2-yl 1,1,2,2,2-pentafluoroethanesulfonate (compound (5d)).

12. The process of claim 7, wherein compound (4a) is reacted with trifluoromethanesulfonyl fluoride under an inert nitrogen atmosphere in N,N-dimethylformamide at ambient temperature in the presence of potassium carbonate to provide 6-(3-tert-butyl-5-(2,4-dioxo-3,4-dihydropyrimidin-1(2H)-yl)-2-methoxyphenyl)naphthalen-2-yl trifluoromethanesulfonate (compound (5e)).

13. The process of claim 7, wherein compound (4a) is reacted with perfluoro(2-ethoxyethane)sulfonyl fluoride under an inert nitrogen atmosphere in N,N-dimethylformamide at ambient temperature in the presence of potassium carbonate to provide 6-(3-tert-butyl-5-(2,4-dioxo-3,4-dihydropyrimidin-1(2H)-yl)-2-methoxyphenyl)naphthalen-2-yl 1,1,2,2-tetrafluoro-2-(perfluoroethoxy)ethanesulfonate (compound (5f)).

14. The process of claim 7, wherein compound (4a) is reacted with sulfuryl fluoride under an inert nitrogen atmosphere in N,N-dimethylformamide at ambient temperature in the presence of potassium carbonate to provide 6-(3-tert-butyl-5-(2,4-dioxo-3,4-dihydropyrimidin-1(2H)-yl)-2-methoxyphenyl)naphthalen-2-yl sulfofluoridate (compound (5g)).

15. The process of claim 1, wherein the sulfonylating agent is trifluoromethanesulfonyl fluoride.

16. The process of claim 1, wherein the sulfonylating agent is perfluorobutanesulfonyl fluoride; and the base is selected from the group consisting of sodium hydride, sodium hydroxide, sodium methoxide, sodium ethoxide, sodium tert-butoxide, potassium hydride, potassium hydroxide, potassium methoxide, potassium ethoxide, potassium tert-butoxide, potassium carbonate, cesium carbonate, sodium carbonate, sodium bicarbonate, triethylamine, diisopropylethylamine, 4-methylmorpholine, pyridine, and 2,6-dimethylpyridine.

17. The process of claim 1, wherein the sulfonylating agent is perfluorobutanesulfonyl fluoride; and the solvent is selected from the group consisting of tetrahydrofuran, 2-methyltetrahydrofuran, dimethyl sulfoxide, N,N-dimethylformamide, N,N-dimethylacetamide, N-methylpyrrolidone, 1,2-dimethoxyethane, 1,4-dioxane, acetonitrile, dichloromethane, chloroform, and diethyl ether.

18. A compound or salt thereof, wherein the compound corresponds in structure to formula (5-I):

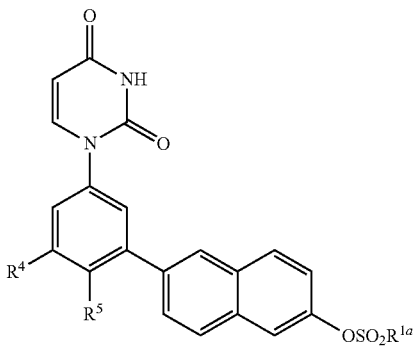

(5-I)

wherein R⁴ is selected from the group consisting of C₁-C₆-alkyl, C₁-C₆-fluoroalkyl, C₁-C₆-hydroxyalkyl, phenyl, 2-thienyl, 3-thienyl, 2-furanyl, and 3-furanyl;
R⁵ is selected from the group consisting of hydrogen, fluoro, chloro, C₁-C₆-alkyl, and C₁-C₆-alkyloxy; and
R¹ᵃ is selected from the group consisting of aryl, alkyl, fluoroalkyl, -fluoroalkyl-O-fluoroalkyl, —N(alkyl)₂, fluoro and imidazolyl.

19. The compound or salt of claim 18, wherein R⁴ is t-butyl, R⁵ is methoxy, and R¹ᵃ is —C₄F₉.

20. A composition comprising the compound or salt of claim 18 and an excipient.

21. The composition of claim 20, wherein R⁴ is t-butyl, R⁵ is methoxy, and R¹ᵃ is —C₄F₉.

22. The composition of claim 21, further comprising N-(6-(3-tert-butyl-5-(2,4-dioxo-3,4-dihydropyrimidin-1(2H)-yl)-2-methoxyphenyl)naphthalen-2-yl)methanesulfonamide (compound (A-1)) or a salt thereof.

23. The compound or salt of claim 18, wherein the compound is 6-(3-tert-butyl-5-(2,4-dioxo-3,4-dihydropyrimidin-1(2H)-yl)-2-methoxyphenyl)naphthalen-2-yl 1,1,2,2,3,3,4,4,4-nonafluorobutane-1-sulfonate.

24. The compound or salt of claim 18, wherein the compound is 6-(3-tert-butyl-5-(2,4-dioxo-3,4-dihydropyrimidin-1(2H)-yl)-2-methoxyphenyl)naphthalen-2-yl 1,1,2,2,3,3,3,-heptafluoropropane-1-sulfonate.

25. The compound or salt of claim 18, wherein the compound is 6-(3-tert-butyl-5-(2,4-dioxo-3,4-dihydropyrimidin-1(2H)-yl)-2-methoxyphenyl)naphthalen-2-yl 1, 1,1,2,3,3,3-heptafluoropropane-2-sulfonate.

26. The compound or salt of claim 18, wherein the compound is 6-(3-tert-butyl-5-(2,4-dioxo-3,4-dihydropyrimidin-1(2H)-yl)-2-methoxyphenyl)naphthalen-2-yl 1,1,2,2,2-pentafluoroethanesulfonate.

27. The compound or salt of claim 18, wherein the compound is 6-(3-tert-butyl-5-(2,4-dioxo-3,4-dihydropyrimidin-1(2H)-yl)-2-methoxyphenyl)naphthalen-2-yl trifluoromethanesulfonate.

28. The compound or salt of claim 18, wherein the compound is 6-(3-tert-butyl-5-(2,4-dioxo-3,4-dihydropyrimidin-1(2H)-yl)-2-methoxyphenyl)naphthalen-2-yl 1,1,2,2-tetrafluoro-2-(perfluoroethoxy)ethane sulfonate.

29. The compound or salt of claim 18, wherein the compound is 6-(3-tert-butyl-5-(2,4-dioxo-3,4-dihydropyrimidin-1(2H)-yl)-2-methoxyphenyl)naphthalen-2-yl sulfofluoridate.

30. A composition comprising 6-(3-tert-butyl-5-(2,4-dioxo-3,4-dihydropyrimidin-1(2H)-yl)-2-methoxyphenyl)naphthalen-2-yl 1,1,2,2,3,3,4,4,4-nonafluorobutane-1-sulfonate and N-(6-(3-tert-butyl-5-(2,4-dioxo-3,4-dihydropyrimidin-1(2H)-yl)-2-methoxyphenyl)naphthalen-2-yl)methanesulfonamide or a salt thereof.

* * * * *